United States Patent
Shah et al.

(10) Patent No.: US 7,390,835 B2
(45) Date of Patent: Jun. 24, 2008

(54) ARALKYL AMINES AS CANNABINOID RECEPTOR MODULATORS

(75) Inventors: Shrenik K. Shah, Metuchen, NJ (US); Quang T. Truong, Metuchen, NJ (US); Hongbo Qi, Edison, NJ (US); William K. Hagmann, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/576,381

(22) PCT Filed: Oct. 27, 2004

(86) PCT No.: PCT/US2004/035846

§ 371 (c)(1), (2), (4) Date: Apr. 19, 2006

(87) PCT Pub. No.: WO2005/044785

PCT Pub. Date: May 19, 2005

(65) Prior Publication Data

US 2007/0088058 A1    Apr. 19, 2007

Related U.S. Application Data

(60) Provisional application No. 60/515,705, filed on Oct. 30, 2003.

(51) Int. Cl.
C07C 211/00    (2006.01)
A01N 33/00    (2006.01)

(52) U.S. Cl. .................................. 514/579; 564/336

(58) Field of Classification Search .................. 514/579; 564/336
See application file for complete search history.

(56) References Cited

U.S. PATENT DOCUMENTS

| 3,753,978 | A | * | 8/1973 | Adelsberger et al. ......... 544/371 |
| 5,488,149 | A | * | 1/1996 | Nomoto et al. ............ 562/449 |
| 5,496,855 | A | | 3/1996 | Adams et al. |
| 5,849,747 | A | * | 12/1998 | Iwasawa et al. ............ 514/256 |
| 6,344,474 | B1 | | 2/2002 | Maruani et al. |
| 6,355,631 | B1 | | 3/2002 | Achard et al. |
| 6,359,175 | B1 | | 3/2002 | Philippe et al. |
| 6,380,224 | B1 | | 4/2002 | Dax et al. |
| 6,479,479 | B2 | | 11/2002 | Achard et al. |
| 6,566,356 | B2 | | 5/2003 | Achard et al. |
| 6,734,176 | B2 | | 5/2004 | Achard et al. |
| 6,872,717 | B2 | | 3/2005 | Achard et al. |
| 6,930,122 | B2 | | 8/2005 | Blanchard et al. |
| 6,972,295 | B2 | | 12/2005 | Hagmann et al. |
| 2002/0019383 | A1 | | 2/2002 | Achard et al. |
| 2002/0128302 | A1 | | 9/2002 | Maruani et al. |
| 2003/0087933 | A1 | | 5/2003 | Blanchard et al. |
| 2003/0096844 | A1 | | 5/2003 | Kozlowski et al. |
| 2003/0232859 | A1 | | 12/2003 | Kozlowski et al. |
| 2004/0058820 | A1 | | 3/2004 | Hagmann et al. |
| 2004/0248956 | A1 | | 12/2004 | Hagmann et al. |
| 2005/0154202 | A1 | | 7/2005 | Hagmann et al. |
| 2005/0187208 | A1 | | 8/2005 | Altisen et al. |
| 2005/0203112 | A1 | | 9/2005 | Castonguay et al. |
| 2005/0239828 | A1 | | 10/2005 | Hagmann et al. |
| 2006/0009528 | A1 | | 1/2006 | Kozlowski et al. |
| 2006/0052388 | A1 | | 3/2006 | Dax et al. |
| 2006/0106071 | A1 | | 5/2006 | Lin et al. |

FOREIGN PATENT DOCUMENTS

| WO | WO 03/006007 | 1/2003 |
| WO | WO 2004/048317 | 6/2004 |
| WO | WO 2005/000809 | 1/2005 |
| WO | WO 2005/009479 | 2/2005 |
| WO | WO 2005/027837 | 3/2005 |
| WO | WO 2005/044785 | 5/2005 |
| WO | WO 2005/077909 | 8/2005 |
| WO | WO 2006/018662 | 2/2006 |
| WO | WO 2006/041797 | 4/2006 |

OTHER PUBLICATIONS

Lancet, 2005, v. 365, p. 1363-1364.*
Vizi et al., Eur. J. of Pharmacol., vol. 431 (2001), pp. 237-244, "Evidence for presynaptic cannabinoid CB1 receptor-mediated inhibition of noradrenaline release in the guinea pig lung".

* cited by examiner

*Primary Examiner*—Kamal A. Saeed
*Assistant Examiner*—Robert Havlin
(74) *Attorney, Agent, or Firm*—Baerbel R. Brown; Catherine D. Fitch

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, including alcohol and nicotine addiction, the treatment of obesity or eating disorders, as well as the treatment of asthma, constipation, chronic intestinal pseudo-obstruction, and cirrhosis of the liver.

11 Claims, No Drawings

ARALKYL AMINES AS CANNABINOID RECEPTOR MODULATORS

CROSS-REFERENCE TO RELATED APPLICATIONS

This application is a U.S. National Phase application under 35 U.S.C. §371 of PCT Application No. PCT/US2004/035846, filed Oct. 27, 2004, which claims priority under 35 U.S.C. §119 from U.S. provisional application No. 60/515,705, filed Oct. 30, 2003.

BACKGROUND OF THE INVENTION

Marijuana (*Cannabis sativa* L.) and its derivatives have been used for centuries for medicinal and recreational purposes. A major active ingredient in marijuana and hashish has been determined to be Δ9-tetrahydrocannabinol (Δ9-THC). Detailed research has revealed that the biological action of Δ9-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonoyl glycerol ether). Each is an agonist with activities similar to Δ9-THC, including sedation, hypothermia, intestinal immobility, antinociception, analgesia, catalepsy, anti-emesis, and appetite stimulation.

There are at least two CB1 modulators characterized as inverse agonists or antagonists, N-(1-piperidinyl)-5-(4-chlorophenyl)-1-(2,4-dichlorophenyl)-4-methylpyrazole-3-carboxamide (SR141716A) and 3-(4-chlorophenyl-N'-(4-chlorophenyl)sulfonyl-N-methyl-4-phenyl-4,5-dihydro-1H-pyrazole-1-carboxamidine (SLV319), in clinical trials for treatment of eating disorders at this time. There still remains a need for potent low molecular weight CB1 modulators that have pharmacokinetic and pharmacodynamic properties suitable for use as human pharmaceuticals.

U.S. Pat. Nos. 5,624,941; 6,028,084; and 6,509,367; PCT Publications WO98/43636 and WO98/43635, and EP-658546 disclose substituted pyrazoles having activity against the cannabinoid receptors.

PCT publication WO 03/077847 discloses substituted amide compounds useful as modulators of the CB1 receptor. U.S. Pat. No. 4,973,587, U.S. Pat. No. 5,013,837, U.S. Pat. No. 5,081,122, and U.S. Pat. No. 5,112,820, U.S. Pat. No. 5,292,736 disclose aminoalkylindole derivatives as having activity against the cannabinoid receptors.

Other cannabinoid receptor modulating compounds are disclosed in WO 01/70700, WO 02/076949; WO 03/026647; WO 03/026648; WO 03/027069; WO 03/027076; and WO 03/027114. Cite key structural references.

The compounds of the present invention are modulators of the Cannabinoid-1 (CB1) receptor and are useful in the treatment, prevention and suppression of diseases mediated by the Cannabinoid-1 (CB1) receptor. Compounds of the present invention are antagonists or inverse agonists of the CB1 receptor. The invention is concerned with the use of these compounds to modulate the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, such as for example, those relating to opiates, alcohol, marijuana, and nicotine. The compounds are also useful for the treatment of eating disorders by inhibiting excessive food intake and the resulting obesity and complications associated therewith, including left ventricular hypertrophy. The compounds are also useful for the treatment of constipation and chronic intestinal pseudo-obstruction, as well as for the treatment of asthma, and cirrhosis of the liver.

SUMMARY OF THE INVENTION

The present invention is concerned with substituted aralkyl amine derivatives of general formula I:

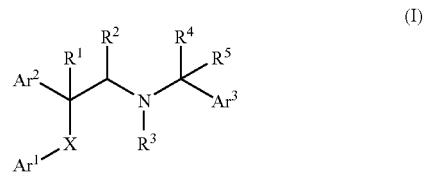

stereoisomers and pharmaceutically acceptable salts thereof which are antagonists and/or inverse agonists of the Cannabinoid-1 (CB1) receptor and are useful in the treatment, prevention or suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, such as for example, those relating to opiates, alcohol, marijuana, and nicotine, including smoking cessation. The compounds are also useful for the treatment of obesity or eating disorders associated with excessive food intake and complications associated therewith, including left ventricular hypertrophy. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals, including sivmastatin, and PYY 3-36.

The invention is also concerned with pharmaceutical formulations comprising one of the compounds as an active ingredient.

The invention is further concerned with processes for preparing the compounds of formula I.

DETAILED DESCRIPTION OF THE INVENTION

The compounds of the present invention are represented by structural formula I:

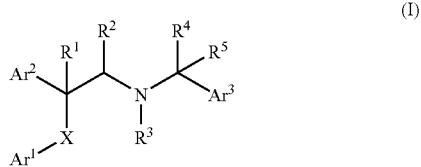

or a pharmaceutically acceptable salt thereof.

In one embodiment of the present invention, $R^1$ is selected from: hydrogen; $C_{1-4}$alkyl, unsubstituted or substituted with 1, 2 or 3 $R^e$ substituents; halogen; and —$OR^d$.

In one class of this embodiment, $R^1$ is selected from: hydrogen, methyl, trifluoromethyl, ethyl, isopropyl, butyl, tert.-butyl, halogen, hydroxy, methoxy, and ethoxy.

In a subclass of this class, $R^1$ is selected from: hydrogen, methyl, and halogen.

In yet another subclass, $R^1$ is hydrogen.

In another embodiment of the present invention, $R^2$ is selected from: hydrogen, $C_{1-4}$alkyl, and aryl; wherein alkyl and aryl moieties are unsubstituted or substituted with 1, 2 or 3 $R^e$ substituents.

In one class of this embodiment, $R^2$ is selected from: hydrogen, methyl, ethyl, isopropyl, and phenyl; wherein the alkyl and phenyl moieties are unsubstituted or substituted with 1, 2 or 3 $R^e$ substituents.

In one subclass of this class, $R^2$ is selected from: methyl, ethyl, and phenyl.

In another subclass, $R^2$ is methyl.

In yet another embodiment, $R^3$ is selected from: hydrogen, and $C_{1-4}$alkyl, unsubstituted or substituted with 1, 2 or 3 $R^e$ substituents.

In one class of this embodiment, $R^3$ is selected from: hydrogen, and methyl.

In one subclass of this class, $R^3$ is hydrogen.

In one embodiment, $R^4$ is selected from: hydrogen, $C_{1-10}$alkyl, $C_{2-10}$alkenyl, $C_{2-10}$alkynyl, $C_{1-10}$alkyloxycarbonyl, $C_{3-10}$cycloalkyl, aryl-$C_{1-6}$alkyl-, and heteroaryl-$C_{1-6}$alkyl-; wherein each alkyl, alkenyl, and alkynyl moiety is unsubstituted or substituted with one to four substituents independently selected from $R^a$ and each cycloalkyl moiety is unsubstituted or substituted with one, two or three substituents independently selected from $R^b$ and oxo.

In one class of this embodiment, $R^4$ is selected from: hydrogen, $C_{1-10}$alkyl, $C_{1-5}$alkyloxycarbonyl, $C_{3-10}$cycloalkyl, aryl-$C_{1-3}$alkyl-, and heteroaryl-$C_{1-3}$alkyl-; wherein each alkyl moiety is unsubstituted or substituted with one to four substituents independently selected from $R^a$ and the each aryl, heteroaryl and cycloalkyl moiety is unsubstituted or substituted with one, two or three substituents independently selected from $R^b$ and oxo.

In one subclass of this class, $R^4$ is selected from: $C_{1-6}$alkyl, $C_{1-5}$alkyloxycarbonyl, $C_{3-6}$cycloalkyl, aryl-$C_{1-3}$alkyl-, and heteroaryl-$C_{1-3}$alkyl-; wherein each alkyl moiety is unsubstituted or substituted with one to two substituents independently selected from $R^a$ and each aryl, heteroaryl and cycloalkyl moiety is unsubstituted or substituted with a hydroxy or oxo substituent.

In still another subclass of this class, $R^4$ is selected from: methyl, ethyl, isopropyl, tert-butyl, 1-ethylpropyl, $C_{1-5}$alkyl, 1-hydroxycyclobutyl, 1-hydroxycyclopentyl, 1-hydroxycyclohexyl, cyanomethyl, 1,1-dimethyl-cyano-methyl-, pyrazolylmethyl-, triazolylmethyl-, 2-oxopyridin-1-yl-methyl-, 1,1-dimethyl-1-pyrazol-1-yl-methyl, 1,1-dimethyl-triazolylmethyl; wherein each alkyl moiety is unsubstituted or substituted with one to two substituents independently selected from $R^a$.

In another embodiment, $R^4$ is selected from: hydrogen, $C_{1-10}$alkyl, $C_{2-10}$alkenyl, $C_{2-10}$alkynyl, $C_{1-10}$alkyloxycarbonyl, and $C_{3-10}$cycloalkyl; wherein each alkyl, alkenyl, and alkynyl moiety is unsubstituted or substituted with one to four substituents independently selected from $R^a$ and each cycloalkyl moiety is unsubstituted or substituted with one, two or three substituents independently selected from $R^b$.

In one class of this embodiment, $R^4$ is selected from: hydrogen, $C_{1-10}$alkyl, $C_{1-5}$alkyloxycarbonyl, and $C_{3-10}$cycloalkyl; wherein each alkyl moiety is unsubstituted or substituted with one to four substituents independently selected from $R^a$ and the cycloalkyl moiety is unsubstituted or substituted with one, two or three substituents independently selected from $R^b$.

In one subclass of this class, $R^4$ is selected from: $C_{1-6}$alkyl, $C_{1-5}$alkyloxycarbonyl, and $C_{3-6}$cycloalkyl; wherein each alkyl moiety is unsubstituted or substituted with one to two substituents independently selected from $R^a$ and the cycloalkyl moiety is unsubstituted or substituted with a hydroxy substituent at the 1-position.

In another subclass of this class, $R^4$ is selected from: methyl, ethyl, isopropyl, tert-butyl, 1-ethylpropyl, $C_{1-5}$alkyl, 1-hydroxycyclobutyl, 1-hydroxycyclopentyl, and 1-hydroxycyclohexyl; wherein each alkyl moiety is unsubstituted or substituted with one to two substituents independently selected from $R^a$.

In one embodiment of the present invention, $R^5$ is selected from: hydrogen, and $C_{1-4}$alkyl, unsubstituted or substituted with 1, 2 or 3 $R^e$ substituents.

In one class of the present embodiment, $R^5$ is selected from: hydrogen, methyl, and trifluoromethyl.

In one subclass, $R^5$ is hydrogen.

In one embodiment of the present invention, $Ar^1$ is selected from: $C_{1-10}$alkyl, $C_{2-10}$alkenyl, $C_{2-10}$alkynyl, $C_{3-10}$cycloalkyl, cycloheteroalkyl, aryl, and heteroaryl; wherein: alkyl, alkenyl, and alkynyl are unsubstituted or substituted with one to three substituents independently selected from $R^a$; aryl, and heteroaryl are unsubstituted or substituted with one to four substituents independently selected from $R^b$; and cycloalkyl and cycloheteroalkyl are unsubstituted or substituted with one to four substituents independently selected from $R^b$ and oxo.

In one class of this embodiment, $Ar^1$ is selected from: $C_{1-10}$alkyl, $C_{3-10}$cycloalkyl, cycloheteroalkyl, phenyl, and heteroaryl; wherein: alkyl, alkenyl, and alkynyl are unsubstituted or substituted with one to three substituents independently selected from $R^a$; aryl, and heteroaryl are unsubstituted or substituted with one to four substituents independently selected from $R^b$; and cycloalkyl and cycloheteroalkyl are unsubstituted or substituted with one to four substituents independently selected from $R^b$ and oxo.

In one subclass of this class, $Ar^1$ is selected from: $C_{1-5}$alkyl; $C_{3-6}$cycloalkyl; piperidinyl, unsubstituted or substituted on nitrogen with tert-butyloxycarbonyl; phenyl, unsubstituted or substituted with one or two halogen substituents; and pyridyl, unsubstituted or substituted on carbon with one or two halogen moieties.

In another subclass, $Ar^1$ is phenyl, unsubstituted or substituted with one or two halogen substituents selected from fluoro and chloro.

In still another subclass, $Ar^1$ is para-chlorophenyl.

In one embodiment of the present invention, $Ar^2$ is selected from: $—OR^d$, $—CO_2R^d$, $C_{3-10}$cycloalkyl, cycloheteroalkyl, aryl, and heteroaryl; wherein cycloalkyl, cycloheteroalkyl are unsubstituted or substituted with one to four substituents independently selected from $R^b$ and oxo; and aryl and heteroaryl are unsubstituted or substituted with one to four substituents independently selected from $R^b$.

In one class of this embodiment of the present invention, $Ar^2$ is selected from: $C_{3-10}$cycloalkyl-$C_{1-6}$alkyloxy, unsubstituted or substituted with one to three $R^h$ substituents; benzyloxycarbonyl, unsubstitute or substituted with one to three $R^h$ substituents; $C_{3-6}$cycloalkyl, unsubstituted or substituted with one to three substitutents selected from $R^b$ and oxo; pyrrolidinyl, unsubstituted or substituted with one to three substitutents selected from $R^b$ and oxo; benzoisoxazolyl, unsubstituted or substituted with one to three substitutents selected from $R^b$ and oxo; indolinyl, unsubstituted or substituted with one to three substitutents selected from $R^b$ and oxo; 2,3-dihydro-1H-indolyl, unsubstituted or substituted with one to three substitutents selected from $R^b$ and oxo; 3,4-dihydroquinolinyl, unsubstituted or substituted with one to three substitutents selected from $R^b$ and oxo; 1H-indazolyl, unsubstituted or substituted with one to three substituents selected from $R^b$ and oxo; phenyl, unsubstituted or substituted with one to three $R^b$ substituents; 1H-indolyl, unsubstituted or substituted with one to three $R^b$ substituents; pyridyl, unsubstituted or substituted with one to three $R^b$ substituents; triazolyl, unsubstituted or substituted with one to three $R^b$ substituents; pyridazinyl, unsubstituted or substituted with one to three $R^b$ substituents; pyrimidinyl, unsubstituted or substituted with one to three $R^b$ substituents; thiophenyl, unsubstituted or substituted with one to three $R^b$ substituents; 7-azaindolinyl, unsubstituted or substituted with one to three $R^b$ substituents; benzisoxazolyl, unsubstituted or substituted with one to three $R^b$ substituents; indolyl, unsubstituted or substituted with one to three $R^b$ substituents, and benzotriazolyl, unsubstituted or substituted with one to three $R^b$ substituents.

In another class, $Ar^2$ is selected from: aryl and heteroaryl, wherein aryl and heteroaryl are optionally substituted with one to three substituents independently selected from $R^b$.

In a subclass of this class, $Ar^2$ is selected from: phenyl, unsubstituted or substituted with one to three $R^b$ substituents; and pyridyl, unsubstituted or substituted with one to three $R^b$ substituents.

In an additional subclass of this class, $Ar^2$ is selected from: phenyl, unsubstituted or substituted with an $R^b$ substituent; and pyridyl, unsubstituted or substituted with one $R^b$ substituent.

In yet another subclass, $Ar^2$ is 3-cyanophenyl.

In one embodiment of the present invention, $Ar^3$ is selected from: cycloalkyl, aryl, and heteroaryl; wherein cycloalkyl, aryl and heteroaryl are unsubstituted or substituted with one to four substituents independently selected from $R^b$.

In one class of this embodiment, $Ar^3$ is selected from: cyclohexyl, phenyl, and pyridyl; wherein cyclohexyl, phenyl and pyridyl are unsubstituted or substituted with one to three substituents independently selected from $R^b$.

In one subclass of this class, $Ar^3$ is cyclohexyl or phenyl, unsubstituted or substituted with one or two substituents selected from: halogen, cyano, $—CH_3$, $—OCH_3$, $—CF_3$, $—OCF_3$, $—CO_2CH_3$, $—SCH_3$, $—S(O)CH_3$, $—S(O)_2CH_3$, $—C(O)N(CH_3)_2$, phenyl, pyridinyl, pyrimidinyl, pyrazolyl, pyrrolyl, triazolyl, $—NH—R^d$ wherein phenyl and heteroaryl moieties are unsubstituted or substituted with a substituent selected from halogen, methyl, cyano and amino.

In one embodiment of the present invention, $Ar^3$ is selected from: aryl, and heteroaryl; wherein aryl and heteroaryl are unsubstituted or substituted with one to four substituents independently selected from $R^b$.

In one class of this embodiment, $Ar^3$ is selected from: phenyl, and pyridyl; wherein phenyl and pyridyl are unsubstituted or substituted with one to three substituents independently selected from $R^b$. In one subclass of this class, $Ar^3$ is phenyl, unsubstituted or substituted with one or two halogen substituents.

In one embodiment of the present invention, X is selected from: a bond, $—C_{1-4}$alkyl-, oxygen, sulfur, $—NR^c—$, provided that when X is oxygen, sulfur, or $—NR^c—$, then $R^1$ is hydrogen or $C_{1-4}$alkyl and $Ar^2$ is not $—OR^d$.

In one class of this embodiment, X is selected from: a bond, $C_{1-4}$alkyl, oxygen, sulfur; provided that when X is oxygen or sulfur, then $R^1$ is hydrogen or $C_{1-4}$alkyl and $Ar^2$ is not $—OR^d$.

In one subclass of this class, X is selected from: a bond, $—CH_2—$, oxygen, sulfur, provided that when X is oxygen, or sulfur, then $R^1$ is hydrogen or $C_{1-4}$alkyl and $Ar^2$ is not $—OR^d$.

In another subclass, X is $—CH_2—$.

In one embodiment of the present invention, each $R^a$ is independently selected from: $—OR^d$, $—NR^cS(O)_mR^d$, halogen, $—SR^d$, $—S(O)_mR^d$, $—S(O)_mNR^cR^d$, $—NR^cR^d$, $—C(O)R^d$, $—CO_2R^d$, $—CN$, $—C(O)NR^cR^d$, $—NR^cC(O)R^d$, $—NR^cC(O)OR^d$, $—NR^cC(O)NR^cR^d$, $—CF_3$, $—OCF_3$, and cycloheteroalkyl.

In one class of this embodiment, each $R^a$ is independently selected from: $—OR^d$, $—NHS(O)_2R^d$, halogen, $—SR^d$, $—S(O)_2R^d$, $—S(O)_2NR^cR^d$, $—NR^cR^d$, $—C(O)R^d$, $—CO_2R^d$, $—CN$, $—C(O)NR^cR^d$, $—NHC(O)R^d$, $—NHC(O)OR^d$, $—NHC(O)NR^cR^d$, $—CF_3$, and $—OCF_3$.

In one subclass of this class, each $R^a$ is independently selected from: hydroxy, methoxy, halogen, methylthio, methylsulfonyl, $—NH_2$, $—NHCH_3$, $—N(CH_3)_2$, methylcarbonyl, methoxycarbonyl, t-butyoxycarbonyl, $—CN$, $—NHC(O)CH_3$, $—NHC(O)OC(CH_3)_3$, $—CF_3$, and $—OCF_3$.

In another subclass, each $R^a$ is independently selected from: hydroxy, methoxy, halogen, methylsulfonyl, $—NH_2$, $—NHCH_3$, $—N(CH_3)_2$, methoxycarbonyl, $—CN$, $—NHC(O)CH_3$, and $—NHC(O)OC(CH_3)_3$.

In one embodiment of the present invention, each $R^b$ is independently selected from: $R^a$, $C_{1-10}$alkyl, aryl, aryl$C_{1-4}$alkyl, heteroaryl, and heteroaryl$C_{1-4}$alkyl, wherein aryl and heteroaryl moieties are unsubstituted or substituted with one, two or three substituents independently selected from $R^f$.

In one class of this embodiment, each $R^b$ is independently selected from: $R^a$, $C_{1-3}$alkyl, phenyl, and heteroaryl, wherein aryl and heteroaryl moieties are unsubstituted or substituted with one or two substituents independently selected from $R^f$.

In one subclass of this class, each $R^b$ is independently selected from: hydroxy, methoxy, halogen, methylthio, $—NH_2$, $—NHCH_3$, $—N(CH_3)_2$, methylcarbonyl, methoxycarbonyl, t-butyoxycarbonyl, $—CN$, $—CF_3$, $—OCF_3$, $—CH_3$, $—OCH_3$, $—S(O)CH_3$, $—S(O)_2CH_3$, $—C(O)N(CH_3)_2$, phenyl, pyridinyl, pyrimidinyl, pyrazolyl, pyrrolyl, triazolyl, $—NH—R^d$, wherein phenyl and heteroaryl moieties are unsubstituted or substituted with a substituent selected from halogen, methyl, cyano and amino.

In one embodiment of the present invention, each $R^b$ is independently selected from: $R^a$, $C_{1-10}$alkyl, aryl, aryl$C_{1-4}$alkyl, heteroaryl, and heteroaryl$C_{1-4}$alkyl.

In one class of this embodiment, each $R^b$ is independently selected from: $R^a$, and $C_{1-3}$alkyl.

In one subclass of this class, each $R^b$ is independently selected from: hydroxy, methoxy, halogen, methylthio, —NH$_2$, —NHCH$_3$, —N(CH$_3$)$_2$, methylcarbonyl, methoxycarbonyl, t-butyoxycarbonyl, —CN, —CF$_3$, —OCF$_3$, and methyl.

In one embodiment of the present invention, R$^c$ and R$^d$ are independently selected from: hydrogen, C$_{1-10}$alkyl, C$_{2-10}$alkenyl, cycloalkyl, cycloalkyl-C$_{1-10}$alkyl, cycloheteroalkyl, cycloheteroalkyl-C$_{1-10}$alkyl, aryl, heteroaryl, aryl-C$_{1-10}$alkyl, and heteroaryl-C$_{1-10}$alkyl; or R$^c$ and R$^d$ together with the atom(s) to which they are attached form a heterocyclic ring of 4 to 7 members containing 0-2 additional heteroatoms independently selected from oxygen, sulfur and N—R$^g$; wherein: each R$^c$ and R$^d$ may be unsubstituted or substituted with one to three substituents selected from R$^h$.

In one class of this embodiment, R$^c$ and R$^d$ are independently selected from: hydrogen, C$_{1-10}$alkyl, cycloalkyl, cycloalkyl-C$_{1-10}$alkyl, cycloheteroalkyl, cycloheteroalkyl-C$_{1-10}$alkyl, aryl, heteroaryl, aryl-C$_{1-10}$alkyl, and heteroaryl-C$_{1-10}$alkyl; wherein: each R$^c$ and R$^d$ may be unsubstituted or substituted with one to three substituents selected from R$^h$.

In one class of this embodiment, R$^c$ is selected from hydrogen and methyl, and R$^d$ is selected from: hydrogen, C$_{1-6}$alkyl, cycloalkyl, cycloalkyl-C$_{1-3}$alkyl, cycloheteroalkyl, cycloheteroalkyl-C$_{1-3}$alkyl, phenyl, pyridyl, triazolyl, pyrazolyl, phenyl-C$_{1-3}$alkyl, pyridyl-C$_{1-3}$alkyl, triazolyl-C$_{1-3}$alkyl, pyrazolyl-C$_{1-3}$alkyl; wherein each R$^c$ and R$^d$ may be unsubstituted or substituted with one to three substituents selected from R$^h$.

In one subclass of this class, R$^c$ is selected from hydrogen and methyl, and R$^d$ is selected from: hydrogen, C$_{1-4}$alkyl, cycloalkylmethyl, phenyl, pyridyl, triazolyl, pyrazolyl, benzyl, and pyridylmethyl; wherein each R$^c$ and R$^d$ may be unsubstituted or substituted with one to three substituents selected from R$^h$.

In one class of this embodiment, R$^c$ is selected from hydrogen and methyl, and R$^d$ is selected from: hydrogen, C$_{1-6}$alkyl, cycloalkyl, cycloalkyl-C$_{1-3}$alkyl, cycloheteroalkyl, cycloheteroalkyl-C$_{1-3}$alkyl, phenyl, pyridyl, phenyl-C$_{1-3}$alkyl, and pyridyl-C$_{1-3}$alkyl; wherein each R$^c$ and R$^d$ may be unsubstituted or substituted with one to three substituents selected from R$^h$.

In one subclass of this class, R$^c$ is selected from hydrogen and methyl, and R$^d$ is selected from: hydrogen, C$_{1-4}$alkyl, cycloalkylmethyl, phenyl, pyridyl, benzyl, and pyridylmethyl; wherein each R$^c$ and R$^d$ may be unsubstituted or substituted with one to three substituents selected from R$^h$.

In one embodiment of the present invention, each R$^e$ is independently selected from: hydroxy, methoxy, trifluoromethoxy, methylcarbonyloxy, halogen, and cyano.

In one embodiment of the present invention, each R$^f$ is independently selected from: halogen, methyl, cyano, and amino.

In one class of this embodiment, R$^f$ is selected from chloro, bromo, methyl, cyano and amino.

In another embodiment of the present invention, R$^g$ is selected from: C$_{1-10}$alkyl, and —C(O)R$^i$.

In a class of this embodiment, R$^g$ is methyl or —C(O)R$^i$.

In one class of this embodiment, R$^g$ is methyl.

In yet another embodiment of the present invention, each R$^h$ is independently selected from: halogen, C$_{1-10}$alkyl, —O—C$_{1-4}$alkyl, —S—C$_{1-4}$alkyl, —CN, —NO$_2$, —CF$_3$, and —OCF$_3$.

In a class of this embodiment, each R$^h$ is independently selected from: halogen, C$_{1-3}$alkyl, —O—C$_{1-3}$alkyl, —S—CH$_3$, —CN, —CF$_3$, and —OCF$_3$.

In another embodiment of the present invention, each R$^i$ is independently selected from: hydrogen, C$_{1-10}$alkyl, C$_{2-10}$alkenyl, cycloalkyl, cycloalkyl-C$_{1-10}$alkyl, cycloheteroalkyl, cycloheteroalkyl-C$_{1-10}$alkyl, aryl, heteroaryl, aryl-C$_{1-10}$alkyl, and heteroaryl-C$_{1-10}$alkyl.

In one class of this embodiment, each R$^i$ is independently selected from: hydrogen, C$_{1-6}$alkyl, cycloalkyl, cycloalkyl-C$_{1-3}$alkyl, cycloheteroalkyl, cycloheteroalkyl-C$_{1-3}$alkyl, aryl, heteroaryl, aryl-C$_{1-3}$alkyl, and heteroaryl-C$_{1-3}$alkyl.

In one subclass of this class, each R$^i$ is independently selected from: hydrogen and methyl.

In one embodiment of the present invention, m is selected from 1 and 2. In one class this embodiment, m is 2. In another class, m is 1.

Another embodiment of the present invention is directed to compounds of general formula II:

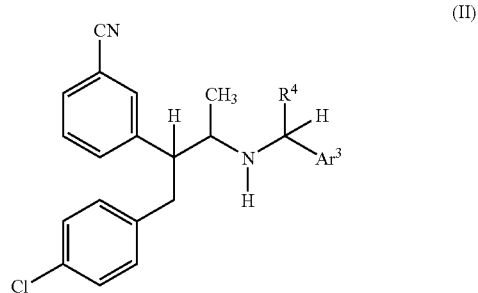

(II)

stereoisomers and pharmaceutically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each having from 3 to 10 carbon atoms. Examples of cycloalkyl include cyclopropyl, cyclobutyl, cyclopentyl, cyclohexyl, cycloheptyl, cyclooxtyl, tetrahydronaphthyl, decahydronaphthyl, and the like.

"Aryl" means mono- or bicyclic aromatic rings containing only carbon atoms. Examples of aryl include phenyl, naphthyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thiophenyl, pyrimidyl, pyridazinyl, pyrazinyl, benzoxazolyl, benzothiazolyl, benzimidazolyl, benzofuranyl, benzothiophenyl, benzothiazolyl, benzotriazolyl, benzoisoxazolyl, furo(2,3-b)pyridyl, quinolyl, indolyl, isoquinolyl, indolinyl, oxazolidinyl, and the like. The heteroaryl ring may be substituted on one or more carbon atoms. In one embodiment of the present invention, heteroaryl is pyridinyl, imidazolyl, and thienyl.

"Cycloheteroalkyl" means mono- or bicyclic or bridged saturated rings containing at least one heteroatom selected from N, S and O, each of said ring having from 3 to 10 atoms in which the point of attachment may be carbon or nitrogen. Examples of "cycloheteroalkyl" include pyrrolidinyl, piperidinyl, piperazinyl, imidazolidinyl, pyranyl, tetrahydrofuranyl, 2,3-dihydro-1H-indolyl, morpholinyl, dioxanyl, oxanyl, azetidinyl, perhydroazepinyl, tetrahydrofuranyl, 1-thia-4-aza-cyclohexane (thiomorpholinyl), hexahydrothienopyridinyl, thienopyridinyl, azacycloheptyl, 3,4-dihydroquinolinyl, 1H-indazolyl, 1H-indolyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The cycloheteroalkyl ring may be substituted on the ring carbons and/or the ring nitrogens.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

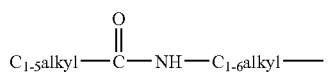

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases can be chosen from aluminum, ammonium, calcium, copper, ferric, ferrous, lithium, magnesium, manganic salts, manganous, potassium, sodium, zinc, and the like, such as for example, ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor and mimics the effects of the endogenous regulatory compound, such as contraction, relaxation, secretion, change in enzyme activity, etc. An "antagonist" is a compound, devoid of intrinsic regulatory activity, which produces effects by interfering with the binding of the endogenous agonist or inhibiting the action of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, such as for example, to opiates, alcohol, marijuana, and nicotine. The compounds are also useful for the treatment of obesity or eating disorders associated with excessive food intake and complications associated therewith, including left ventricular hypertrophy. The compounds are also useful for the treatment of constipation and chronic intestinal pseudo-obstruction. The compounds are also useful for the treatment of cirrhosis of the liver. The compounds are also useful for the treatment of asthma.

The present invention is also directed to a method of treating a disease mediated by the cannabinoid-1 receptor comprising administration to a patient in need of such treatment of a therapeutically effective amount of a compound of structural formula I. One embodiment of the present invention is directed to a method of treating a disease mediated by the cannabinoid-1 receptor comprising administration to a patient in need of such treatment of a therapeutically effective amount of a compound of structural formula I, wherein the disease mediated by the cannabinoid-1 receptor is selected from: psychosis, memory deficit, cognitive disorders, migraine, neuropathy, neuro-inflammatory disorders, cerebral vascular accidents, head trauma, anxiety disorders, stress, epilepsy, Parkinson's disease, schizophrenia, substance abuse disorders, constipation, chronic intestinal pseudo-obstruction, cirrhosis of the liver, asthma, obesity, and other eating disorders associated with excessive food intake. In one class of this embodiment, the disease mediated by the cannabinoid-1 receptor is selected from obesity, bulimia nervosa, and compulsive eating disorders. In one subclass of this class, the eating disorder associated with excessive food intake is obesity.

In another aspect, the present invention is directed to a method of preventing obesity in a person at risk for obesity comprising administration to said person of about 0.001 mg to about 100 mg per kg of a compound of the present invention.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the guinea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of pediatric chronic intestinal pseudo-obstruction and animal models related to the neuropathology of pediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lies within the range of from about 0.001 mg to about 100 mg per kg body weight of a mammal, in one embodiment, the ranges is from 0.01 mg to about 50 mg per kg, and in another embodiment, the range is from 0.1 to 10 mg per kg, each of which may be administered in single or divided doses. On the other hand, it may be necessary to use dosages outside these limits in some cases.

For use where a composition for intravenous administration is employed, a suitable dosage range is from about 0.001 mg to about 100 mg in one embodiment from 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day, in one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

Ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or companion animal such as a dog or cat, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. To be administered in the form of a transdermal delivery system, the dosage administration will, of course, be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet, capsule or sachet contains from 0.01 to 1,000 mg, particularly 0.01, 0.05, 0.1, 0.5, 1, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated. Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-epileptics, anorectic agents, serotonin reuptake inhibitors, and other anti-obesity agents, as well as antidiabetic agents, lipid lowering agents, and antihypertensive agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents. The present invention thus provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, piclorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, piclorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

The present invention also provides a method for the treatment or prevention of obesity, which method comprises administration to a patient in need of such treatment an amount of a compound of the present invention and an amount of another agent useful in treating obesity and obesity-related conditions, such that together they give effective relief.

Suitable agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone; rosiglitazone; troglitazone; BRL49653; CLX-0921; 5-BTZD, and GW-0207, LG-100641, and LY-300512, and the like and compounds disclosed in WO97/10813, 97/27857, 97/28115, 97/28137, 97/27847, 03/000685, 03/027112, 03/035602, 03/048130, 03/055867, and the like; (2) biguanides such as buformin; metformin; and phenformin, and the like; (3) protein tyrosine phosphatase-1B (PTP-1B) inhibitors, such as ISIS 113715, and those disclosed in WO 03/032916, WO 03/032982, WO 03/041729, WO 03/055883; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride; and A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$), and the like; (12) non-thiazolidinediones such as JT-501, and farglitazar (GW-2570/GI-262579), and the like; (13) PPARα/γ dual agonists such as BVT-142, CLX-0940, GW-1536, GW1929, GW-2433, KRP-297, L-796449, LR-90, MK-0767, SB 219994, and reglitazar (JTT-501) and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/004458, WO 03/016265, WO 03/018010, WO 03/033481, WO 03/033450, WO 03/033453, WO 03/043985, WO 03/053976; (14) other insulin sensitizing drugs; (15) VPAC2 receptor agonists; (16) GLK modulators, such as those disclosed in WO 03/015774; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine and those compounds disclosed in WO 03/024447, WO 03/037869, WO 03/037877, WO 03/037891, WO 03/068773, EP 1295884, EP 1295885, and the like; (19) glycogen phosphorylase (HGLPa) inhibitors, such as those disclosed in WO 03/037864; (20) ATP consumption promotors such as those disclosed in WO 03/007990; (21) TRB3 inhibitors, (22) vanilloid receptor ligands such as those disclosed in WO 03/049702, (23) hypoglycemic agents such as those disclosed in WO 03/015781, WO 03/040114, (24) glycogen synthase kinase 3 inhibitors such as those disclosed in WO 03/035663, (25) and agents such as those disclosed in WO 99/51225 and US 20030134890; and WO 01/24786, WO 03/059870; (26) Insulin-responsive DNA binding protein-1 (IRDBP-1) as disclosed in WO 03/057827, and the like; (27) Adenosine A2 antagonists such as those disclosed in WO 03/035639, WO 03/035640, and the like; and (b) lipid lowering agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, fluvastatin, lovastatin, pravastatin, rivastatin, rosuvastatin, simvastatin, and ZD-4522, particularly simvastatin, and the like and compounds disclosed in WO 03/033481; (3) HMG-CoA synthase inhibitors; (4) cholesterol absorption inhibitors such as stanol esters, beta-sitosterol, sterol glycosides such as tiqueside; and azetidinones such as ezetimibe, and the like; (5) acyl coenzyme A-cholesterol acyl transferase (ACAT) inhibitors such as avasimibe, eflucimibe, KY505, SMP 797, and the like; (6) CETP inhibitors such as JTT 705, torcetrapib, CP 532,632, BAY63-2149, SC 591, SC 795, and the like; (7) squalene synthetase inhibitors; (8) anti-oxidants such as probucol, and the like; (9) PPARα agonists such as beclofibrate, benzafibrate, ciprofibrate, clofibrate, etofibrate, fenofibrate, gemcabene, and gemfibrozil, GW 7647, BM 170744, LY518674; and other fibric acid derivatives, such as Atromid®, Lopid® and Tricor®, and those disclosed in WO 03033456, WO 03/033481, WO 03/043997, WO 03/048116, WO 03/053974, WO 03/059864, WO 03/05875, and the like; (10) FXR receptor modulators such as GW 4064, SR 103912, and the like; (11) LXR receptor modulators such as GW 3965, T9013137, and XTCO179628, and those disclosed in US 20030125357, WO 03/045382, WO 03/053352, WO 03/059874, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; (16) PPARδ agonists such as GW 501516, and GW 590735, and the like, such as those disclosed in WO97/28149, WO 01/79197, WO 02/14291, WO 02/46154, WO 02/46176, WO 02/076957, WO 03/016291, WO 03/033493; (17) triglyceride synthesis inhibitors; (18) microsomal triglyceride transport (MTTP) inhibitors, such as inplitapide, LAB687, and CP346086, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists; (25) PPAR modulators such as those disclosed in WO 99/07357, WO 99/11255, WO 9912534, WO 99/15520, WO 99/46232, WO 00/12491, WO 00/23442, WO 00/236331, WO 00/236332, WO 00/218355, WO 00/238553, WO 01/25181, WO 01/79150, WO 02/79162, WO 02/100403, WO 02/102780, WO 02/081428, WO 03/016265, WO 03/033453, WO 03/042194, WO 03/043997, WO 03/066581, and the like; (26) niacin-bound chromium, as disclosed in WO 03/039535; (27) substituted acid derivatives disclosed in WO 03/040114; (28) apolipoprotein B inhibitors such as those disclosed in WO 02/090347, WO 02/28835, WO 03/045921, WO 03/047575; (29) Factor Xa modulators such as those disclosed in WO 03/047517, WO 03/047520, WO 03/048081, and the like; and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine, tizanidine, and guanobenz, and the like; and (12) aldosterone inhibitors, and the like; (13) angiopoietin-2 binding agents such as those disclosed in WO 03/030833, and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663; (2) NE (norepinephrine) transporter inhibitors, such as GW 320659, despiramine, talsupram, and nomifensine; (3) CB1 (cannabinoid-1 receptor) antagonist/inverse agonists, such as rimonabant (Sanofi Synthelabo), SR-147778 (Sanofi Synthelabo), BAY 65-2520 (Bayer), and SLV 319 (Solvay), and those disclosed in U.S. Pat. Nos. 4,973,587, 5,013,837, 5,081,122, 5,112,820, 5,292,736, 5,532,237, 5,624,941, 6,028,084, and 6,509,367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 03/042174, WO 03/51850, WO 03/051851, WO 03/063781, WO03/077847, WO 03/086940, WO 03/084943; and U.S. Pat. No. 6,509,367, EPO No. EP-658546; (4) ghrelin antagonists, such as those disclosed in WO 01/87335, and WO 02/08250; (5) H3 (histamine H3) antagonist/inverse agonists, such as thioperamide, 3-(1H-imidazol-4-yl)propyl N-(4-pentenyl) carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in US 2003/0134835, U.S. Pat. No. 6,316,475, WO 02/074758, WO 02/40461, WO 03/024928, WO 03/024929, WO 03/031432, WO 03/044059, WO 03/059341, WO 03/066604; (6) melanin-concentrating hormone 1 receptor (MCH1R) antagonists, such as T-226296 (Takeda), SNP-7941 (Synaptic), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 03/35055, WO 03/035624, WO 03/045313, WO 03/045920, WO 03/047568, WO 03/045918, WO 03/059289, WO 03/060475; U.S. Pat. No. 6,569,861, and Japanese Patent Application Nos. JP 13226269, and JP 1437059; (7) MCH2R (melanin concentrating hormone 2R) agonist/antagonists; (8) NPY1 (neuropeptide Y Y1) antagonists, such as BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/23389, WO 01/85690, WO 01/85098, WO 01/85173, WO 01/89528, WO 03/062209, and the like; (9) NPY5 (neuropeptide Y Y5) antagonists, such as 152,804, GW-569180A, GW-594884A, GW-587081X, GW-548118X; FR 235,208; FR226928, FR 240662, FR252384; 1229U91, GI-264879A, CGP71683A, LY-377897, LY366377, PD-160170, SR-120562A, SR-120819A, JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; European Patent Nos. EP-01010691, EP-01044970, EP 1306085; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 03/059905, WO 03/066055; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509, WO 03/064375; (13) orexin antagonists, such as SB-334867-A; and those disclosed in WO 99/09024, WO 99/58533, WO 01/96302, WO 01/68609, WO 02/44172, WO 02/51232, WO 02/51838, WO 02/089800, WO 02/090355, WO 03/023561, WO 03/032991, WO 03/037847, WO 03/041711; (14) BRS3 (bombesin receptor subtype 3) agonists; (15) CCK-A (cholecystokinin-A) agonists, such as AR-R 15849, GI 181771, JMV-180, A-71378, A-71623 and SR146131, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170, 292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358, 951, U.S. Patent Application Nos. 2002/049196 and 2002/022637; and WO 01/56592, and WO 02/32888; (19) 5HT2c (serotonin receptor 2c) modulators, such as BVT933, DPCA37215, IK264; PNU 22394; WAY161503, R-1065, and YM 348; and those disclosed in U.S. Pat. No. 3,914,250; and WO 01/66548, WO 02/10169, WO 02/36596, WO 02/40456, and WO 02/40457. WO 02144152, WO 02/48124, WO 02/51844, WO 03/033479, WO 03/057161, WO 03/057213, WO 03/057673, WO 03/057674, WO 03/0153576, and the like; (20) Mc3r (melanocortin 3 receptor) agonists; (21) Mc4r (melanocortin 4 receptor) agonists, such as CHIR86036 (Chiron); ME-10142, ME-10145, and HS-131 (Melacure), and those disclosed in WO 99/64002, WO 00/74679, WO 01/991752, WO 01/0125192, WO 01/52880, WO 01/74844, WO 01/70708, WO 01/70337, WO 01/91752, WO 02/059095, WO 02/059107, WO 02/059108, WO 02/059117, WO 02/06276, WO 02/12166, WO 02/11715, WO 02112178, WO 02/15909, WO 02/18327, WO 02/38544, WO 02/068387, WO 02/068388, WO 02/067869, WO 02/081430, WO 03/06604, WO 03/007949, WO 03/009847, WO 03/009850, WO 03/013509, WO 03/031410, WO 03/040117, WO 03/040118, WO 03/053927, WO 03/057671, WO 03/061660, WO 03/066597, and the like; (22) monoamine reuptake inhibitors, such as sibutramine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors, such as those disclosed in WO 02/02101, WO 03/057255, WO 03/059871, and the like; (28) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, N-5984 (Nisshin Kyorin), LY-377604 (Lilly), and SR 59119A, and those disclosed in U.S. Pat. No. 5,705,515, U.S. Pat. No. 5,451,677; and WO94/18161, WO95/29159, WO97/46556, WO98/04526 and WO98/32753, WO 01/74782, WO 02/32897, WO 03/014113, WO 03/016276, WO 03/016307, WO 03/024948, WO 03/024953, WO 03/035620, WO 03/037881, WO 03/0946, WO 03/044016, WO 03/044017, WO 03/059348; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid antagonists; (37) 11β HSD-1 (11-beta hydroxy steroid dehydrogenase type 1) inhibitors, such as BVT 3498, BVT 2733, 3-(1-adamantyl)-4-ethyl-5-ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, WO 01/90090, WO 01/90092, WO 02/072084, WO 03/043999, WO 03/044000, WO 03/044009, WO 03/065983, and the like; (38) SCD-1 (stearoyl-CoA desaturase-1) inhibitors; (39) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274444; and the compounds disclosed in WO 01/35988, WO 01/62266, WO 02/083128, WO 02/062764, WO 03/000180, WO 03/000181, WO 03/000250, WO 03/002530, WO 03/002531, WO 03/002553, WO 03/002593, WO 03/004498, WO 03/004496, WO 03/017936, WO 03/024942, WO 03/024965, WO 03/033524, WO 03/035057, WO 03/03567, WO 03/037327, WO 03/055881, WO 03/057144, WO 03/057200, WO 03/057666, WO 03/068748, WO 03/06757, and EP 1 258 476; (40) lipase inhibitors, such as tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, ATL-962, and RHC 80267, and those disclosed in WO 01/77094, and U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749; WO 01/32638, WO 01/62746, WO 01/62747, and WO 03/015769; (46) peptide YY and PYY agonists such as those disclosed in WO 03/026591, including PYY3-36; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, (50) appetite suppressants such as those disclosed in WO 03/040107, (51) 5HT 6 receptor modulators, such as those disclosed in WO 03/030901, WO 03/035061, WO 03/039547, and the like; (52) 5HT1a modulators such as those disclosed in WO 03/031439, and the like; (53) mGluR5 modulators such as those disclosed in WO 03/029210, WO 03/047581, WO 03/048137, WO 03/051315, WO 03/051833, WO 03/053922, WO 03/059904, and the like; (54) 5HT antagonists such as those disclosed in WO 03/037871, WO 03/037887, and the like; (55) fat resporption inhibitors such as those disclosed in WO 03/053451, and the like; (56) interleukin-6 (IL-6) and modulators thereof as disclosed in WO 03/057237, and the like; (57) cyclooxygenase-2 (COX-2) inhibitors such as celecoxib, etoricoxib, valdecoxib, and COX-189, and the like.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1 (3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

Specific DP-IV inhibitors of use in combination with a compound of the present invention are selected from:

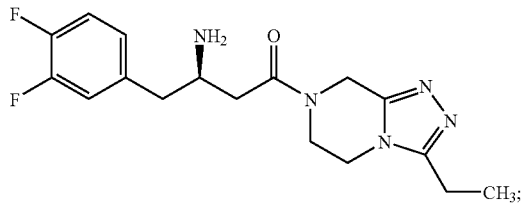

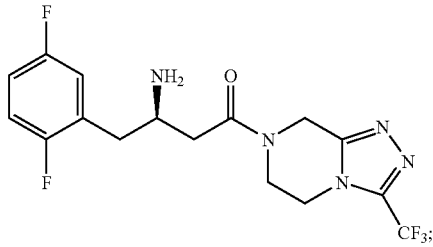

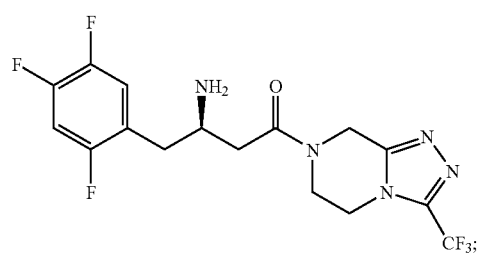

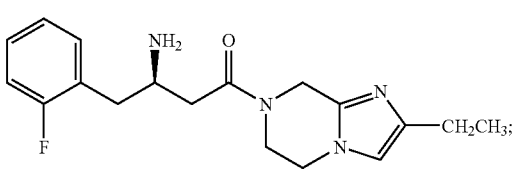

-continued

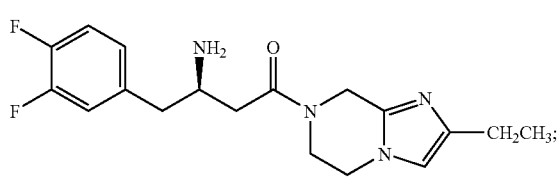

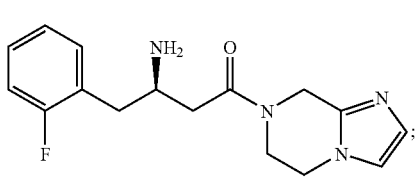

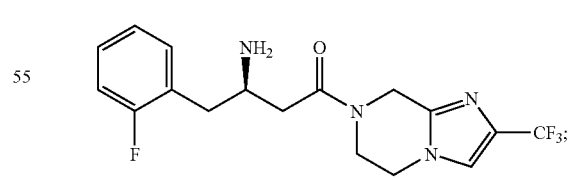

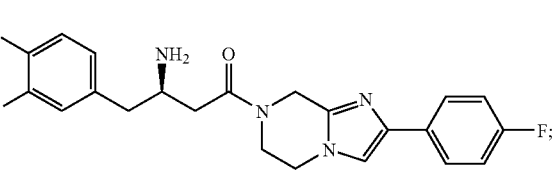

-continued
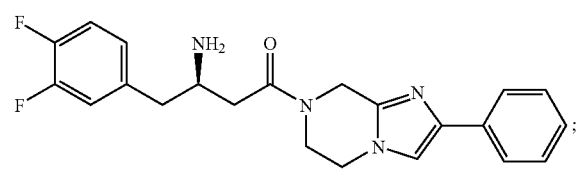
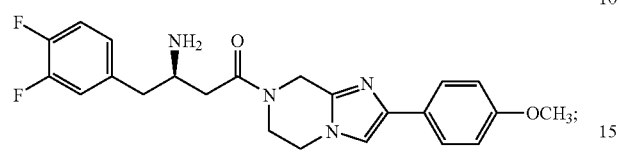
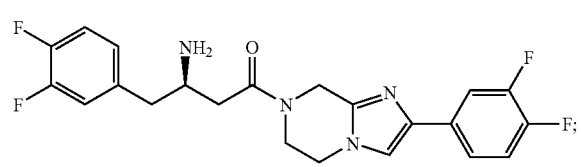
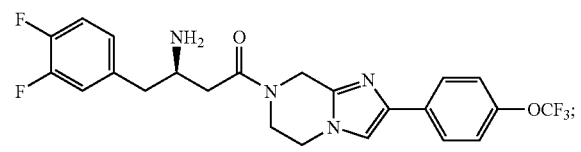
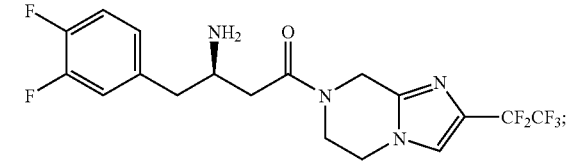
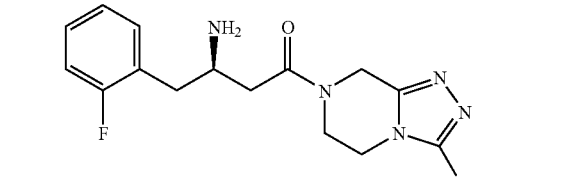
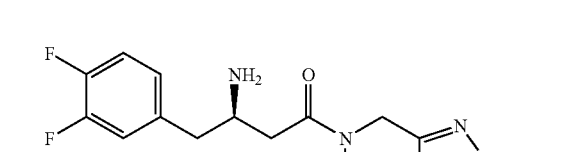
-continued
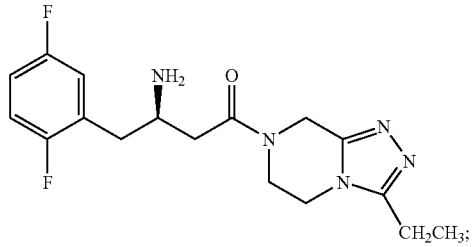
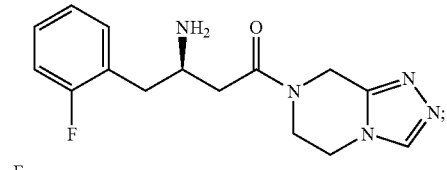
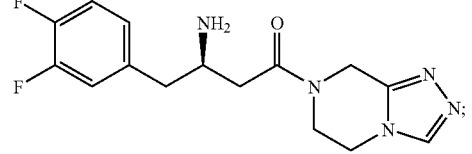
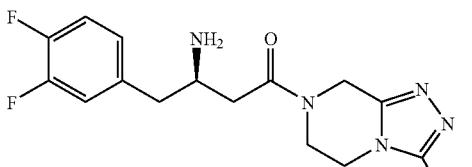
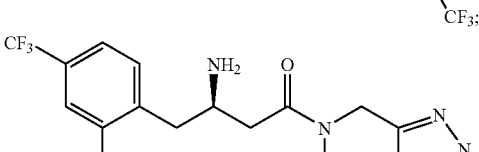
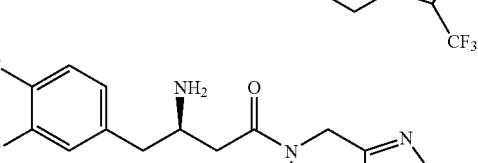
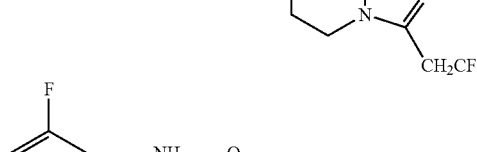
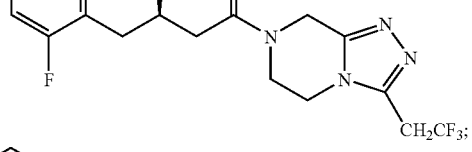
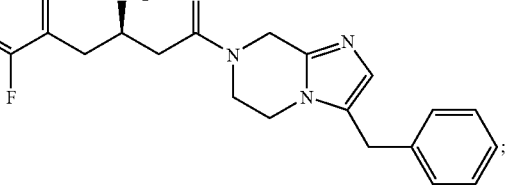

-continued

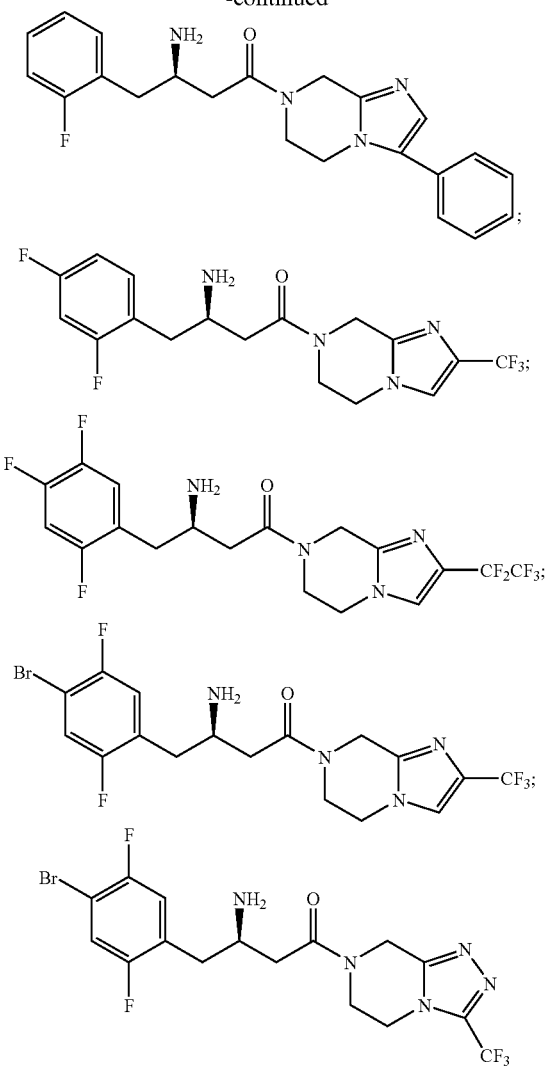

and pharmaceutically acceptable salts thereof.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asian countries, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "diabetes," as used herein, includes both insulin-dependent diabetes mellitus (IDDM, also known as type I diabetes) and non-insulin-dependent diabetes mellitus (NIDDM, also known as Type II diabetes.) Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RDAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, imipramine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and those disclosed in WO 03/037905, and pharmaceutically acceptable salts thereof.

Suitable CRF antagonists include those compounds described in International Patent Specification Nos. WO 94/13643, WO 94/13644, WO 94/13661, WO 94/13676 and WO 94/13677. Still further, neurokinin-1 (NK-1) receptor antagonists may be favorably employed with the CB1 receptor modulators of the present invention. NK-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438-98/24441, 98/24442-98/24445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific NK-1 receptor antagonists of use in the present invention include: (±)-2R3R,2S3S)—N-{[2-cyclopropoxy-5-(trifluoromethoxy)-phenyl]methyl}-2-phenylpiperidin-3-amine; 2-(R)-1-(R)-3,5-bis(trifluoromethyl)phenyl)ethoxy)-3-(S)-(4-fluorophenyl)-4-(3-(5-oxo-1H,4H-1,2,4-triazolo) methyl)morpholine; aperpitant; CJ17493; GW597599; GW679769; R673; RO67319; R1124; R1204; SSR-146977; SSR240600; T-2328; and T2763; or a pharmaceutically acceptable salt thereof.

Suitable atypical anti-depressants include: bupropion, lithium, nefazodone, trazodone and vii oxazine, and pharmaceutically acceptable salts thereof. Suitable classes of anti-anxiety agents include benzodiazepines and 5-HT$_{1A}$ agonists or antagonists, especially 5-HT$_{1A}$ partial agonists, and corticotropin releasing factor (CRF) antagonists. Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof. Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

In particular, compounds of structural formula I are useful for aiding in stopping consumption of tobacco and are useful in treating nicotine dependence and nicotine withdrawal. The compounds of formula I produce in consumers of nicotine, such as tobacco smokers, a total or partial abstinence from smoking. Further, withdrawal symptoms are lessened and the weight gain that generally accompanies quitting tobacco consumption is reduced or nonexistent. For smoking cessation, the compound of form I may be used in combination with a nicotine agonist or a partial nicotine agonist, or a monoamine oxidase inhibitor (MAOI), or another active ingredient demonstrating-efficacy in aiding cessation of tobacco consumption; for example, an antidepressant such as bupropion, doxepine, ornortriptyline; or an anxiolytic such as buspirone or clonidine.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the $5-HT_{2A}$ receptor antagonists, examples of which include MDL100907, SB-247853 and fananserin. Also of use in combination with a CB1 receptor modulator are the serotonin dopamine antagonists (SDAs) which are believed to combine $5-HT_{2A}$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described previously.

It will be appreciated that a combination of a conventional anti-asthmatic drug with a CB1 receptor modulator may provide an enhanced effect in the treatment or prevention of asthma and may be used for the manufacture of a medicament for the treatment or prevention of asthma.

The present invention also provides a method for the treatment or prevention of asthma, comprising administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); and (f) antagonists of the chemokine receptors, especially CCR-3, such as those disclosed in WO 03/068759, and the like; and pharmaceutically acceptable salts thereof.

It will be appreciated that a combination of a conventional anti-constipation drug with a CB1 receptor modulator may provide an enhanced effect in the treatment or prevention of constipation or chronic intestinal pseudo-obstruction, and for use for the manufacture of a medicament for the treatment or prevention of constipation or chronic intestinal pseudo-obstruction.

The present invention also provides a method for the treatment or prevention of constipation or chronic intestinal pseudo-obstruction, comprising administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof. A particularly suitable class of osmotic agents include, but are not limited to sorbitol, lactulose, polyethylene glycol, magnesium, phosphate, and sulfate; and pharmaceutically acceptable salts thereof. A particularly suitable class of laxatives and detergent laxatives, include, but are not limited to, magnesium, and docusate sodium; and pharmaceutically acceptable salts thereof. A particularly suitable class of bulking agents include, but are not limited to, psyllium, methylcellulose, and calcium polycarbophil; and pharmaceutically acceptable salts thereof. A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment or prevention of cirrhosis of the liver, and for use for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples: Ac=acetyl; aq.=aqueous; API-ES=atmospheric pressure ionization-electrospray; Boc=tert-butyloxy carbonyl; Calc'd=calculated; DEAD=diethyl azodicarboxylate; DMAP=4-dimethylamino-pyridine; DMF=dimethylformamide; DMSO=dimethylsulfoxide; EDC=1-ethyl-3-(3-dimethylamino-propyl)-carbodiimide hydrochloride; EPA=ethylene polyacrylamide (a plastic); Et=ethyl; g=gram; h=hours; Hex=hexane; HOBt=1-hydroxybenzotriazole; HPLC=high pressure liquid chromatography; HPLC/MS=high pressure liquid chromatography/mass spectrum; in vacuo=rotoevaporation; IPAC or IPAc=isopropyl acetate; KHMDS=potassium hexamethyldisilazide; LAH=lithium aluminum hydride; LC=Liquid chromatography; LC/MS, LC-MS=liquid chromatography-mass spectrum; LDA=lithium diisopropyl amide; M=molar; Me=methyl; MHz=megahertz; min=minute; mL=milliliter; mmol=millimole; MS or ms=mass spectrum; Ms=methanesulfonyl, mesyl; N=normal; NaHMDS=sodium hexamethyldisilazide; NMR=nuclear magnetic resonance; PyBOP=(benzotriazol-1-yloxy)tripyrrolidinophosphonium hexafluorophosphate; Rt=retention time; rt or RT=room temperature; TFA=trifluoroacetic acid; THF=tetrahydrofuran; TLC=thin layer chromatography; TMS=trimethylsilyl.

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substitutents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

Scheme 1

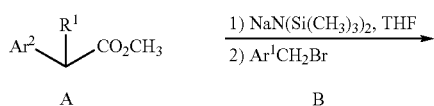

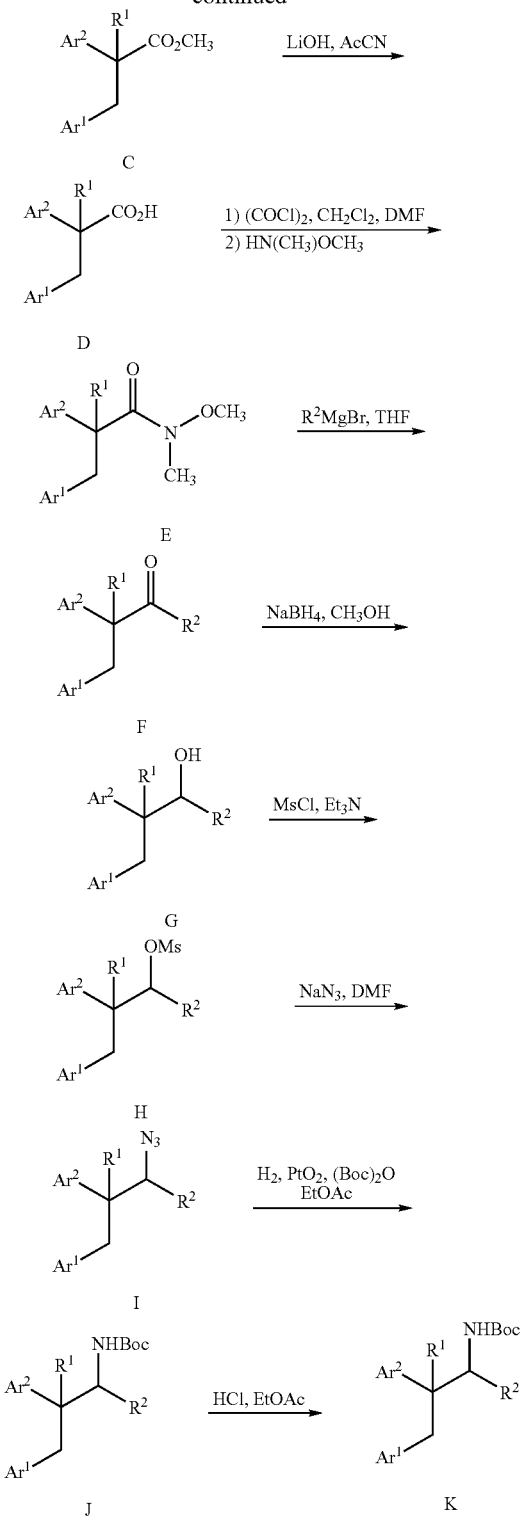

In Scheme 1, an arylacetate derivative A is alkylated with an arylhalide B to afford the a-substituted arylacetate C. The ester in C is hydrolyzed by hydroxide, the resultant acid D is converted to the corresponding acylchloride, and reacted with N,O-dimethylhydroxylamine to afford the Weinreb amide E. Reaction with a Grignard reagent will yield ketone F. The carbonyl in F is reduced with borohydride to yield alcohol G. Reaction of G with methanesulfonyl chloride affords the mesylate H which is reacted with sodium azide to form I. Reduction of I in the presence of hydrogen gas, a metal catalyst, and Boc-anhydride affords the acylated amine J. The azide I was reduced in the presence of Boc-anhydride to facilitate purification. The Boc group is conveniently removed in the presence of strong acid to yield amine K.

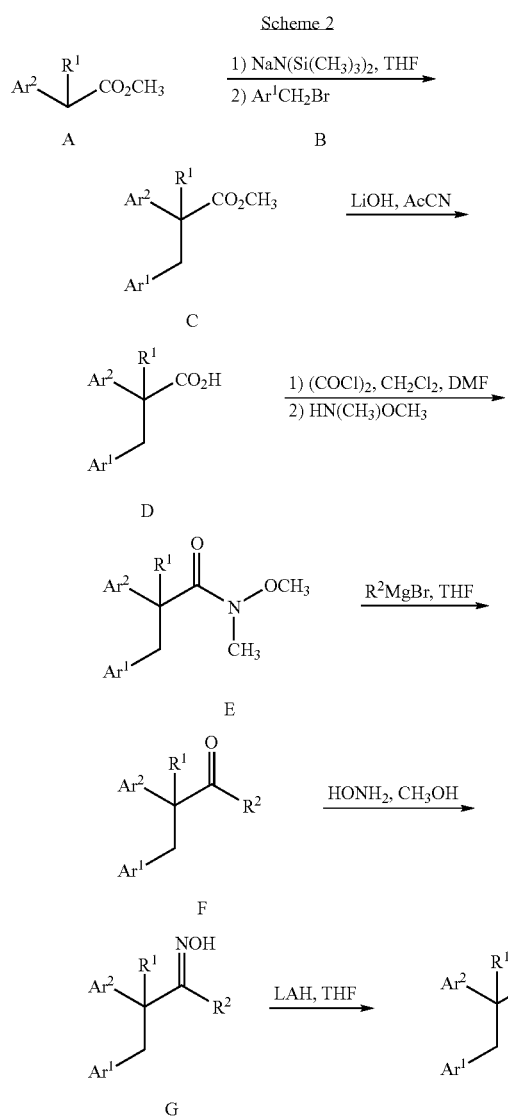

In Scheme 2, the ketone F is prepared from arylacetate A in a manner similar to that described in Scheme 1. The ketone F is reacted with hydroxylamine to form oxime G which is reduced with lithium aluminum hydride to yield amine H.

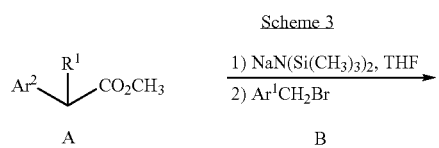

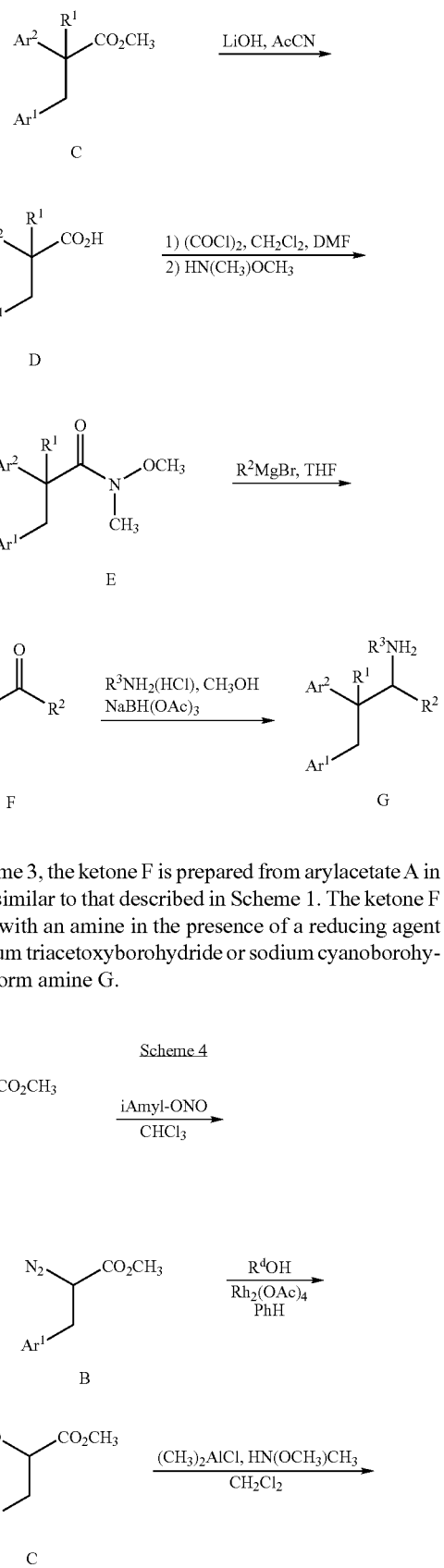

In Scheme 3, the ketone F is prepared from arylacetate A in a manner similar to that described in Scheme 1. The ketone F is reacted with an amine in the presence of a reducing agent (e.g., sodium triacetoxyborohydride or sodium cyanoborohydride) to form amine G.

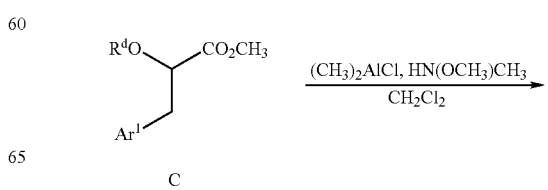

-continued

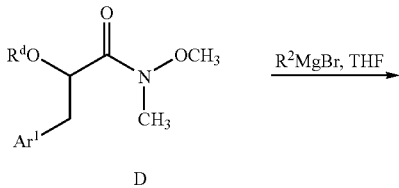

D

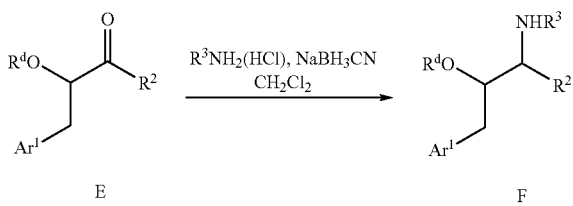

E → F

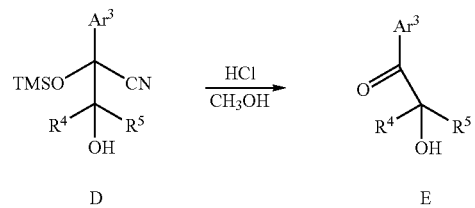

D → E

Scheme 5 outlines the synthesis of aryl ketone derivatives that are useful for the preparation of compounds of the present invention. An arylaldehyde A is treated with trimethylsilyl-cyanide to form O-silyl cyanohydrin B. Treatment of B with strong base (e.g., lithium diisopropylamide) followed by reaction with a ketone or aldehyde C forms cyanohydrin alcohol D. Treatment of D with strong acid hydrolyzes the cyanohydrin to afford keto-alcohol E.

Scheme 6

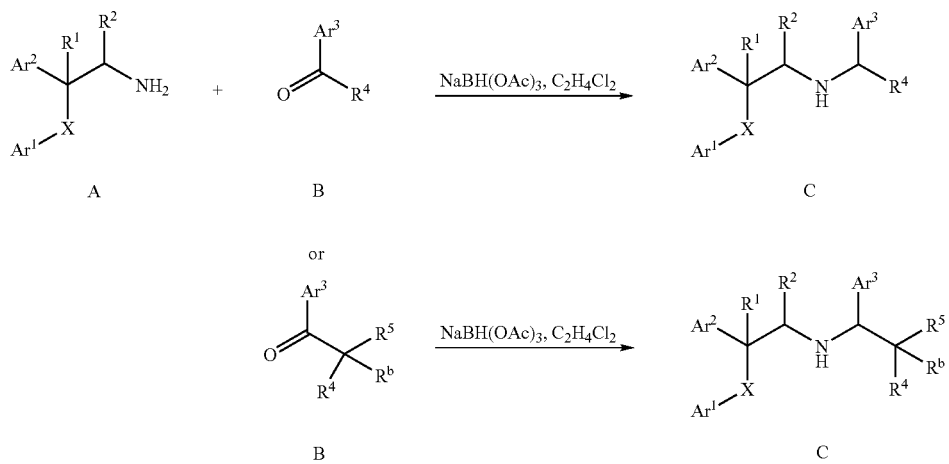

In Scheme 4, aryl amino acid ester A is treated with isoamylnitrite to afford diazo ester B which is reacted with an alcohol in the presence of rhodium acetate to afford ether ester C. The ester in C is reacted with N,O-dimethylhydroxlamine in the presence of dimethylaluminum chloride to yield Weinreb amide D. Reaction of D with a Grignard reagent will afford ketone E. Reaction of ketone E with an amine in the presence of sodium cyanoborohydride affords the amine F.

Scheme 5

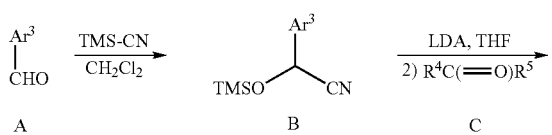

The preparation of compounds of the current invention are outlined in Scheme 6. Substituted amine derivative A is reacted with aryl ketone derivative B in the presence of a reducing agent to afford substituted amine derivative C.

To illustrate the invention, the following examples are included. These examples do not limit the invention. They are only meant to suggest a method of reducing the invention to practice. Those skilled in the art may find other methods of practicing the invention which are readily apparent to them. Those methods are also deemed to be within the scope of this invention.

General Procedures.

The LC/MS analyses were preformed using a MICROMASS ZMD mass spectrometer coupled to an AGILENT 1100 Series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMR spectra were obtained on a 500 MHz VARIAN Spectrometer in $CDCl_3$ or $CD_3OD$ as indicated and chemical shifts are reported as δ using the solvent peak as reference and coupling constants are reported in hertz (Hz).

REFERENCE EXAMPLE 1

N-[2,3-Bis(4-chlorophenyl)-1-methylpropyl]-amine hydrochloride

The preparation of the two diastereomers (alpha and beta) of N-[2,3-bis(4-chlorophenyl)-1-methylpropyl]-amine hydrochloride salt has been disclosed (Schultz, E. M, et al. *J. Med Chem.* 1967, 10, 717). Diastereomer α: LC-MS: calc'd for $C_{16}H_{17}Cl_2N$ 293, obs'd m/e 294 $(M+H)^+$ ($R_t$ 2.5 min). Diastereomer β: LC-MS: calc'd for $C_{16}H_{17}Cl_2N$ 293, obs'd m/e 294 $(M+H)^+$ ($R_t$ 2.2 min).

The amines of Reference Examples 2-9 were prepared by the same procedures described in Reference Example 1:

REFERENCE EXAMPLE 10

N-[3-(4-Chlorophenyl)-2-phenyl-1-methylpropyl]-amine hydrochloride (Diastereomer α)

Step A 3-(4-Chlorophenyl)-2-phenylpropanoic acid, methyl ester

To a solution of methyl phenylacetate (12 g, 80 mmol) and 4-chlorobenzyl bromide (16 g, 80 mmol) in 250 mL anhydrous THF at −78° C. was added sodium hexamethyldisilazide (1 M in THF, 80 mL, 80 mmol) (potassium hexamethyldisilazide in toluene may be used with similar results). The reaction was allowed to warm to room temperature overnight. The volatile materials were removed on a rotary evaporator, and the resulting mixture was partitioned between saturated

| Reference Example | Name | LC/MS |
|---|---|---|
| 2 | 2-Amino-3,4-diphenylbutane hydrochloride salt | Diastereomer α:<br>LC-MS: calc'd $C_{16}H_{19}N$ 225, obs'd m/e 226 $(M + H)^+$ (2.0 min).<br>Diastereomer β:<br>LC-MS: calc'd for $C_{16}H_{19}N$ 225, obs'd m/e 226 $(M + H)^+$ (1.9 min). |
| 3 | 3-Amino-1,2-diphenylpentane hydrochloride salt | Diastereomer α:<br>LC-MS: calc'd for $C_{17}H_{21}N$ 239, observed m/e 240 $(M + H)^+$ (2.1 min).<br>Diastereomer β:<br>LC-MS: calc'd for $C_{17}H_{21}N$ 239, observed m/e 240 $(M + H)^+$ (2.0 min). |
| 4 | 1-Amino-1,2,3-triphenylpropane p-toluenesulfonate salt | Diastereomer α:<br>LC-MS: calc'd for $C_{21}H_{21}N$ 287, observed m/e 288 $(M + H)^+$ (2.3 min).<br>Diastereomer β:<br>LC-MS: calc'd for $C_{21}H_{21}N$ 287, observed m/e 288 $(M + H)^+$ (2.3 min). |
| 5 | 2-Amino-4-(4-chlorophenyl)-3-phenylbutane hydrochloride salt | Diastereomer α:<br>LC-MS: calc'd for $C_{16}H_{18}ClN$ 259, observed m/e 260 $(M + H)^+$ (2.3 min).<br>Diastereomer β:<br>LC-MS: calc'd for $C_{16}H_{18}ClN$ 259, observed m/e 260 $(M + H)^+$ (2.2 min). |
| 6 | 2-Amino-3-(4-chlorophenyl)-4-phenylbutane hydrochloride salt | Diastereomer α:<br>LC-MS: calc'd for $C_{16}H_{18}ClN$ 259, observed m/e 260 $(M + H)^+$ (2.3 min).<br>Diastereomer β:<br>LC-MS: calc'd for $C_{16}H_{18}ClN$ 259, observed m/e 260 $(M + H)^+$ (2.1 min). |
| 7 | 2-Amino-4-(4-methoxycarbonylphenyl)-3-phenylbutane hydrochloride salt | Diastereomer α:<br>LC-MS: calc'd for $C_{18}H_{21}NO_2$ 283, observed m/e 284 $(M + H)^+$ (2.0 min).<br>Diastereomer β:<br>LC-MS: calc'd for $C_{18}H_{21}NO_2$ 283, observed m/e 284 $(M + H)^+$ (1.9 min). |
| 8 | 2-Amino-3-(2-Chlorophenyl)-4-phenylbutane (mixture of diastereomers α/β 1:2) | LC-MS: calc'd for $C_{16}H_{18}ClN$ 259, observed m/e 260 $(M + H)^+$ (1.9/2.0 min). |
| 9 | 2-Amino-3-(4-methoxyphenyl)-4-phenylbutane (mixture of diastereomers α/β 2:5) | LC-MS: m/e 256 $(M + H)^+$ (1.7 min). | ammonium chloride (200 mL) and EtOAc (200 mL). The organic layer was separated and the aqueous layer extracted with EtOAc (2×200 mL). The combined organic extracts were dried over anhydrous sodium sulfate, filtered, and concentrated to dryness to give the title compound. $^1$H NMR (500 MHz, CD$_3$OD): δ 7.36-7.10 (m, 9H), 3.81 (dd, 1H), 3.52 (s, 3H), 3.36 (dd, 1H), 3.02 (dd, 1H).

Step B 3-(4-Chlorophenyl)-2-phenylpropanoic acid

To a mixture of methyl 3-(4-chlorophenyl)-2-phenylpropionate (Step A, 20 g, 74 mmol) in acetonitrile (100 mL) and water (100 mL) was added lithium hydroxide monohydrate (8.8 g, 0.21 mol). After stirring at room temperature for 3 days, the volatile materials were removed by concentrating on a rotary evaporator and the residue was partitioned between water (300 mL) and hexane/ether (1:1, 200 mL). The water layer was separated, acidified to pH=2-3, and extracted with EtOAc (2×200 mL) The combined organic extracts were dried over anhydrous sodium sulfate, filtered, and concentrated to dryness to give the title compound. $^1$H NMR (500 MHz, CD$_3$OD): δ 7.34-7.10 (m, 9H), 3.82 (dd, 1H), 3.36 (dd, 1H), 2.98 (dd, 1H).

Step C N-Methoxy-N-methyl-3-(4-chlorophenyl)-2-phenylpropanamide

To a solution of 3-(4-chlorophenyl)-2-phenylpropionic acid (Step B, 14 g, 55 mmol) in CH$_2$Cl$_2$ (125 mL) at 0° C. was added dimethyl formamide (50 µL) and oxalyl chloride (14 g, 0.11 mol) dropwise. The reaction was allowed to warm to room temperature overnight and concentrated to dryness to give the crude acyl chloride, which was used without further purification. Thus, to a solution of the acyl chloride in CH$_2$Cl$_2$ (250 mL) was added N-methoxy-N-methylamine hydrochloride (11 g, 0.11 mol) and triethyl amine (dried over activated molecular sieves, 30 mL, 0.22 mol) at 0° C. After stirring at room temperature for 4 h, the reaction mixture was diluted with ether (500 mL) and successively washed with water, dilute aqueous sodium hydrogen sulfate and brine, dried over anhydrous MgSO$_4$, filtered and concentrated to dryness to give the crude product, which was used without further purification. $^1$H NMR (500 MHz, CD$_3$OD): δ 7.4-7.1 (m, 9H), 4.38 (br, 1H), 3.48 (s, 3H), 3.35 (dd, 1H), 3.10 (s, 3H), 2.92 (dd, 1H); LC-MS: m/e 304 (3.6 min).

Step D 4-(4-Chlorophenyl)-3-phenyl-2-butanone

To a solution of N-methoxy-N-methyl-3-(4-chlorophenyl)-2-phenylpropanamide (Step C, 16 g, 53 mmol, dried by azeotroping with toluene) in anhydrous THF (200 mL) at 0° C. was added methylmagnesium bromide (3 M in ether, 35 mL, 0.11 mol). After stirring at 0° C. for 2 h, the reaction was quenched with MeOH (5 mL) and 2 M hydrochloric acid (50 mL). The volatile materials were removed by concentrating on a rotary evaporator and the residue partitioned between saturated ammonium chloride (200 mL) and ether (200 mL). The organic layer was separated, and the aqueous layer was extracted with ether (2×200 mL). The combined organic extracts were dried over anhydrous MgSO$_4$, filtered and concentrated to dryness to give the title compound, which was used without further purification. $^1$H NMR (500 MHz, CD$_3$OD): δ 7.45-7.02 (m, 9H), 4.08 (dd, 1H), 3.34 (dd, 1H), 2.90 (dd, 1H), 2.03 (s, 3H).

Step E 4-(4-Chlorophenyl)-3-phenyl-2-butanol

To a solution of 4-(4-chlorophenyl)-3-phenyl-2-butanone (Step D, 13 g, 50 mmol) in MeOH (100 mL) at 0° C. was added sodium borohydride (3.8 g, 100 mmol). After stirring at 0° C. for 30 min, the reaction was quenched by addition of 2 M hydrochloric acid (50 mL). The volatile materials were removed by concentrating on a rotary evaporator and the residue partitioned between water (100 mL) and EtOAc (200 mL). The organic layer was separated and the aqueous layer extracted with EtOAc (2×200 mL). The combined organic extracts were washed with brine, dried over anhydrous sodium sulfate, filtered and concentrated to dryness to give the crude product, which was purified by flash column chromatography on silica gel eluted with 10% EtOAc in hexane to afford the pure faster eluting isomer and a mixture containing both the faster eluting isomer and the slower eluting isomer. Faster eluting isomer: $^1$H NMR (500 MHz, CD$_3$OD): δ 7.25-7.00 (m, 9H), 4.00 (m, 1H), 3.15 (m, 1H), 2.97 (m, 1H), 2.85 (m, 1H), 1.10 (d, 3H).

Step F 4-(4-Chlorophenyl)-2-methanesulfonyloxy-3-phenylbutane

To a solution of 4-(4-chlorophenyl)-3-phenyl-2-butanol (Step E, faster eluting isomer, 9.0 g, 34 mmol) in EtOAc (100 mL) at 0° C. was added triethyl amine (dried over activated molecular sieves, 5.8 mL. 42 mmol) and methanesulfonyl chloride (3.0 mL, 38 mmol). After stirring at 0° C. for 30 min, the reaction was quenched by addition of saturated aqueous sodium bicarbonate (100 mL). After stirring at room temperature for 1 h, the organic layer was separated, dried over anhydrous sodium sulfate, filtered, and concentrated to dryness to give the title compound, which was used without further purification. $^1$H NMR (500 MHz, CD$_3$OD): δ 7.3-7.0 (m, 9H), 5.05 (m, 1H), 3.2-3.0 (m, 3H), 2.80 (s, 3H), 1.40 (d, 3H).

Step G 2-Azido-4-(4-chlorophenyl)-3-phenylbutane

To a solution of 4-(4-chlorophenyl)-2-methanesulfonyloxy-3-phenylbutane (Step F, 12 g, 34 mmol) in DMF (50 mL) was added sodium azide (11 g, 0.17 mol). After stirring at 120° C. for 1 h, the reaction mixture was poured into water (200 mL), and the product was extracted with ether (2×100 mL). The combined organic extracts were washed with water, dried over MgSO$_4$, filtered and concentrated to dryness, and the residue was purified on a silica gel column eluting with hexane to give the title compound.

Step H 2-(N-tert-Butoxycarbonyl)amino-4-(4-chlorophenyl)-3-phenylbutane

To a solution of 2-azido-4-(4-chlorophenyl)-3-phenylbutane (Step G, 7.0 g, 24 mmol) in EtOAc (150 mL) was added di(tert-butyl)dicarbonate (8.0 g, 37 mmol) and platinum dioxide (0.50 g, 2.2 mmol). The mixture was degassed and filled with hydrogen with a balloon. After stirring for 1 day, the reaction mixture was filtered through CELITE diatomaceous earth, and the filtrate was concentrated to give the crude product, which was contaminated with some unreacted di(tert-butyl)dicarbonate. $^1$H NMR (500 MHz, CD$_3$OD): δ 7.25-6.88 (m, 9H), 3.89 (m, 1H), 3.20 (m, 1H), 2.86-2.77 (m, 2H), 1.54 (s, 9H), 0.92 (d, 3H).

Step I N-[3-(4-Chlorophenyl)-2-phenyl-1-methylpropyl]-amine hydrochloride (Diastereomer α)

2-N-tert-butoxycarbonyl)amino-4-(4-chlorophenyl)-3-phenylbutane (Step H, 7.0 g, 24 mmol) was treated with a saturated solution of hydrogen chloride in EtOAc (100 mL) at room temperature for 30 min (4 M hydrogen chloride in dioxane may be used with similar results). The mixture was concentrated to dryness to give the title compound. $^1$H NMR (500 MHz, CD$_3$OD): δ 7.35-6.98 (m, 9H), 3.62 (m, 1H), 3.20 (dd, 1H), 3.05 (m, 1H), 2.98 (dd, 1H), 1.19 (d, 3H). LC-MS: m/e 260 (M+H)$^+$ (2.3 min).

REFERENCE EXAMPLE 11

N-[3-(4-Chlorophenyl)-2(S)-phenyl-1(S)-methlpropyl]-amine hydrochloride

Step A 4-(4-Chlorophenyl)-3(S)-phenyl-2(R)-butanol

A sample of magnesium (20 g, 0.82 mol) was activated by stirring under nitrogen for 12 h, and anhydrous ether (100 mL) was added to cover the solid material. The mixture was cooled to 0° C., and was added 4-chlorobenzyl chloride (40 g, 0.25 mmol) in 400 mL anhydrous ether dropwise. After stirring at room temperature for 1 h, a sample of the above solution (32 mL) was added to (1R,2R)-1-phenylpropylene oxide (1.0 g, 7.5 mmol) in 100 mL ether at 0° C. via syringe. After stirring at 0° C. for 2 h, the reaction was quenched by addition of saturated aqueous ammonium chloride (100 mL). The organic layer was separated and the aqueous layer extracted with ether (2×100 mL). The combined organic extracts were washed with brine, dried over anhydrous MgSO$_4$, filtered, and concentrated to dryness, and the residue was purified by flash column chromatography on silica gel eluted with hexane to 15% EtOAc in hexane to afford the title compound. $^1$H NMR (500 MHz, CD$_3$OD): δ 7.28-7.02 (m, 9H), 4.01 (m, 1H), 3.14 (dd, 1H), 2.97 (dd, 1H), 2.85 (m, 1H), 1.12 (d, 3H).

Step B N-[3-(4-chlorophenyl)-2(S)-phenyl-1(S)-methylpropyl]-amine, hydrochloride The product of Step A (4-(4-chlorophenyl)-3(S)-phenyl-2(R)-butanol, 1.8 g, 7.0 mmol) was converted to the title compound following the steps described in Reference Example 10, Steps F-I, except hydrogen chloride in dioxane (4 M) was used in place of hydrogen chloride in EtOAc. $^1$H NMR (500 MHz, CD$_3$OD): δ 7.35-6.98 (m, 9H), 3.62 (m, 1H), 3.20 (dd, 1H), 3.05 (m, 1H), 2.98 (dd, 1H), 1.19 (d, 3H). LC-MS: m/e 260 (M+H)$^+$ (2.3 min).

REFERENCE EXAMPLE 12

2-Amino-4-(4-chlorophenyl)-3-(3-fluorophenyl) butane hydrochloride salt (mixture of diastereomers α/β 5:1)

Step A Methyl 3-(4-Chlorophenyl)-2-(3-fluorophenyl)propionate

To a solution of 3-fluorophenylacetic acid (5.0 g, 32 mmol) in MeOH (25 mL) and CH$_2$Cl$_2$ (25 mL) at 0° C. was added trimethylsilyldiazomethane (2 M in hexane, 30 mL, 60 mmol). After stirring at room temperature for 15 min, the reaction mixture was concentrated to dryness, and the residue was azeotroped with toluene to give the crude methyl 3-fluorophenylacetate (5.6 g), which was used without further purification. Thus, the crude methyl 3-fluorophenylacetate obtained above (2.5 g, 15 mmol) was converted to the title compound (purified on silica gel) by reacting with 4-chlorobenzyl bromide (4.6 g, 22 mmol) and sodium hexamethyldisilazide (1 M in THF, 15 mL, 15 mmol) following the procedure described in Reference Example 10, Step A. $^1$H NMR (400 MHz, CD$_3$OD): δ 7.35-6.88 (m, 8H), 3.92 (t, 1H), 3.60 (s, 3H), 3.34 (dd, 1H), 3.00 (dd, 1H). LC-MS: m/e 305 (M+Na)$^+$ (3.9 min).

Step B N-Methoxy-N-methyl-3-(4-chlorophenyl)-2-(3-fluorophenyl)propanamide

To a suspension N-methoxy-N-methylamine hydrochloride (2.0 g, 21 mmol) in 50 mL CH$_2$Cl$_2$ at 0° C. was added dimethylaluminum chloride (1 M in hexane, 21 mL, 21 mmol). After stirring at room temperature for 1 h, a solution of methyl 3-(4-chlorophenyl)-2-(3-fluorophenyl)propionate (Step A, 2.0 g, 10 mmol) in CH$_2$Cl$_2$ (10 mL) was added, and the resulting mixture was stirred overnight. The reaction mixture was quenched by addition of MeOH (5 mL), and the resulting mixture was concentrated with silica gel (50 g). The material was loaded onto a silica gel column, which was eluted with 10% EtOAc in hexane to 2% ammonia in MeOH (2 M) in 10% EtOAc/hexane to give the title compound. $^1$H NMR (400 MHz, CD$_3$OD): δ 7.35-6.90 (m, 8H), 4.39 (br, 1H), 3.41 (s, 3H), 3.38-3.30 (m, 1H), 3.08 (s, 3H), 2.92 (dd, 1H). LC-MS: m/e 322 (M+H)$^+$ (3.6 min).

Step C 4-(4-Chlorophenyl)-3-(3-fluorophenyl)-2-butanol

The product of Step B (N-methoxy-N-methyl-3-(4-chlorophenyl)-2-phenylpropionamide) (0.74 g, 2.3 mmol) was converted to the title compound (a 5:1 mixture of diastereomers) following the procedure described in Reference Example 10, Steps D-E. $^1$H NMR (400 MHz, CD$_3$OD): δ 7.22-6.78 (m, 8H), 3.98 (m, 1H), 3.11 (dd, 1H), 2.94 (dd, 1H), 2.85 (m, 1H), 1.08 (d, 3H).

Step D 2-Azido-4-(4-chlorophenyl)-3-(3-fluorophenyl)butane

To a mixture of 4-(4-chlorophenyl)-2-(3-fluorophenyl)-2-butanol (Step C, 0.65 g, 2.3 mmol), triphenylphosphine (1.2 g, 4.7 mmol), imidazole (0.32 g, 4.7 mmol) and zinc azide dipyridine complex (Viaud, M. C.; Rollin, P. Synthesis 1990, 130) (0.72 g, 2.3 mmol) in 10 mL CH$_2$Cl$_2$ was added diethylazodicarboxylate (0.73 mL, 4.7 mmol) at 0° C. After stirring at room temperature for 30 min, the resulting mixture was concentrated with silica gel (20 g) and loaded onto a silica gel column, which was eluted with 2% ether in hexane to 2% ammonia in MeOH (2 M) in 2% ether/hexane to give the title compound. $^1$H NMR (400 MHz, CD$_3$OD): δ 7.25-6.85 (m, 8H), 3.76 (m, 1H), 3.33 (m, 1H), 2.92 (m, 2H), 1.15 (d, 3H).

Step E 2-Amino-4-(4-Chlorophenyl)-3-(3-fluorophenyl)butane hydrochloride salt (mixture of diastereomers α/β 5:1)

The product of Step D (2-azido-4-(4-chlorophenyl)-3-(3-fluorophenyl)butane) (0.49 g, 1.6 mmol) was converted to the title compound following the steps described in Reference Example 10, Steps H-I. $^1$H NMR (400 MHz, CD$_3$OD): δ 7.32-6.90 (m, 7H), 3.61 (m, 1H), 3.20 (dd, 1H), 3.11 (m, 1H), 2.92 (dd, 1H), 1.19 (d, 3H). LC-MS: m/e 278 (M+H)$^+$ (2.4 min).

The amines of Reference Examples 13-16 were prepared according to the procedures described in Reference Example 12:

| Reference Example | Name | LC/MS |
|---|---|---|
| 13 | 2-Amino-4-(4-chlorophenyl)-3-(2-fluorophenyl)butane hydrochloride salt (mixture of diastereomers α/β 10:1) | LC-MS: m/e 278 (M + H)$^+$ (2.3 min). |
| 14 | 2-Amino-4-(4-chlorophenyl)-3-(4-fluorophenyl)butane hydrochloride salt (mixture of diastereomers α/β 10:1) | LC-MS: m/e 278 (M + H)$^+$ (2.5 min). |
| 15 | 2-Amino-4-(4-chlorophenyl)-3-(2-pyridyl)butane hydrochloride salt (mixture of diastereomers α/β 10:1) | LC-MS: m/e 261 (M + H)$^+$ (1.6 min). |
| 16 | 2-Amino-4-(4-chlorophenyl)-3-(4-pyridyl)butane hydrochloride salt (mixture of diastereomers α/β 10:1) | LC-MS: m/e 261 (M + H)$^+$ |

REFERENCE EXAMPLE 17

2-Amino-4-(4-cyanophenyl)-3-phenylbutane hydrochloride salt (mixture of diastereomers α/β 10:1)

Step A 4-(4-Cyanophenyl)-3-phenyl-2-butanone

To a solution of phenylacetone (1.2 g, 9.0 mmol) and 4-cyanobenzyl chloride (1.4 g, 9.0 mmol) in 20 mL CH$_2$Cl$_2$ at −78° C. was added cesium hydroxide monohydrate (4.5 g, 27 mmol) and tetrabutyl ammonium iodide (20 mg). The reaction was allowed to warm to room temperature over 6 h, and the resulting mixture partitioned between brine (100 mL) and EtOAc (100 mL). The organic layer was separated and the aqueous layer extracted with EtOAc (2×100 mL). The combined organic extracts were dried over MgSO$_4$, filtered, and concentrated to dryness, and the residue was purified by flash column chromatography on silica gel eluted with 20-50% EtOAc in hexane to give the title compound. $^1$H NMR (500 MHz, CD$_3$OD): δ 7.52 (d, 2H), 7.34-7.16 (m, 7H), 4.12 (dd, 1H), 3.41 (dd, 1H), 3.00 (dd, 1H). LC-MS: m/e 250 (M+H)$^+$ (3.2 min).

Step B 2-Amino-4-(3-cyanophenyl)-3-phenylbutane hydrochloride salt (mixture of diastereomers α/β 10:1)

The product of Step A (4-(4-cyanophenyl)-3-phenyl-2-butanone) (1.0 g, 4.0 mmol) was converted to the title compound following the procedure described in Reference Example 10, Steps E-I. LC-MS: m/e 251 (M+H)$^+$ (1.9 min).

REFERENCE EXAMPLE 18

2-Amino-4-(5-chloro-2-pyridyl)-3-phenylbutane hydrochloride salt (mixture of diastereomers α/β 10:1)

5-Chloro-2-chloromethylpyridine (Weidmann, K. et al. *J. Med. Chem.* 1992, 35, 438) was used in place of 4-cyanobenzyl bromide in Step A of Reference Example 17. LC-MS: m/e 261 (M+H)$^+$.

REFERENCE EXAMPLE 19

N-[3-(4-chlorophenyl)-2-(3-pyridyl)-1-methylpropyl]-amine, hydrochloride (mixture of diastereomers α/β 10:1)

Step A 4-(4-Chlorophenyl)-3-pyridyl-2-butanone

To a solution of 3-pyridylacetone hydrochloride (Wibaud, van der V. *Recl. Trav. Chim. Pays-Bas.* 1952, 71, 798) (10 g, 58 mmol) and 4-chlorobenzyl chloride (9.1 g, 58 mmol) in 100 mL CH$_2$Cl$_2$ at −78° C. was added cesium hydroxide monohydrate (39 g, 0.23 mol) and tetrabutyl ammonium iodide (1 g). The reaction was allowed to warm to room temperature overnight, and the resulting mixture was partitioned between brine (100 mL) and EtOAc (100 mL). The organic layer was separated and the aqueous layer extracted with EtOAc (2×100 mL). The combined organic extracts were dried over anhydrous MgSO$_4$, filtered, and concentrated to dryness to give the title compound. $^1$H NMR (500 MHz, CD$_3$OD): δ 8.42 (d, 1H), 8.34 (d, 1H), 7.72 (d, 1H), 7.40 (dd, 1H), 7.18 (d, 2H), 7.06 (d, 1H), 4.23 (dd, 1H), 3.38 (dd, 1H), 2.95 (dd, 1H), 2.10 (s, 3H). LC-MS: m/e 260 (M+H)$^+$ (1.9 min).

Step B N-[3-(4-chlorophenyl)-2-(3-pyridyl)-1-methylpropyl]-amine, hydrochloride (mixture of diastereomers α/β 10:1)

The product of Step A (4-(4-chlorophenyl)-3-pyridyl-2-butanone) (14 g, 57 mmol) was converted to the title compound following the procedure described in Reference Example 10, Steps E-I. LC-MS: m/e 261 (M+H)$^+$ (1.2 min).

REFERENCE EXAMPLE 20

2-Amino-4-(2,4-dichlorophenyl)-3-(4-chlorophenyl)butane hydrochloride salt (3 isomers)

Step A Methyl 3-(2,4-Dichlorophenyl)-2-(4-chlorophenyl)propionate

A sample of 4-chlorophenylacetic acid (4.2 g, 25 mmol) was converted to the title compound (6.5 g) following the procedure in Reference Example 12, Step A substituting 4-chlorophenylacetic acid for 3-fluorophenylacetic acid and 2,4-dichlorobenzyl bromide for 4-chlorobenzyl bromide following the procedures described in Reference Example 10, Step A. $^1$H NMR (500 MHz, CD$_3$OD): δ 7.40 (d, 1H), 7.32-7.22 (m, 4H), 7.15 (dd, 1H), 7.08 (d, 1H), 4.00 (t, 1H), 3.62 (s, 3H), 3.44 (dd, 1H), 3.12 (dd, 1H).

Step B 3-(2,4-Dichlorophenyl)-2-(4-chlorophenyl)propanol

To a solution of methyl 3-(2,4-dichlorophenyl)-2-(4-chlorophenyl)propionate (6.4 g, 8.6 mmol) in 50 mL ether at −40° C. was added lithium aluminum hydride (1.4 g, 37 mmol), and the reaction was allowed to warm to room temperature over 2 h. The reaction was quenched by addition of MeOH (3 mL) dropwise at −10° C., and the mixture was partitioned between 100 mL saturated ammonium chloride and EtOAc (100 mL). The organic layer was separated and the aqueous layer extracted with EtOAc (2×100 mL). The combined organic extracts were dried over anhydrous MgSO$_4$, filtered, and concentrated to dryness to give the title compound, which was used without further purification. ¹H NMR (400 MHz, CD₃OD): δ 7.4-6.9 (m, 7H), 3.72 (m, 2H), 3.24 (dd, 1H), 3.16 (m, 1H), 2.85 (dd, 1H).

Step C
3-(2,4-Dichlorophenyl)-2-(4-chlorophenyl)propanal

To a solution of 3-(2,4-dichlorophenyl)-2-(4-chlorophenyl)propanol (Step B, 0.89 g, 2.8 mmol) in 20 mL CH₂Cl₂ was added crushed activated molecular sieves (4 g). After stirring at room temperature for 10 min, pyridinium chlorochromate (0.90 g, 4.2 mmol) was added. After stirring at room temperature for 1 h, CELITE diatomaceous earth (4 g) was added followed by 100 mL ether. The resulting mixture was filtered through a silica gel pad, which was washed with ether (2×50 mL). The filtrate was concentrated to dryness and azeotroped with toluene to give the title compound, which was used without further purification.

Step D N-[3-(2,4-Dichlorophenyl)-2-(4-chlorophenyl)propylidene]-2-methylpropanesulfinamide To a solution of 3-(2,4-dichlorophenyl)-2-(4-chlorophenyl)propanal (Step C, 0.90 g, 2.8 mmol) in 6 mL THF was added (R)-(+)-2-methyl-2-propane-sulfinamide (0.5 gm, 4.1 mmol) followed by the addition of titanium tetraethoxide (1.5 mL, 8.0 mmol). After stirring at room temperature overnight, the reaction mixture was added to a well-stirred brine solution (50 mL). The resulting mixture was filtered through CELITE diatomaceous earth and washed with EtOAc (20 mL), and the filtrate was extracted with EtOAc (2×50 mL). The combined extracts were dried over anhydrous sodium sulfate, filtered, and concentrated to dryness, and the residue was purified by flash column chromatography on silica gel eluted with 10% ether in hexane to give the title compound as a 1:1 mixture of diastereomers. ¹H NMR (500 MHz, CD₃OD): δ 8.11 (m, 1H), 7.41 (m, 1H), 7.35-7.31 (m, 4H), 7.16-7.06 (m, 2H), 4.26 (m, 1H), 3.78-3.58 (m, 1H), 3.22-3.14 (m, 1H), 1.13/1.12 (s, 9H).

Step E N-[3-(2,4-Dichlorophenyl)-2-(4-chlorophenyl)-1-methylpropyl]-2-methylpropanesulfinamide (3 isomers)

To a solution of N-[3-(2,4-dichlorophenyl)-2-(4-chlorophenyl)-1-methylpropylidene]-2-methylpropanesulfinamide (Step D, 0.51 g, 1.3 mmol) in 6 mL CH₂Cl₂ at −60° C. was added methylmagnesium bromide (3 M in ether, 0.90 mL, 2.7 mmol). After stirring at −60° C. for 6 h, the reaction was allowed to warm to room temperature overnight. The resulting mixture was partitioned between saturated aqueous ammonium chloride (50 mL) and EtOAc (50 mL). The organic layer was separated and the aqueous layer extracted with EtOAc (2×50 mL). The combined extracts were dried over anhydrous sodium sulfate, filtered, and concentrated to dryness, and the residue was purified by flash column chromatography on silica gel eluted with 30 to 50% EtOAc in hexane to give the title compound as one pure faster elating enantiomer and a 1:1 mixture of slower co-eluting diastereomers. The addition of the methyl Grignard reagent was apparently stereoselective for one of the sulfinamide diastereomers. Faster eluting isomer: ¹H NMR (500 MHz, CD₃OD): δ 7.30 (d, 1H), 7.22 (d, 2H), 7.12 (d, 2H), 7.03 (dd, 1H), 6.94 (d, 1H), 3.62 (m, 1H), 3.56 (dd, 1H), 2.97 (dd, 1H), 1.23 (s, 9H), 1.04 (d, 3H). LC-MS: m/e 432 (M+H)⁺ (4.2 min). Slower eluting isomers (1:1): ¹H NMR (500 MHz, CD₃OD): δ 7.33/7.30 (d, 1H), 7.21/7.18 (d, 2H), 7.06/7.04 (d, 2H), 6.99/6.97 (dd, 1H), 6.79/6.75 (d, 1H), 3.70-3.55 (m, 1H), 3.07/2.97 (m, 1H), 2.90/2.80 (dd, 1H), 1.32/0.95 (s, 9H), 1.49/1.10 (d, 3H).

Step F 2-Amino-4-(2,4-dichlorophenyl)-3-(4-chlorophenyl)butane hydrochloride (3 isomers)

To a solution of N-[3-(2,4-dichlorophenyl)-2-(4-chlorophenyl)-1-methylpropyl]-2-methylpropanesulfinamide (Step F, faster eluting isomer, 50 mg, 0.11 mmol) in 5 mL MeOH was added hydrogen chloride in dioxane (4 M, 2 mL). After stirring at room temperature for 10 min, the reaction mixture was concentrated to dryness to give the title compound as one pure isomer. Isomer 1: ¹H NMR (500 MHz, CD₃OD): δ 7.35 (d, 1H), 7.29 (d, 2H), 7.15 (d, 2H), 7.06 (dd, 1H), 6.91 (d, 1H), 3.68 (m, 1H), 3.36 (dd, 1H), 3.06 (dd, 1H), 1.18 (d, 3H). LC-MS: m/e 328 (M+H)⁺ (2.8 min). The two slower co-eluting isomers were treated in the same fashion to give two other isomers of the title compound. Isomer 2 and 3 (1:1): LC-MS: m/e 328 (M+H)⁺ (2.7/2.8 min).

REFERENCE EXAMPLE 21

2-Amino-4-(4-chloro-2-fluorophenyl)-3-(4-chlorophenyl)butane hydrochloride salt (Isomers, 1, 2 and 3)

The title compound was prepared according to the procedures of Reference Example 20 substituting 2,5-dichlorobenzyl bromide with 4-chloro-2-fluorobenzyl bromide. Isomer 1: LC-MS: m/e 312 (M+H)⁺ (2.6 min). Isomer 2 and 3 (1:1): LC-MS: m/e 312 (M+H)⁺ (2.5/2.6 min).

REFERENCE EXAMPLE 22

2-(4-Chlorophenyloxy)-2-(4-chlorophenyl)ethylamine hydrochloride salt

Step A
2-(4-Chlorophenyloxy)-2-(4-chlorophenyl)ethanol

To a suspension of 2-(4-chlorophenyloxy)-2-(4-chlorophenyl)acetic acid (Newman et al *J. Amer. Chem. Soc.* 1947, 69, 718) (1.0 g, 3.4 mmol) in 10 mL THF at 0° C. was added borane (1 M in THF, 6.8 mL, 6.8 mmol). After stirring at room temperature for 2 h, the reaction was quenched by addition of 2 M hydrochloric acid (10 mL). The volatile materials were removed on a rotary evaporator, and the resulting mixture was partitioned between brine (20 mL) and EtOAc (30 mL). The organic layer was separated and the aqueous layer extracted with EtOAc (2×20 mL). The combined extracts were dried over anhydrous sodium sulfate, filtered, and concentrated to dryness to give the title compound, which was used without further purification. LC-MS: m/e 283 (M+H)⁺ (3.4 min).

Step B
2-(4-Chlorophenyloxy)-2-(4-chlorophenyl)ethyl Azide 2-(4-Chlorophenyloxy)-2-(4-chlorophenyl)ethanol (Step A, 0.45 g, 2.4 mmol) was converted to the title compound following the procedure described in Reference Example 12, Step D. ¹H NMR (500 MHz, CD₃OD): δ 7.41 (d, 2H), 7.37 (d, 2H), 7.18 (d, 2H), 6.86 (d, 2H), 5.42 (dd, 1H), 3.69 (dd, 1H), 3.45 (dd, 1H). LC-MS: m/e 308 (M+H)⁺ (4.3 min).

Step C
2-(4-Chlorophenyloxy)-2-(4-chlorophenyl)ethylamine

To a solution of 2-(4-chlorophenyloxy)-2-(4-chlorophenyl)ethyl azide (Step B, 0.23 g, 0.75 mmol) in 4 mLTHF at −20° C. was added trimethylphosphine (0.18 mL, 1.8 mmol), and the reaction was allowed to warm to room temperature over 2 h. Lithium hydroxide monohydrate (61 mg, 1.5 mmol) was added followed by 2 mL water. After stirring at room temperature for 30 min, the reaction was quenched by addition of 2 M hydrochloric acid (final pH=2). The volatile materials were removed on a rotary evaporator, and the resulting mixture was partitioned between brine (20 mL), 5 N aqueous sodium hydroxide (20 mL), ether (20 mL) and toluene (20 mL). The organic layer was separated and the aqueous layer extracted with ether (40 mL). The combined extracts were dried over anhydrous MgSO$_4$, filtered, and concentrated to dryness to give the title compound, which was contaminated with trimethylphosphine oxide and was used without further purification. $^1$H NMR (500 MHz, CD$_3$OD): δ 7.46-7.40 (m, 4H), 7.20 (d, 2H), 6.91 (d, 2H), 5.53 (m, 2H), 3.36 (m, 2H). LC-MS: m/e 282 (M+H)$^+$ (2.5 min).

REFERENCE EXAMPLE 23

2,2-Bis(4-chlorophenyl)ethylamine hydrochloride salt

Step A Methyl 3,3-Bis(4-chlorophenyl)propionate

A mixture of di(4-chlorophenyl)ketone (7.5 g, 30 mmol) and methyl(triphenylphosphoranylidene)acetate (10 g, 30 mmol) in 20 mL toluene was heated at 130° C. while allowing the solvent to slowly evaporate overnight. The resulting mixture was dissolved in CH$_2$Cl$_2$ (20 mL) and toluene (20 mL) and was concentrated with 30 g silica gel. The material was loaded onto a silica gel column, which was eluted with 6:3:1 hexane/CH$_2$Cl$_2$/ether to give the title compound.

Step B Methyl 3,3-Bis(4-chlorophenyl)propionate

A suspension of methyl 3,3-bis(4-chlorophenyl)propionate (Step A, 3.0 g, 14 mmol) and platinum dioxide (0.30 g) in MeOH (20 mL) and 2 M aqueous hydrochloric acid (1 mL) was degassed and filled with hydrogen with a balloon. After stirring at room temperature for 2 h, the reaction mixture was filtered through CELITE diatomaceous earth, and the filtrate was concentrated to dryness. The residue was dissolved in 50 mL ether and was concentrated with 20 g silica gel. The material was loaded onto a silica gel column, which was eluted with 10% ether in hexane to give the title compound. $^1$H NMR (500 MHz, CD$_3$OD): δ 7.29-7.22 (m, 4H), 4.50 (t, 1H), 3.56 (s, 3H), 3.07 (d, 2H). LC-MS: m/e 309 (M+H)$^+$ (4.1 min).

Step C 3,3-Bis(4-chlorophenyl)propionic Acid

A mixture of methyl 3,3-bis(4-chlorophenyl)propionate (Step B, 0.78 g, 3.9 mmol), lithium hydroxide monohydrate (0.33 g, 7.8 mmol) in 1:1:1 MeOH/THF/water (15 mL) was stirred at room temperature overnight. The resulting mixture was partitioned between 2 M aqueous hydrochloric acid (50 mL) and ether (50 mL). The organic layer was separated and the aqueous layer extracted with EtOAc (2×50 mL). The combined extracts were dried over anhydrous MgSO$_4$, filtered, and concentrated to dryness to give the title compound. $^1$H NMR (500 MHz, CD$_3$OD): δ 7.29-7.23 (m, 4H), 4.49 (t, 1H), 3.02 (d, 2H).

Step D
N-[2,2-Bis(4-chlorophenyl)ethyl]allylcarbamate

To a solution of 3,3-bis(4-chlorophenyl)propionic acid (Step C, 0.32 g, 1.1 mmol) and triethyl amine (0.60 mL, 4.3 mmol) in 4 mLTHF at 0° C. was added ethyl chloroformate (0.31 mL, 3.3 mmol). After stirring at room temperature for 30 min, the reaction was cooled to 0° C., and was added sodium azide (0.35 g, 5.4 mmol) in 2 mL water. After stirring at room temperature for 1 h, the reaction mixture was partitioned between brine (20 mL) and EtOAc (20 mL). The organic layer was separated and the aqueous layer extracted with EtOAc (2×20 mL). The combined extracts were dried over anhydrous sodium sulfate, filtered, and concentrated to dryness, and the residue was dissolved in allylic alcohol (1 mL) and toluene (1 mL). After stirring at 80° C. overnight, the reaction mixture was concentrated to dryness, and the residue was purified by flash column chromatography on silica gel column eluted with 20% EtOAc in hexane to give the title compound. $^1$H NMR (500 MHz, CD$_3$OD): δ 7.30-7.21 (m, 4H), 5.84 (m, 1H), 5.17 (dd, 1H), 5.10 (dd, 1H), 4.46 (d, 2H), 4.22 (t, 1H), 3.68 (d, 2H). LC-MS: m/e 350 (M+H)$^+$ (3.9 min).

Step E 2,2-Bis(4-chlorophenyl)ethylamine hydrochloride salt

To a solution of N-[2,2-bis(4-chlorophenyl)ethyl]allylcarbamate (Step D, 0.26 g, 0.73 mmol) in 1.5 mLTHF at 0° C. was added tetrakis(triphenylphosphine)palladium (85 mg, 0.073 mmol) and triphenylsilane (0.18 mL, 1.1 mmol). After stirring at 0° C. for 1 h, the reaction mixture was partitioned between ether (20 mL) and 2 M hydrochloric acid (20 mL). The aqueous layer was separated, and was added 5 N aqueous sodium hydroxide (final pH>12). The product was extracted with ether (3×30 mL), and the combined extracts were dried over sodium hydroxide, and filtered through CELITE, diatomaceous earth. After addition of 4 M hydrogen chloride in dioxane (2 mL), the filtrate was concentrated to dryness to give the title compound. $^1$H NMR (500 MHz, CD$_3$OD): δ 7.40-7.34 (m, 4H), 4.28 (m, 1H), 3.62 (d, 2H). LC-MS: m/e 266 (M+H)$^+$ (2.3 min).

REFERENCE EXAMPLE 24

2-Amino-3-(4-chlorophenylthio)-3-(4-chlorophenyl) propane hydrochloride salt (two diastereomers)

Step A Methyl 2-(4-Chlorophenylthio)-2-(4-chlorophenyl)acetate

To a solution of 2-(4-chlorophenylthio)-2-(4-chlorophenyl)acetic acid (Nicolaescu et al Rev. Roum. Chim. 1979, 24, 137) (1.0 g, 3.0 mmol) in MeOH (10 mL) and CH$_2$Cl$_2$ (10 mL) at 0° C. was added trimethylsilyldiazomethane (2 M in hexane) until a yellow color persisted. Concentration afforded the title compound, which was used without further purification.

Step B 2-Amino-3-(4-chlorophenylthio)-3-(4-chlorophenyl)propane hydrochloride salt (two diastereomers)

The product of Step A (methyl 2-(4-chlorophenylthio)-2-(4-chlorophenyl)acetate) (1.1 g, 3.0 mmol) was converted to the title compound following the procedures described in Reference Example 12, Steps B-E. LC-MS: m/e 312 (M+H)$^+$ (2.7 min).

REFERENCE EXAMPLE 25

2-Amino-3,4-bis(4-chlorophenyl)-2-methylbutane hydrochloride salt

Step A Methyl 2,3-Bis(4-chlorophenyl)propionate

The title compound was prepared following the procedure described in Reference Example 10, Step A, substituting methyl phenylacetate with methyl 4-chlorophenylacetate. $^1$H NMR (500 MHz, CD$_3$OD): δ 7.30-7.22 (m, 4H), 7.19 (d, 2H), 7.09 (d, 2H), 3.90 (t, 1H), 3.58 (s, 3H), 3.32 (dd, 1H), 2.98 (dd, 1H).

Step B 3,4-Bis(4-chlorophenyl)-2-methyl-2-butanol

To a solution of methyl 2,3-bis(4-chlorophenyl)propionate (2.6 g, 8.4 mmol) in ether (20 mL) was added methylmagnesium bromide (3 M in ether, 8.4 mL, 25 mmol) at −10° C., and the reaction was allowed to warm to room temperature over 2 h. The reaction mixture was poured into saturated aqueous ammonium chloride (100 mL), and the product was extracted with EtOAc (3×100 mL). The combined extracts were dried over anhydrous MgSO$_4$, filtered, and concentrated to dryness to give the title compound, which was used without further purification. $^1$H NMR (500 MHz, CD$_3$OD): δ 7.17 (ABq, 4H), 7.06 (d, 2H), 6.93 (d, 2H), 3.32 (dd, 1H), 2.94 (dd, 1H), 2.84 (dd, 1H), 1.20 (s, 3H), 1.16 (s, 3H).

Step C N-[2,3-Bis(4-chlorophenyl)-1,1-dimethylpropyl]chloroacetamide

To a solution of 3,4-bis(4-chlorophenyl)-2-methyl-2-butanol (Step B, 1.4 g, 4.5 mmol) and chloroacetonitrile (0.57 mL, 9.1 mmol) in acetic acid (0.7 mL) at −10° C. was added concentrated sulfuric acid (0.31 mL, 14 mmol). After stirring at −10° C. for 15 min and room temperature for 2 h, the reaction mixture was poured onto ice (20 g), and the product was extracted with EtOAc (3×20 mL). The combined extracts were washed with brine/saturated aqueous sodium bicarbonate, dried over anhydrous MgSO$_4$, filtered, and concentrated to dryness to give the title compound. $^1$H NMR (500 MHz, CD$_3$OD): δ 7.19 (ABq, 4H), 7.06 (d, 2H), 6.95 (d, 2H), 3.93 (ABq, 2H), 3.89 (dd, 1H), 3.10 (dd, 1H), 2.99 (dd, 1H), 1.43 (s, 3H), 1.25 (s, 3H). LC-MS: m/e 384 (M+H)$^+$ (3.9 min).

Step D 2-Amino-3,4-bis(4-chlorophenyl)-2-methylbutane hydrochloride

To a solution of N-[2,3-bis(4-chlorophenyl)-1,1-dimethylpropyl]chloroacetamide (Step C, 1.3 g, 3.8 mmol) in ethanol (10 mL) and acetic acid (2 mL) was added thiourea (0.34 g, 4.5 mmol). The reaction was stirred at 80° C. overnight to give a white precipitate. The precipitate was removed by filtration and washed with ethanol (10 mL), and the filtrate was diluted with dilute aqueous sodium hydroxide and extracted with hexane (2×50 mL). The combined extracts were dried over sodium hydroxide, filtered, and concentrated to dryness, and the residue was taken up by hydrogen chloride in dioxane (4 M, 5 mL) and concentrated to dryness to give the title compound. $^1$H NMR (500 MHz, CD$_3$OD): (free amine) δ 7.22-7.14 (m, 4H), 7.06 (d, 2H), 6.96 (d, 2H), 3.22 (dd, 1H), 2.95 (dd, 1H), 2.86 (dd, 1H), 1.16 (s, 3H), 1.10 (s, 3H).

REFERENCE EXAMPLE 26

2-Amino-5-methyl-3-phenylhexane hydrochloride salt

Step A 4-Methyl-2-phenylpentanoic acid

A solution of 0.25 g (1.84 mmol) of phenylacetic acid in 3.6 mL dry THF was cooled in ice bath and 4 mL 1M lithium bis(trimethylsilyl)amide was added. After 15 min, 0.23 mL (2.02 mmol) of isobutyliodide was added and the cold bath was removed. After stirring the reaction overnight, it was quenched with water and extracted once with EtOAc. The aqueous layer was acidified with 1.2 N HCl and extracted with EtOAc. The EtOAc solution was washed with brine, dried and concentrated to furnish the title compound which was used in the next step without purification. $^1$H NMR: (500 MHz, CDCl$_3$): δ 0.92 (d, 6H), 1.51 (m, 1H), 1.72 (m, 1H), 1.98 (m, 1H), 3.67 (m, 1H), 7.0-7.4 (m, 5H).

Step B
N-Methoxy-N-methyl-4-methyl-2-phenylpentanamide

To a solution of 0.234 g (1.22 mmol) of 4-methyl-2-phenylpentanoic acid in 6 mL CH$_2$Cl$_2$ and 2 drops of DMF, 0.12 mL (1.34 mmol) of oxalyl chloride was added. The solution was stirred for 1 h and concentrated. The residue was dissolved in 1 mL CH$_2$Cl$_2$ and added to a mixture of 0.142 g N,O-dimethylhydroxylamine hydrochloride in 4 mL CH$_2$Cl$_2$ and 4 mL saturated NaHCO$_3$. After stirring for 4 h, the layers were separated and the aqueous layer was extracted with CH$_2$Cl$_2$. The combined CH$_2$Cl$_2$ layer was washed with brine, dried and concentrated to give the title compound which was used in the next step without purification. $^1$H NMR: (500 MHz, CDCl$_3$): δ 0.94 and 0.96 (2d, 6H), 1.5 (m, 1H), 1.67 (m, 1H), 2.0 (m, 1H), 3.19 (s, 3H), 3.54 (s, 3H), 4.18 (br, 1H), 7.2-7.4 (m, 5H).

Step C 5-Methyl-3-phenyl-2-hexanone

To a solution of 75 mg (0.317 mmol) N-methoxy-N-methyl-4-methyl-2-phenylpentanamide in 1 mL dry THF, 0.45 mL 1.4 M methylmagnesium bromide was added. The reaction was stirred for 1 h, quenched with 1.2 N HCl and extracted with EtOAc. The EtOAc solution was washed with brine, dried and concentrated leaving the title compound. $^1$H NMR: (500 MHz, CDCl$_3$): δ 0.95 (2d, 6H), 1.42 (m, 1H), 1.67 (m, 1H), 1.9 (m, 1H), 2.06 (s, 3H), 3.73 (m, 1H), 7.0-7.4 (m, 5H).

Step D 5-Methyl-3-phenyl-2-hexanol

A solution of 66 mg (0.345 mmol) of 5-methyl-3-phenyl-2-hexanone in 1 mL MeOH was treated with 16 mg sodium borohydride. After 1.5 h, the reaction was quenched with 1.2 N HCl and concentrated. The residue was partitioned between EtOAc and water. The organic layer was washed with brine, dried and concentrated to yield the crude title compound which was used without purification. $^1$H NMR: (500 MHz, CDCl$_3$): δ 0.88 (2d, 6H), 1.0-1.9 (m, 4H), 1.2 (d, 3H), 2.64 (m, 1H), 3.9 (m, 1H), 7.2-7.4 (m, 5H).

Step E 2-Azido-5-methyl-3-phenylhexane

To a solution of 60 mg 5-methyl-3-phenyl-2-hexanol in 2 mL CH$_2$Cl$_2$, 0.163 g (0.62 mmol) of triphenylphosphine and 96 mg (0.31 mmol) of zinc azide pyridine were added. The reaction mixture was cooled in an ice bath and 98 mL (0.62 mmol) of DEAD was added. The cold bath was removed and the solution was stirred for 3 h. The reaction mixture was filtered through a pad of CELITE diatomaceous earth and the pad was rinsed with $CH_2Cl_2$. The filtrate was concentrated and the residue was purified by prep-TLC using 20% EtOAc-hexane to isolate the title compound. $^1$H NMR: (500 MHz, $CDCl_3$): δ 0.88 (2d, 6H), 1.12 (d, 3H), 1.31 (m, 1H), 1.72 (m, 2H), 2.68 (m, 1H), 3.53 (m, 1H), 7.2-7.4 (m, 5H).

Step F 2-Amino-5-methyl-3-phenylhexane

To a solution of 32 mg 2-azido-5-methyl-3-phenylhexane in 1 mL MeOH and 2 drops of 1.2 N HCl, 4 mg $PtO_2$ was added and the solution was stirred under H2 atmosphere for 2 h. The reaction was filtered through a pad of CELITE diatomaceous earth and the pad was rinsed with MeOH. The combined filtrate was concentrated to give the desired product. $^1$H NMR: (500 MHz, $CDCl_3$): δ 0.86 (m, 6H), 0.99 (d, 3H), 1.25 (m, 1H), 1.54 (m, 1H), 1.77 (m, 1H), 2.73 (m, 1H), 3.19 (m, 1H), 7.2-7.4 (m, 5H).

REFERENCE EXAMPLE 27

N-[3-(4-Chlorophenyl)-2-(3,5-difluorophenyl)-1-methylpropyl]anine hydrochloride (Diastereomer α)

The title compounds were prepared following the procedures described for Reference Example 10 substituting methyl phenylacetate with methyl 3,5-difluorophenylacetate (prepared from 3,5-difluorophenylacetic acid and trimethylsilyldiazomethane) at Step A and sodium borohydride in MeOH with lithium tri(sec-butylborohydride in THF at Step E. LC-MS: m/e 296 (M+H)$^+$ (2.39 min).

REFERENCE EXAMPLE 28

N-[2-(3-Bromophenyl)-3-(4-chlorophenyl)-1-methylpropyl]amine hydrochloride (Diastereomer α)

The title compounds were prepared following the procedures described for Reference Example 10 substituting methyl phenylacetate with methyl 3-bromophenylacetate (prepared from 3-bromophenylacetic acid and trimethylsilyldiazomethane) at Step A and sodium borohydride in MeOH with lithium tri(sec-butylborohydride in THF at Step E. LC-MS: m/e 338 (M+H)$^+$ (2.5 min).

REFERENCE EXAMPLE 29

N-[2-(3-Chlorophenyl)-3-(4-chlorophenyl)-1-methylpropyl]amine hydrochloride (Diastereomer α)

Step A 2-(N-tert-Butoxycarbonyl)amino-4-(4-chlorophenyl)-3-(3-trimethylstanylphenyl)butane
To a solution of 2-(N-tert-butoxycarbonyl)amino-3-(3-bromophenyl)-4-(4-chlorophenyl)butane (intermediate of Reference Example 28, 1.5 g, 3.4 mmol) in 15 mL anhydrous dioxane was added hexamethylditin (1.6 g, 4.8 mmol), triphenylphosphine (18 mg, 0.068 mmol), lithium chloride (0.16 g, 3.8 mmol) and tetrakis(triphenyl-phosphine)palladium (0.20 g, 0.17 mmol). After heating at 95° C. for 7.5 h under nitrogen, the reaction mixture was cooled to room temperature, diluted with EtOAc (100 mL), washed with 10% aqueous potassium fluoride and brine, dried over anhydrous $MgSO_4$, filtered and concentrated to dryness. The residue was purified by flash column chromatography on silica gel eluted with 20% EtOAc in hexane to afford the title compound. $^1$H NMR (500 MHz, $CD_3OD$): δ 7.3-7.2 (m, 2H), 7.07 (d, J=8.5 Hz, 2H), 7.06-6.99 (m, 2H), 6.86 (d, J=8.5 Hz, 2H), 3.93 (m, 1H), 3.18 (m, 1H), 2.76 (m, 2H), 1.51 (s, 9H), 0.94 (d, J=7.0 Hz, 3H), 0.21 (s, 9H).

Step B 2-(N-tert-Butoxycarbonyl)amino-3-(3-chlorophenyl)-4-(4-chlorophenyl)butane To a solution of 2-(N-tert-butoxycarbonyl)amino-4-(4-chlorophenyl)-3-(3-trimethylstanylphenyl)butane (0.55 g, 1.0 mmol) in 5 mL $CH_2Cl_2$ at 0° C. was added tert-butoxychloride (freshly prepared, 0.20 mL, 1.1 mmol). The reaction was allowed to warm to room temperature over 2 h, and the resulting mixture was concentrated with 2 g silica gel. The residue was purified by flash column chromatography on silica gel eluted with 10% ether in hexane to afford the title compound. $^1$H NMR (500 MHz, $CD_3OD$): δ 7.25-7.15 (m, 2H), 7.11 (d, J=8.5 Hz, 2H), 7.09 (m, 1H), 6.99 (d, J=7.5 Hz, 1H), 6.92 (d, J=8.5 Hz, 2H), 3.88 (m, 1H), 3.19 (dd, J=13.0, 3.5 Hz, 1H), 2.90-2.75 (m, 2H), 1.50 (s, 9H), 0.94 (d, J=6.5 Hz).

Step C N-[2-(3-Chlorophenyl)-3-(4-chlorophenyl)-1-methylpropyl]amine hydrochloride (Diastereomer α)

The title compound was prepared following the procedure described for Reference Example 10, Step I. LC-MS: m/e 294 (M+H)$^+$ (2.82 min).

REFERENCE EXAMPLE 30

N-[2-(3-Bromophenyl)-3-(4-chlorophenyl)-1-methylpropyl]amine hydrochloride and N-[3-(4-Chlorophenyl)-2-(3-iodophenyl)-1-methylpropyl]amine hydrochloride (1:1 Mixture) (Diastereomer α)

Step A 2-N-tert-Butoxycarbonyl)amino-3-(3-bromophenyl)-4-(4-chlorophenyl)-butane and 2-(N-tert-Butoxycarbonyl)amino-4-(4-chlorophenyl)-3-(3-iodophenyl)butane To a solution of 2-N-tert-butoxycarbonyl)amino-3-(3-bromophenyl)-4-(4-chlorophenyl)butane (intermediate of Reference Example 28, 2.6 g, 5.9 mmol) in 7 mL anhydrous THF at 0° C. was added methylmagnesium chloride (3 M in THF, 3.9 mL, 12 mmol). After 30 min, the reaction mixture was cooled to −78° C., and was added tert-butyllithium (1.7 M, 10 mL, 17 mmol). After stirring at −78° C. for 2 h, the reaction was allowed to warm to 0° C., and half of the resulting mixture was added to a suspension of iodine (5.0 g, mmol) in 10 mL THF at 40° C. The reaction mixture was allowed to warm to room temperature over 2 h, and was partitioned between ether (100 mL) and saturated aqueous ammonium chloride (100 mL). The organic layer was separated and the aqueous layer extracted with ether (2×50 mL). The combined extracts were washed with dilute aqueous sodium thiosulfate (2×) and brine, dried over anhydrous $MgSO_4$, filtered and concentrated to dryness. The residue was purified by flash column chromatography on silica gel eluted with 10% EtOAc in hexane to afford the title compounds as a 1:1 mixture.

Step B N-[2-(3-Bromophenyl)-3-(4-chlorophenyl)-1-methylpropyl]amine hydrochloride and N-[3-(4-chlorophenyl)-2-(3-iodophenyl)-1-methylpropyl]amine hydrochloride (1:1 mixture) (Diastereomer α)

The title compound was prepared following procedure described for Reference Example 10, Step I. LC-MS: m/e 338/386/(M+H)$^+$ (2.6 min).

REFERENCE EXAMPLE 31

2-Amino-4-(4-chlorophenyl)-3-cyclobutylmethoxybutane

Step A Methyl 2-diazo-3(4-chlorophenyl)propanoate (D,L)-4-Chlorophenylalanine methyl ester (5.0 g, 23.36 mmol) was dissolved in 120 mL chloroform and placed into an oven-dried 3-neck flask equipped with a condenser and an addition funnel. Glacial acetic acid (0.267 mL, 4.672 mmol) was added. Finally, isoamylnitrite (3.8 mL, 28 mmol) was added dropwise while slowly bringing the reaction to reflux (73° C.). The reaction was refluxed for 30 minutes and then cooled to 0° C. The reaction mixture was washed with cold 1 N sulfuric acid solution, cold water, cold saturated aqueous sodium bicarbonate solution, and then cold water again. The organic extracts were dried over MgSO$_4$, filtered and concentrated under reduced pressure. The crude mixture was purified by flash chromatography (Biotage 40M cartridge, gradient elution using hexane and EtOAc (100:1 to 50:1) to provide a yellow oil, homogeneous by TLC, $R_f$=0.48 (4:1 hexanes:EtOAc). 500 MHz $^1$H NMR (CDCl$_3$): δ 3.65 (s, 2H); 3.83 (s, 3H); 7.22 (d, J=8.5 Hz, 2H), 7.34 (d, J=8.5, 2H).

Step B Methyl 3-(4-chlorophenyl)-2-cyclobutylmethoxypropanoate

To a solution of 500 mg (2.23 mmol) of methyl-2-diazo-3-(4-chlorophenyl)propanoate (obtained from Step A) and 1.05 mL (5 eq; 11.1 mmol) of cyclobutanemethanol in 5 mL benzene in a pressure tube was added 10 mg (1 mole %) of Rh$_2$(OAc)$_4$ catalyst. The tube was sealed and heated to 90° C. for 1.5 h. The solvents were evaporated under reduced pressure and the crude material was taken up in CH$_2$Cl$_2$ and purified by flash chromatography via gradient elution using mixtures of hexane and EtOAc (100:1 to 50:1). This provided the title compound as a clear oil. TLC $R_f$=0.53 (4:1 hexanes:EtOAc). 500 MHz $^1$H NMR (CDCl$_3$): δ 1.68 (m, 2H); 1.85 (m, 1H); 1.88 (m, 1H); 2.01 (m, 2H); 2.53 (sep, 1H); 2.98 (m, 2H); 3.24 (dd, 1H); 3.58 (dd, 1H); 3.76 (s, 3H); 3.98 (dd, 1H); 7.20 (d, 2H); 7.28 (d, 2H).

Step C 4-(4-Chlorophenyl)-3-cyclobutylmethoxybutan-2-one

At 0° C., under anhydrous conditions, to a stirred suspension of N,O-dimethylhydroxylaminehydrochloride (732 mg, 7.50 mmol) in 60 mL CH$_2$Cl$_2$ was added dimethylaluminum chloride (7.5 mL, 1M solution in hexanes). The solution was allowed to warm to room temperature over a period of one hour. At that point a solution of methyl 2-cyclobutylmethoxy-3-(4-chlorophenyl)propanoate (531 mg, 1.88 mmol, obtained from Step B) in CH$_2$Cl$_2$ (8 mL) was added dropwise. The reaction was allowed to stir overnight at room temperature when TLC indicated completion of reaction. The reaction was worked up by the addition of pH=8 phosphate buffer (25 mL, approx. 3 mL/mmol of Me$_2$AlCl) and allowed to stir at room temperature for 30 minutes, diluted with chloroform (75 mL), and the phases were separated. The organic layer was washed with water and dried over MgSO$_4$. The solvents were evaporated under reduced pressure and the crude product was purified by flash chromatography (gradient elution using hexane and EtOAc, 20:1 to 5:1) to give the Weinreb amide as a clear oil). This purified material (424 mg, 1.36 mmol) was dissolved in 10 mL THF, injected into an oven dried flask, and cooled to 0° C. under nitrogen. Methyl magnesium bromide (1.4 mL 3M solution in ether) was added to the solution dropwise. The reaction was allowed to warm to room temperature. After 4 h the TLC indicated a complete reaction. The reaction was quenched with enough 10% citric acid to bring the pH of the solution to approximately 3. The aqueous layer was extract with ether. The combined organics were washed with water and then dried over MgSO$_4$. The solvents were evaporated under reduced pressure and the crude material was purified by flash chromatography (hexane:EtOAc, 100:1 to 50:1), resulting in the title compound as a clear oil. TLC $R_f$=0.55 (4:1 hexanes:EtOAc). 500 MHz $^1$H NMR (CDCl$_3$): δ 1.71 (m, 2H); 1.84 (m, 1H); 1.91 (m, 1H); 2.01 (m, 2H); 2.17 (s, 3H); 2.53 (sep, 1H); 2.90 (m, 2H); 3.28 (dd, 1H); 3.43 (dd, 1H); 3.81 (dd, 1H).

Step D 2-Amino-4-(4-chlorophenyl)-3-cyclobutylmethoxybutane

A solution of 3-cyclobutylmethoxy-4-(4-chlorophenyl)butan-2-one (247 mg, 0.925 mmol, obtained from Step C) in 0.5 mL CH$_2$Cl$_2$ was added to a stirred suspension of NH$_4$OAc (715 mg, 9.25 mmol) and NaBH$_3$CN (35 mg, 0.555 mmol) at room temperature and allowed to stir overnight. The reaction was quenched by the addition of 2.2 mL conc. HCl allowed to stir for 30 minutes. The solvents were evaporated under reduced pressure and the residue was partitioned between ether and water. The aqueous layer was washed two more times with ether. The combined organics were dried over Na$_2$SO$_4$. The crude product mixture obtained after filtration and removal of volatiles was purified by flash chromatography, eluting using mixtures of mixtures of CH$_2$Cl$_2$ and MeOH (100% CH$_2$Cl$_2$, to 5% MeOH in CH$_2$Cl$_2$) to provide the title compound as a yellow oil, homogeneous by TLC $R_f$=0.12 (5% MeOH in CH$_2$Cl$_2$). 500 MHz $^1$H NMR (CDCl$_3$): δ 1.16 (t, 3H); 1.67 (m, 2H); 1.85 (m, 3H); 2.01 (m, 2H); 2.48 (m, 1H); 2.74 (m, 2H); 2.90 (dd, 1H); 3.15 (d quint, 2H); 3.37 (m, 2H).

2-Amino-4-(4-chlorophenyl)-3-methoxy-butane, 2-amino-4-(4-chlorophenyl)-3-ethoxy-butane, 2-amino-4-(4-chlorophenyl)-3-n-propyloxy-butane, 2-amino-4-(4-chlorophenyl)-3-n-pentyloxy-butane, and 2-amino-4-(4-chlorophenyl)-3-cyclopentylmethoxy-butane were prepared according to the procedures described in Reference Example 31 substituting an appropriate alcohol for cyclobutylmethanol in Step B.

REFERENCE EXAMPLE 32

2-Amino-4-(4-chlorophenyl)-3-(1-pyrrolidinyl)-butane hydrochloride

Step A Ethyl 344-chlorophenyl)-2-pyrrolidin-N-yl-propanoate

While stirring rapidly, to a mixture of (D,L)-4-chlorophenylalanine methyl ester hydrochloride (2.5 g, 10 mmole), 40 mL ethanol and sodium carbonate (3.18 g, 30 mmole) was added dropwise a solution of 1,4-dibromobutane (2.16 g, 10 mmol) dissolved in 20 mL ethanol. The mixture was refluxed overnight. The volatiles were removed under reduced pressure, and the residue was partitioned between water and EtOAc. The aqueous layer was re-extracted with EtOAc thrice. The organic layers were combined and washed with water and brine and dried over anhydrous MgSO$_4$. The crude product obtained after filtration and removal of volatiles was purified via flash chromatography using mixtures of CH$_2$Cl$_2$ and MeOH to provide the titled compound as an oil, homogeneous by TLC, R$_f$=0.55 in 95:5 CH$_2$Cl$_2$:MeOH. LC/MS m/e=282.1 (M+1). 400 MHz $^1$H NMR (CDCl$_3$) δ 1.12 (t, J=7.2 Hz, 3H), 1.72 (m, 4H), 2.67 (m, 1H), 2.76 (m, 1H), 3.05 (m, 4H), 3.43 (m, 1H), 4.05 (m, 2H), 7.13 (d, J=8.2 Hz, 2H), 7.24 (d, J=8.2 Hz, 2H)

Step B 4-(4-Chlorophenyl)-3-(1-pyrrolidinyl)-butan-2-one

The title compound was prepared according to the procedure of Reference Example 10, Step C except that ethyl 3-(4-chlorophenyl)-2-(1-pyrrolidinyl)-propanoate (from Step A) was the ester used (two steps). TLC R$_f$=0.7 (95:5 CH$_2$Cl$_2$:MeOH). LC/MS m/e=252 (M+1). 500 MHz $^1$H NMR (CDCl$_3$) δ 1.86 (br s, 4H), 2.03 (s, 3H), 2.66 (m, 2H), 2.78 (m, 2H), 2.98 (dd, J=2.9, 10.3 Hz, 1H), 3.08 (m, 1H), 3.43 (m, 1H), 7.12 (d, J=8.3 Hz, 2H), 7.26 (d, J=8.3 Hz, 2H)

Step C 4-(4-Chlorophenyl)-3-pyrrolidin-N-yl-butan-2-one oxime

To a solution of 4-(4-chlorophenyl)-3-pyrrolidin-N-yl-butan-2-one (200 mg, 0.79 mmol, from Step B) dissolved in ethanol (2 mL), was added pyridine (63 mg, 0.79 mmol), and hydroxylamine hydrochloride (78 mg, 1.12 mmol). The mixture was refluxed for 24 h when LC/MS indicated disappearance of all starting material. The mixture was cooled to room temperature, concentrated under reduced pressure, treated with 33% aqueous potassium carbonated, and extracted with chloroform 5 times. The organic layers were combined and filtered over glass wool and dried over potassium carbonate. The filtrate obtained after passing through sintered glass was concentrated to give the oxime, homogeneous by TLC, R$_f$=0.3 in 95:5 CH$_2$Cl$_2$:MeOH. LC/MS m/e=267 (M+1). 500 MHz $^1$H NMR (CDCl$_3$) δ 1.73 (m, 4H), 1.76 (s, 3H), 2.40 (m, 2H), 2.60 (m, 2H), 2.72 (dd, J=2.7, 10.8 Hz, 1H), 2.94 (dd, J=4.3,8.8 Hz, 1H), 3.03 (dd, J=4.4, 13.3 Hz, 1H), 3.8 (s, 1H), 6.96 (d, J=8.3 Hz, 2H), 7.11 (d, J=8.3 Hz, 2H)

Step D 2-Amino-4-(4-chlorophenyl)-3-pyrrolidin-N-yl-butane hydrochloride

At room temperature, to a solution of 4-(4-chlorophenyl)-3-pyrrolidin-N-yl-butan-2-one oxime (173 mg, 0.648 mmol, from Step C) in 1.8 mL anhydrous THF was added dropwise a 1M solution of lithium aluminum hydride in THF (0.778 mmole). The mixture was refluxed for 20 h. The reaction was quenched by addition of saturated aqueous sodium sulfate (0.1 mL), and stirred overnight. This mixture was filtered over a pad of CELITE diatomaceous earth, and the filtrate was concentrated to dryness. The mass spectrum of this material looked very messy, so the HCl salt was prepared (by addition of a HCl(g) in ether solution) in attempt to clean up the mess. By NMR, the reductive amination provided a ~1:1 mixture of the two diastereomeric pairs of amines. This HCl salt was rather sticky and difficult to work with and therefore was used in the ensuing coupling experiment without further purification. LC/MS m/e=253 (M+1). 500 MHz $^1$H NMR (CD$_3$OD) δ 1.56, 1.59 (2 d, J=7.2 Hz, 3H), 2.03 (m, 6H), 2.08 (m, 2H), 3.20-4.00 (m, 3H), 7.43 (m, 4H)

REFERENCE EXAMPLE 33

Benzyl 3-amino-2-(4-chlorobenzyl)butyrate

Step A Benzyl 2-(4-chlorobenzyl)-3-ketobutyrate

Benzyl acetoacetate (1.92 g, 10 mmole) and 4-chlorobenzylbromide (2.05 g, 10 mmole) were dissolved in 40 mL anhydrous THF and cooled to −10° C. To this mixture was added dropwise slowly a solution of solution of sodium hexamethyl disilazide (0.5M solution in THF). Monoalkylation occurred almost exclusively of bisalkylation between −10 and 5° C. After quenching with water, the organics were extracted with EtOAc three times. The combined organic layer was washed with brine and dried over anhydrous MgSO$_4$. The crude product obtained after filtration and removal of volatiles was purified via flash chromatography using gradient elution (mixtures of hexane and EtOAc) to provide of the title compound as a clear yellow liquid, homogeneous by TLC, R$_f$=0.4 in 4:1 hexane:EtOAc. By NMR, this compound exists in a ~4:1 ratio of the keto: enol forms. 400 MHz $^1$H NMR (CDCl$_3$) δ 2.08, 2.18 (2 s, 3H), 3.15 (m, 2H), 3.80 (t, J=7.5 Hz, 0.8H), 5.14, 5.17 (2 s, 2H), 7.05-7.39 (m, 9H).

Step B Benzyl 3-amino-2-(4-chlorobenzyl)butyrate

Benzyl 2-(4-chlorobenzyl)-3-ketobutyrate (317 mg, 1 mmole, obtained from Step A) was added to a cooled mixture of 7M ammonia in MeOH (2.42 mL) and glacial acetic acid (1.6 mL). To this solution, at ~10° C., was added sodium cyanoborohydride (101 mg, 1.75 mmol) in small portions. This mixture was stirred at room temperature for 40 h. The excess sodium cyanoborohydride was destroyed by the addition of 6M HCl (to pH 1). The residue obtained after removal of volatiles was taken up in a minimal amount of water and extracted with ether. The aqueous layer was basified to pH 10 using solid KOH. This layer was then saturated with sodium chloride and then extracted with EtOAc. Further analyses of the ether and the EtOAc layers suggest that the desired product resides the EtOAc layer. This material was used in the ensuing coupling reaction without further purification. Proton NMR spectrum show that the two pairs of diastereomers are obtained in ~1:1 ratio, homogeneous by TLC, R$_f$=0.4 in 95:5 CH$_2$Cl$_2$:MeOH. LC/MS m/e=318 (M+1). 400 MHz $^1$H NMR (CDCl$_3$) δ 1.27, 1.29 (2 d, J=7 Hz, 3H), 2.85 (m, 1H), 3.03 (m, 1H), 3.15 (m, 1H), 3.55 (m, 1H), 4.85 (br, 2H), 5.00-5.18 (m, 2H), 7.0-7.2 (m, 9H).

REFERENCE EXAMPLE 34

2-Amino-4-(4-chlorophenyl)-3-cyclopentylbutane

Step A Methyl 3-(4-chlorophenyl)-2-cyclopentylpropanoate

A mixture of methyl cyclopentylacetate (3.52 g, 25 mmol) and 4-chlorobenzyl bromide (4.75 g, 23 mmol) was dissolved in 100 mL THF in an oven-dried flask. The solution was cooled to −40° C. and 23 mL 1M NaHMDS solution in hexanes was added slowly over an hour while maintaining the temperature at −40° C. The solution was then stirred for an additional 3 h at −40° C. The reaction was quenched at −40° C. with enough 10% citric acid solution to bring the pH to ~3.5. The aqueous layer was extracted with ether three times. The combined organics were washed with water and dried over MgSO$_4$. The solvents were evaporated under reduced pressure and the crude material was purified by flash chromatography [Biotage 40 M, gradient elution using mixtures of hexane and EtOAc (from 0-1% EtOAc)]. This provided a light brown oil, which is a 3:1 ratio of the title compound: methyl cyclopentylacetate based on the methyl ester peak integrations. TLC of the desired product: R$_f$=0.34 in 20:1 hexane:EtOAc. The complete separation of the title compound from the starting material was not practical in this case, as they had overlapping R$_f$'s on the TLC. Therefore, this mixture was carried on to the next step.

Step B 3-(4-Chlorophenyl)-2-cyclopentylpropanoic acid

The mixture of methyl esters from Step A (3.41 g, 14.48 mmol of methyl 3-(4-chlorophenyl)-2-cyclopentylpropanoate—assuming 3:1 mixture obtained in Step A.) was dissolved in 10 mL DMSO and 4 mL distilled water. Then powdered KOH (3.25 g, 57.92 mmol) was added and the solution was stirred overnight at room temperature. The next day the pH was brought to 2 with 2 N HCl. The aqueous layer was extracted 3 times with ether. The combined organic extracts were dried over anhydrous sodium sulfate. Filtration and evaporation of volatiles provided the mixture of acids as an oil. 500 MHz $^1$H NMR (CDCl$_3$): δ 1.28 (m, 2H), 1.64 (m, 6H), 2.06 (m, 1H), 2.47 (m, 1H), 2.86 (t, 2H).

Step C 3-(4-Chlorophenyl)-2-cyclopentyl-N,O-dimethyl-propanamide

The mixture of acids obtained in Step B (3.21 g, 14.48 mmol of the desired acid—based on assumption of 3:1 mixture from Step B) was dissolved in 75 mL CH$_2$Cl$_2$. While being stirred rigorously, N,O-dimethylhydroxylamine hydrochloride (1.56 g, 15.95 mmol), 1-ethyl-3-(3-dimethylaminopropyl)carbodiimide (3.06 g, 16.0 mmol), diisopropylethylamine (5.56 mL, 31.90 mmol), and a catalytic amount of 4-(dimethylaminopyridine) were added sequentially. Stirring was continued overnight at room temperature. The next day the reaction mixture was diluted with EtOAc, treated with water, and the phases were separated. The aqueous layer was re-extracted with EtOAc twice. The combined organic layers were washed with water three times and then with saturated brine. The organic layer was dried over MgSO$_4$, filtered, and the solvents were removed under reduced pressure. The crude material was purified by flash chromatography [Biotage 40 M column, gradient elution using mixtures or hexanes and EtOAc (100:1 to 20:1] to provide the title compound cleanly as an oil. TLC R$_f$=0.31 (4:1 hexanes:EtOAc). LC/MS m/e 295.9 (M+1). 500 MHz $^1$H NMR (CDCl$_3$): δ 1.27 (m, 2H), 1.64 (m, 6H), 1.97 (m, 1H), 2.13 (q, 1H), 2.81 (d, 1H), 2.97 (d, 1H), 3.07 (s, 3H), 3.17 (s, 3H). LC/MS m/e 295.9 (M+1).

Step D 4-(4-Chlorophenyl)-3-cyclopentylbutan-2-one 3-(4-Chlorophenyl)-2-cyclopentyl-N,O-dimethyl-propanamide (514 mg, 1.737 mmol, obtained from Step C) was dissolved in 15 mL anhydrous THF and injected into an oven dried flask under nitrogen. The solution was cooled to 0° C. and CH$_3$MgBr (1 M in ether) was added dropwise. The ice bath was removed and the reaction was allowed to warm to room temperature and stirred for a total of 4 h. TLC indicated a nearly complete reaction. The reaction was quenched with enough 10% citric acid to bring the pH of the solution to 3. The aqueous layer was extracted 3 times with ether and the extracts were dried over anhydrous MgSO$_4$. The solution was filtered and the solvents were removed under reduced pressure. The crude material was purified by flash chromatography (30 mL silica; 100:1 to 50:1 hexanes:EtOAc) to provide the title compound as an oil. TLC R$_f$=0.49 (4:1 hexanes: EtOAc). 500 MHz $^1$H NMR (CDCl$_3$): δ 1.23 (m, 3H), 1.58 (m, 1H), 1.71 (m, 3H), 1.91 (s, 3H), 1.93 (m, 1H), 2.05 (m, 1H), 2.68 (m, 1H), 2.84 (m, 2H).

Step E 2-Amino-4-(4-chlorophenyl)-3-cyclopentylbutane

The title compound was prepared according to the procedure of Reference Example 10, Step D, except that 4-(4-chlorophenyl)-3-cyclopentylbutan-2-one (obtained form Step D) was used as the starting material. LC/MS m/e 251.9 (M+1); 500 MHz $^1$H NMR (CDCl$_3$): δ 0.93 (m, 1H), 1.29 (q, 3H), 1.29 (m, 2H), 1.61 (m, 4H), 1.87 (m, 3H), 2.62 (m, 1H), 2.80 (m, 1H), 3.26 and 3.48 (m, 1H).

2-Amino-4-(4-chlorophenyl)-3-ethyl-butane and 2-amino-4-(4-chlorophenyl)-3-isopropyl-butane were also prepared according to the procedures described in Reference Example 34 substituting the appropriate ester for methyl cyclopentylacetate in Step A.

REFERENCE EXAMPLE 35

2-Amino-3-(1-(1,2,3-triazolyl))-4-(4-chlorophenyl) butane

Step A Benzyl 2-(1-(1,2,3-triazolyl))acetate

A mixture of 1,2,3-triazole (2.07 g, 30 mmol), benzyl bromoacetate (6.9 g, 30 mmol), and diisopropylethylamine (5.1 mL, 30 mmol) in 40 mL CH$_2$Cl$_2$ was stirred overnight at room temperature. This mixture was then diluted with ether until no further precipitate formed. The solid was filtered and washed with ether. The filtrate was concentrated and the residue was purified on silica gel using 10% hexane in CH$_2$Cl$_2$ to give the title compound's isomer, benzyl 2-(2-(1,2,3-triazolyl)acetate as amorphous solid. Further elution with a solvent mixture containing equal amounts of ether and CH$_2$Cl$_2$ gave the title compound as amorphous solid. $^1$H NMR (400 MHz, CDCl$_3$): δ 2.251 (s, 2H0, 7.267-7.390 (m, 5H), 7.723 (s, 1H), 7.785 (s, 1H).

Step B 2-(1-(1,2,3-triazolyl))acetic acid

Palladium hydroxide (20% on carbon, 800 mg) was added to a solution of benzyl 2-(1-(1,2,3-triazolyl))acetate (Step A, 8.68 g, 39.9 mmol) in 150 mL MeOH and the mixture was hydrogenated overnight on a Parr shaker under an atmosphere of hydrogen at room temperature and 45 psi. The catalyst was filtered through a bed of CELITE diatomaceous earth and washed with MeOH. The filtrate was concentrated to give a solid, which was dried in vacuo at 50° C. for 36 h resulting in the title compound. $^1$H NMR (400 MHz, CD$_3$OD): δ 5.3 (s, 2H), 7.75 (s, 1H0, 8.016 (s, 1H).

Step C N-Methoxy-N-methyl-2-(1-(1,2,3-triazolyl)) acetamide

Oxalyl chloride (0.95 mL, 11 mmol) was added dropwise to a suspension of 2-(1-(1,2,3-triazolyl))acetic acid (Step B, 1.27 g, 10 mmol) in 10 mL CH$_2$Cl$_2$ containing 0.05 mL DMF.

Vigorous effervescence was observed. This mixture was stirred at room temperature for 4 h and cooled to −78° C. A solution of N,O-dimethylhydroxylamine hydrochloride (1.2 g, 13 mmol) and diisopropylethyl amine (6.0 mL, 35 mmol) in 10 mL $CH_2Cl_2$ was added slowly over 3 min. The mixture was then allowed to warm to room temperature and stirred overnight. The reaction mixture was then diluted with ether until no additional precipitate appeared. The solid was filtered and washed with ether. The filtrate was concentrated and the residue was purified on silica gel using EtOAc as solvent to provide the title compound as amorphous solid. $^1H$ NMR (400 MHz, $CDCl_3$): δ 3.252 (s, 3H0, 3.812 (s, 3H), 5.379 (s, 2H), 7.753 & 7.761 (s's, 2H).

Step D N-Methoxy-N-methyl-3-(4-chlorophenyl)-2-(1-(1,2,3-triazolyl)) propionamide Lithium hexamethyldisilazide (1 molar in THF, 8.4 mL, 8.4 mmol) was added dropwise to a solution of N-methoxy-N-methyl-2-(1-(1,2,3-triazolyl))acetamide (Step C, 1.19 g, 7 mmol) in 15 mL THF at −78° C. After additional 30 min stirring, a solution of 4-chlorobenzyl bromide (1.65 g, 8 mmol) in 5 mL THF was added dropwise. The mixture was allowed to warm to room temperature and stirred 5.5 h. This mixture was purified on silica gel using 40% EtOAc in hexane to give the title compound. $^1H$ NMR (400 MHz, $CDCl_3$): δ 3.186 (s, 3H), 3.234-3.267 (m, 1H), 3.453-3.506 (m, 1H), 3.582 (s, 3H), 6.145-6.188 (m, 1H), 7.048-7.279 (m, 4H), 7.726 (s, 1H), 7.954 (s, 1H).

Step E 2-Azido-3-(1-(1,2,3-triazolyl))-4-(4-chlorophenyl)butane

The product of Step D, N-methoxy-N-methyl-3-(4-chlorophenyl)-2-(1-(1,2,3-triazolyl)propionamide was converted to the title compound following the procedures described in Reference Example 10, Step D-E and Reference Example 12, Step D. $^1H$ NMR (400 MHz, $CDCl_3$): δ 1.219-1.246 (d's 3H), 3.2534.754 (m, 4H0, 6.866-7.299 (d's, 4H), 7.313, 7.618, 7.63, & 7.706 (s's, 2H).

Step F 2-Amino-3-(1-(1,2,3-triazolyl))-4-(4-chlorophenyl)butane

Platinum oxide (14 mg) was added to a solution of 2-azido-3-(1-(1,2,3-triazolyl))-4-(4-chlorophenyl)butane (Step E, 138 mg, 0.5 mmol) in 4 mL MeOH. This mixture was hydrogenated in an atmosphere of hydrogen using a hydrogen filled balloon for 3 h at room temperature. The catalyst was filtered through a bed of CELITE diatomaceous earth and washed with MeOH. The filtrate was concentrated to give the title compound as oil. $^1H$ NMR (400 MHz, $CDCl_3$):δ 1.085-1.174 (d's 3H), 3.220-3.361 (m, 2H), 3.517-3.563 (m, 1H), 4.379-4.431 (m, 1H), 6.679-7.179 (d's, 4H), 7.297, 7.40, 7.592 & 7.607 (s's, 2H).

REFERENCE EXAMPLE 36

2-Amino-3-(1-(1,2,4-triazolyl)-4-(4-chlorophenyl)butane

The title compound was prepared according to the procedures described in Reference Example 35 substituting 1,2,4-triazole for 1,2,3-triazole in Step A. The azide was separated by column chromatography on silica gel eluted with 20% hexane in EtOAc.

REFERENCE EXAMPLE 37

N-[3-(4-Chlorophenyl)-2-(3-methylphenyl)-1-methylpropyl]amine hydrochloride (Diastereomer α)

Step A 2-(N-tert-Butoxycarbonyl)amino-4-(4-chlorophenyl)-3-(3-methylphenyl)butane A mixture of 2-(N-tert-butoxycarbonyl)amino-3-(3-bromophenyl)-4-(4-chlorophenyl)butane (intermediate of Reference Example 28, 0.50 g, 1.1 mmol), tetramethyltin (0.41 g, 2.3 mmol), triphenylphosphine (0.12 g, 0.46 mmol), lithium chloride (0.38 g, 9.1 mmol) and dichlorobis(triphenylphosphine)palladium (0.12 g, 0.17 mmol) in 20 mL anhydrous DMF was heated at 100° C. under nitrogen for 18 h. The reaction mixture was cooled to room temperature, and was partitioned between water (100 mL) and ether (100 mL). The organic layer was separated and the aqueous layer was extracted with ether (100 mL). The combined extracts were dried over anhydrous $MgSO_4$, filtered and concentrated to dryness, and the residue was purified by flash column chromatography on silica gel eluted with 10% EtOAc in hexane to afford the title compound. $^1H$ NMR (400 MHz, $CD_3OD$): δ 7.2-6.8 (m, 8H), 3.84 (m, 1H), 3.16 (m, 1H), 2.80-2.68 (m, 2H), 2.24 (s, 3H), 1.45 (s, 9H), 0.86 (d, 3H). LC-MS: m/e 396 $(M+Na)^+$ (4.4 min).

Step B N-[3-(4-Chlorophenyl)-2-(3-methylphenyl)-1-methylpropyl]amine hydrochloride (Diastereomer α)

The title compound was prepared following the procedure described for Reference Example 10, Step I. LC-MS: m/e 274 $(M+H)^+$ (2.5 min).

REFERENCE EXAMPLE 38

N-[3-(4-Chlorophenyl)-2-(3-trifluoromethylphenyl)-1-methylpropyl]amine hydrochloride (Diastereomer α)

The title compound was prepared following the procedure described in Reference Example 12 substituting fluorophenylacetic acid with 3-trifluoromethylphenylacetic acid at Step A. LC-MS: m/e 328 $(M+H)^+$ (2.6 min).

REFERENCE EXAMPLE 39

N-[3-(5-Chloro-2-pyridyl)-2(S)-phenyl-1(S)-methylpropyl]amine hydrochloride (Diastereomer α)

Step A 5-Chloro-2-methylpyridine

A mixture of 2,5-dichloropyridine (15 g, 0.10 mol), tetramethyltin (15 mL, 0.11 mol), and dichlorobis(triphenylphosphine)palladium (2.0 g, 2.8 mmol) in 200 mL anhydrous DMF was heated at 110° C. under nitrogen for 72 h. The reaction mixture was cooled to room temperature, and was poured into a saturated solution of potassium fluoride (200 mL). The resulting mixture was partitioned between water (500 mL) and ether (500 mL). The organic layer was separated and the aqueous layer was extracted with ether (200 mL). The combined extracts were dried over anhydrous $MgSO_4$, filtered and concentrated to dryness, and the residue was purified by flash column chromatography on silica gel eluted with 2 to 10% ether in hexane to afford the title compound. ¹H NMR (500 MHz, CD₃OD): δ 8.41 (d, 1H), 7.75 (dd, 1H), 7.30 (d, 1H), 2.53 (s, 3H).

Step B 4-(5-Chloro-2-pyridyl)-3(S)-phenyl-2(R)-butanol

To a solution of 5-chloro-2-methylpyridine (Step A, 1.1 g, 8.7 mmol) in 15 mL anhydrous ether was added phenyl lithium (1.8 M in cyclohexane/ether, 7.2 mL, 13 mmol) at 0° C., and the reaction was stirred at room temperature for 30 min. The resulting mixture was cooled back to 0° C., and was added (1R,2R)-1-phenylpropylene oxide (2.3 g, 17 mmol), and the reaction was allowed to warm to room temperature overnight. The reaction mixture was partitioned between EtOAc (100 mL) and water (100 mL). The organic layer was separated and the aqueous layer extracted with EtOAc (2×100 mL). The combined organic extracts were dried over anhydrous MgSO₄, filtered, and concentrated to dryness, and the residue was purified by flash column chromatography on silica gel eluted with 10 to 40% EtOAc in hexane to afford the title compound. ¹H NMR (500 MHz, CD₃OD): δ 8.28 (d, 1H), 7.59 (dd, 1H), 7.25-7.12 (m, 5H), 7.05 (d, 1H), 4.03 (m, 1H), 3.29 (dd, 1H), 3.19 (dd, 1H), 3.12 (m, 1H), 1.12 (d, 3H).

Step C 2(S)-Azido-4-(5-chloro-2-pyridyl)-3(S)-phenylbutane

To a mixture of 4-(5-chloro-2-pyridyl)-3-phenyl-2-butanol (Step B, 0.24 g, 0.92 mmol), triphenylphosphine (1.5 g, 1.4 mmol) and diphenylphosphoryl azide (0.30 mL, 1.4 mmol) in 5 mL anhydrous THF was added diethylazodicarboxylate (0.24 mL, 1.4 mmol). After stirring at room temperature overnight, the resulting mixture was concentrated with silica gel (10 g) and the residue was loaded onto a silica gel column. Elution with 5 to 15% EtOAc in hexane afforded the title compound. ¹H NMR (500 MHz, CD₃OD): δ 8.35 (d, 1H), 7.52 (dd, 1H), 7.25-7.05 (m, 5H), 6.95 (d, 1H), 3.81 (m, 1H), 3.48 (m, 1H), 3.15-3.05 (m, 2H), 1.14 (d, 3H).

Step D N-[3-(5-Chloro-2-pyridyl)-2(S)-phenyl-1(S)-methylpropyl]amine, hydrochloride The product of Step C (0.20 g, 0.70 mmol) was converted to the title compound following the procedure described in Reference Example 10, Steps H-I, except hydrogen chloride in dioxane (4 M) was used in place of hydrogen chloride in EtOAc. ¹H NMR (500 MHz, CD₃OD): δ 8.75 (d, 1H), 8.19 (dd, 1H), 7.55 (d, 1H), 7.4-7.2 (m, 5H), 3.78 (m, 1H), 3.62 (dd, 1H), 3.48 (m, 1H), 3.43 (dd, 1H), 1.22 (d, 3H). LC-MS: m/e 261 (M+H)⁺ (2.2 min).

REFERENCE EXAMPLE 40

N-[2-(3-Bromophenyl)-3-(5-chloro-2-pyridyl)-1-methylpropyl]amine hydrochloride (Diastereomer α)

Step A 3-Bromophenylacetone

To a solution of N-methoxy-N-methylacetamide (10 g, 100 mmol) in 100 mL anhydrous ether at 0° C. was added 3-bromobenzylmagnesium bromide (0.25 M in ether, 200 mL, 50 mmol). The reaction was allowed to warm to room temperature overnight and was quenched by the addition of saturated ammonium chloride (100 mL). The organic layer was separated and the aqueous layer was extracted with hexane (100 mL). The combined extracts were dried over anhydrous MgSO₄, filtered and concentrated to dryness to afford the title compound. ¹H NMR (500 MHz, CD₃OD): δ 7.45-7.40 (m, 2H), 7.26 (t, 1H), 7.19 (d, 1H), 2.20 (s, 3H).

Step B 3-(3-Bromophenyl)-4-(5-chloro-2-pyridyl)-2-butanone

A suspension of 5-chloro-2-methylpyridine (Reference Example 18, Step A, 6.4 g, 50 mmol) and N-bromosuccinimide (12.5 g, 70 mmol) in 100 mL carbon tetrachloride was heated to gentle reflux (bath temperature 90° C.), and 2,2'-azobisisobutyronitrile (0.74 g) was added in several portions over 30 min. After stirring at this temperature for 5 h, the reaction mixture was concentrated. The resulting slurry was diluted with EtOAc (100 mL) and was washed with water (100 mL), saturated aqueous sodium bicarbonate/saturated aqueous sodium thiosulfate, and brine. The organic solution was dried over anhydrous sodium sulfate, filtered, and concentrated to dryness, and the residue was purified by flash column chromatography on silica gel eluted with 2 to 15% ether in CH₂Cl₂/hexane (1:1) to afford 2-bromomethyl-5-chloropyridine (6.0 g, 60%), which was used immediately for the ensuing reaction. Thus, to a vigorously stirred solution of 2-bromomethyl-5-chloropyridine (6.0 g, 29 mmol) and 3-bromophenyl acetone (Step A, 6.0 g, 28 mmol) and tetrabutylammonium iodide (20 mg) in 30 mL CH₂Cl₂ at −78° C. was added cesium hydroxide monohydrate (10 g, 60 mmol), and the reaction was allowed to slowly warm to room temperate overnight. The reaction mixture was partitioned between EtOAc (100 mL) and water (100 mL). The organic layer was separated and the aqueous layer extracted with EtOAc (2×100 mL). The combined organic extracts were dried over anhydrous sodium sulfate, filtered, and concentrated to dryness, and the residue was purified by flash column chromatography on silica gel eluted with 5 to 40% EtOAc in hexane to afford the title compound. ¹H NMR (500 MHz, CD₃OD): δ 8.44 (d, 1H), 7.66 (dd, 1H), 7.46-7.41 (m, 2H), 7.24 (t, 1H), 7.22 (d, 1H), 7.15 (d, 1H), 4.42 (dd, 1H), 3.54 (dd, 1H), 3.07 (dd, 1H), 2.12 (s, 3H). LC-MS: m/e 338 (M+H)⁺ (3.0 min).

Step C 3-(3-Bromophenyl)-4-(5-chloro-2-pyridyl)-2-butanol

To a solution of 3-(3-bromophenyl)-4-(5-chloro-2-pyridyl)-2-butanone (Step B, 6.7 g, 20 mmol) in 50 mL anhydrous THF at −78° C. was added lithium tri(sec-butyl)borohydride (1.0 M in THF, 30 mL, 30 mmol), and the reaction was allowed to warm to room temperature overnight. The reaction was cooled to 0° C., and was carefully added 2 M hydrochloric acid (50 mL), and the resulting mixture was partitioned between hexane (200 mL) and water (200 mL). The aqueous layer was separated and the organic layer extracted with 2 M hydrochloric acid (2×100 mL). The combined aqueous extracts were neutralized with 5 N aqueous sodium hydroxide (pH>12), and was extracted with EtOAc (2×200 mL). The combined extracts were dried over anhydrous sodium sulfate, filtered, and concentrated to dryness to afford the title compound.

Step D N-[2-(3-Bromophenyl)-3-(5-chloro-2-pyridyl)-1-methlropyl]amine, hydrochloride The product of Step C was converted to the title compound following the procedure described in Reference Example 39, Steps C-D. LC-MS: m/e 338 (M+H)⁺ (2.3 min).

REFERENCE EXAMPLE 41

N-[3-(5-Chloro-2-pyridyl)-2-(3-chlorophenyl)-1-methylpropyl]amine hydrochloride (Diastereomer α)

The title compound was prepared following the procedure described in Reference Example 28 substituting 2-(N-tert-butoxycarbonyl)amino-3-bromophenyl-4-(4-chlorophenyl)butane with 2-(N-tert-butoxycarbonyl)amino-3-bromophenyl-4-(5-chloro-2-pyridyl)butane (intermediate of Reference Example 40, Step D) at Step A. LC-MS: m/e 295 (M+H)+ (2.0 min).

REFERENCE EXAMPLE 42

N-[2-(5-Bromo-2-pyridyl)-3-(4-chlorophenyl)-1-methylpropyl]amine hydrochloride (Diastereomer α)

Step A 5-Bromo-3-pyridylacetone

A mixture of 3,5-dibromopyridine (50 g, 0.21 mol), isopropenyl acetate (26 mL, 0.23 mmol), tris(dibenzylideneacetone)dipalladium (1.0 g, 1.1 mmol) and 2-(diphenylphosphino)-2'(N,N-dimethylamino)biphenyl (1.6 g, 4.2 mmol) in 400 mL toluene was heated at 100° C. under nitrogen for 2 h. The reaction mixture was cooled to room temperature, and was concentrated to about 100 mL. The resulting mixture was loaded onto a silica gel column, which was eluted with 0 to 60% EtOAc in hexane to afford the title compound. $^1$H NMR (500 MHz, CD$_3$OD): δ 8.54 (br s, 1H), 8.33 (br s, 1H), 7.88 (br s, 1H), 3.90 (s, 2H), 2.25 (s, 3H).

Step B 3-(5-Bromo-3-pyridyl)-4-(4-chlorophenyl)-2-butanol

The title compound was prepared following the procedures described in Reference Example 40, Step B-C, substituting 2-bromomethyl-5-chloropyridine with 4-chlorobenzyl chloride and 3-bromophenylacetone with 5-bromo-3-pyridylacetone (Step A). $^1$H NMR (500 MHz, CD$_3$OD): δ 8.43 (d, 1H), 8.24 (d, 1H), 7.98 (dd, 1H), 7.17 (d, 2H), 7.07 (d, 2H), 4.04 (m, 1H), 3.16 (dd, 1H), 3.0-2.9 (m, 2H), 1.04 (d, 3H).

Step C N-[2-(5-Bromo-3-pyridyl)-3-(4-chlorophenyl)-1-methylpropyl]amine hydrochloride (Diastereomer α)

The title compound was prepared following the procedure described for Reference Example 11, Step B. LC-MS: m/e 339 (M+H)+ (2.5 min).

REFERENCE EXAMPLE 43

N-[2-(5-Bromo-3-pyridyl)-3-(4-fluorophenyl)-1-methylpropyl]amine hydrochloride (Diastereomer α)

The title compound was prepared following the procedure described for Reference Example 42 substituting 4-chlorobenzyl chloride with 4-fluorobenzyl chloride at Step B. LC-MS: m/e 323 (M+H)+ (2.3 min).

REFERENCE EXAMPLE 44

N-[3-(4-Chlorophenyl)-2-(5-cyano-3-pyridyl)-1-methylpropyl]amine hydrochloride (Diastereomer α)

Step A 5-Cyano-3-pyridylacetone

The title compound was prepared following the procedure described for Reference Example 42 substituting 3,5-dibromopyridine with 5-bromonicotinonitrile (5-bromo-3-cyanopyridine) at Step A. $^1$H NMR (400 MHz, CD$_3$OD): δ 8.89 (d, 1H), 8.60 (d, 1H), 8.02 (t, 1H), 3.98 (s, 2H), 2.24 (s, 3H).

Step B N-[3(4-Chlorophenyl)-2-(5-cyano-2-pyridyl)-1-methylpropyl]amine hydrochloride (Diastereomer α/β 5:1)

The title compound was prepared following the procedure described for Reference Example 19 substituting 3-pyridylacetone with 5-cyano-3-pyridylacetone (Step A). LC-MS: m/e 286 (M+H)+ (1.9 min).

REFERENCE EXAMPLE 45

N-[2-(5-Cyano-3-pyridyl)-3-(4-fluorophenyl)-1-methylpropyl]amine hydrochloride (Diastereomer α)

The title compound was prepared following the procedure described for Reference Example 44 substituting 4-chlorobenzyl chloride with 4-fluorobenzyl chloride at Step B. LC-MS: m/e 270 (M+H)+ (2.2 min).

REFERENCE EXAMPLE 46

N-[2-(5-Cyano-3-pyridyl)-3-(3,4-difluorophenyl)-1-methylpropyl]amine hydrochloride (Diastereomer α)

The title compound was prepared following the procedure described for Reference Example 44 substituting 4-fluorobenzyl chloride with 3,4-difluorobenzyl chloride at Step B. LC-MS: m/e 288 (M+H)+ (2.3 min).

REFERENCE EXAMPLE 47

N-[3-(3-Chlorophenyl)-2-(5-cyano-3-pyridyl)-1-methylpropyl]amine hydrochloride (Diastereomer α)

The title compound was prepared following the procedure described for Reference Example 44 substituting 4-fluorobenzyl chloride with 3-chlorobenzyl chloride at Step B. LC-MS: m/e 286 (M+H)+ (2.4 min).

REFERENCE EXAMPLE 48

N-[3-(4-Chlorophenyl)-2-(5-chloro-3-pyridyl)-1-methylpropyl]amine hydrochloride (Diastereomer α)

Step A 5-Chloro-3-pyridylacetone

The title compound was prepared following the procedure described for Reference Example 42 substituting 3,5-dibromopyridine with 3,5-dichloropyridine and 2-(diphenylphosphino)-2'(N,N-dimethylamino)biphenyl with 2-(di-t-butylphosphino) biphenyl at Step A. $^1$H NMR (500 MHz, CD$_3$OD): δ 8.42 (d, 1H), 8.27 (d, 1H), 7.73 (dd, 1H), 3.90 (s, 2H), 2.25 (s, 3H).

Step B N-[3-(4-Chlorophenyl)-2-(5-chloro-3-pyridyl)-1-methylpropyl]amine hydrochloride (Diastereomer α)

The title compound was prepared following the procedure described for Reference Example 42, Step B-C substituting 5-bromo-3-pyridylacetone with 5-chloro-3-pyridylacetone at Step B. LC-MS: m/e 295 (M+H)$^+$ (1.9 min).

REFERENCE EXAMPLE 49

N-[2-(5-Chloro-3-pyridyl)-3-(4-fluorophenyl)-1-methylpropyl]amine hydrochloride (Diastereomer α)

The title compound was prepared following the procedure described for Reference Example 48 substituting 4-chlorobenzyl chloride with 4-fluorobenzyl chloride at Step B. LC-MS: m/e 279 (M+H)$^+$ (2.3 min).

REFERENCE EXAMPLE 50

2-Amino-3-(5-chloro-3-pyridyl)-5-methylhane, Hydrochloride Salt (Diastereomer α/β 6:1)

The title compound was prepared following the procedure described for Reference Example 48 substituting 4-chlorobenzyl chloride with 1-iodo-2-methylpropane at Step B. LC-MS: m/e 227 (M+H)$^+$ (2.2 min).

REFERENCE EXAMPLE 51

N-[2-(5-Chloro-3-pyridyl)-3-cyclobutyl-1-methylpropyl]amine hydrochloride (Diastereomer α/β 6:1)

The title compound was prepared following the procedure described for Reference Example 48 substituting 4-chlorobenzyl chloride with (bromomethyl)cyclobutane at Step B. LC-MS: m/e 239 (M+H)$^+$ (2.3 min).

REFERENCE EXAMPLE 52

N-[3-(4-Chlorophenyl)-2-(3-cyanophenyl)-1-methylpropyl]amine hydrochloride (Diastereomer α)

Step A 3-Cyanophenylacetone

The title compound was prepared following the procedure described for Reference Example 28 substituting 3,5-dibromopyridine with 3-bromobenzonitrile and 2-(diphenylphosphino)-2'-(N,N-dimethylamino)biphenyl with 2-(dicyclohexylphosphino)-2'-(N,N-dimethylamino)biphenyl at Step A. $^1$H NMR (500 MHz, CD$_3$OD): δ 7.6 (m, 1H), 7.56 (br s, 1H), 7.50-7.48 (m, 2H), 3.88 (s, 2H), 2.21 (s, 3H).

Step B N-[3-(4-Chlorophenyl)-2-(3-cyanophenyl)-1-methylpropyl]amine hydrochloride (Diastereomer α)

The title compound was prepared following the procedures described for Reference Example 42 substituting 5-bromo-3-pyridylacetone with 3-cyanophenylacetone at Step B. LC-MS: m/e 285 (M+H)$^+$ (2.2 min).

REFERENCE EXAMPLE 53

N-[3-(4-Chlorophenyl)-2-(5-fluoro-3-pyridyl)-1-methylpropyl]amine hydrochloride (Diastereomer α)

Step A 5-fluoro-3-pyridylacetone

The title compound was prepared following the procedure described for Reference Example 42 substituting 3,5-dibromopyridine with 3-fluoro-5-trifluoromethanesulfonyloxypyridine (prepared form 3-fluoro-5-hydroxypyridine and triflic anhydride) and 2-diphenylphosphino)-2'(N,N-dimethylamino)biphenyl with 2-(dicyclohexylphosphino)-2'(N,N-dimethylamino)biphenyl at Step A. $^1$H NMR (500 MHz, CD$_3$OD): δ 8.34 (d, 1H), 8.22 (br s, 1H), 7.50 (ddd, 1H), 3.93 (s, 2H), 2.25 (s, 3H).

Step B N-[3-(4-Chlorophenyl)-2-(5-chloro-3-pyridyl)-1-methylpropyl]amine hydrochloride (Diastereomer α)

The title compound was prepared following the procedure described for Reference Example 42, Step B-C substituting 5-bromo-3-pyridylacetone with 5-fluoro-3-pyridylacetone at Step B. LC-MS: m/e 279 (M+H)$^+$ (2.4 min).

REFERENCE EXAMPLE 54

N-[3-(4-Chlorophenyl)-2-(5-methyl-3-pyridyl)-1-methylpropyl]amine hydrochloride (Diastereomer α)

The title compound was prepared following the procedure described for Reference Example 28 substituting 2-(N-tert-butoxycarbonyl)amino-3-(3-bromophenyl)-4-(4-chlorophenyl)butane with 2-(N-tert-butoxycarbonyl)amino-3-(5-bromo-3-pyridyl)-4-(4-chlorophenyl)butane (intermediate of Reference Example 42, Step B) at Step A. LC-MS: m/e 275 (M+H)$^+$ (1.3 min).

REFERENCE EXAMPLE 55

N-[2-(3-Bromo-5-fluorophenyl)-3-(4-Chlorophenyl)-1-methylpropyl]amine hydrochloride (Diastereomer α)

Step A 3-Bromo-5-fluorophenylacetone

The title compound was prepared following the procedure described for Reference Example 42 substituting 3,5-dibromopyridine with 1,3-dibromo-5-fluorobenzene and 2-(diphenylphosphino)-2'-(N,N-dimethylamino)biphenyl with 1,1'-bis(diphenylphosphino)ferrocene at Step A. $^1$H NMR (500 MHz, CD$_3$OD): δ 7.23 (d, 1H), 7.22 (s, 1H), 6.96 (d, 1H), 3.81 (s, 2H), 2.20 (s, 3H).

Step B N-[2-(3-Bromo-5-fluorophenyl)-3-(4-chlorophenyl)-1-methylpropyl]amine hydrochloride (Diastereomer α)

The title compound was prepared following the procedure described for Reference Example 42, Steps B-C substituting 5-bromo-3-pyridylacetone with 3-bromo-5-fluorophenylacetone (Step A). LC-MS: m/e 356 (M+H)$^+$ (2.9 min).

REFERENCE EXAMPLE 56

N-[2-(3-Bromo-5-fluorophenyl)-3-(4-fluorophenyl)-1-methylpropyl]amine hydrochloride
(Diastereomer α)

The title compound was prepared following the procedures described for Reference Example 55 substituting 4-chlorobenzyl chloride with 4-fluorobenzyl chloride at Step B. LC-MS: m/e 340 (M+H)$^+$ (2.8 min).

REFERENCE EXAMPLE 57

2-Amino-3-indolin-N-yl-4(4-chloro)phenylbutane

Step A. Ethyl 3-(4-chlorophenyl)-2-indolin-N-ylpropanoate

In an oven-dried flask under an atmosphere of nitrogen, 1.1 g LiOH.H$_2$O (26.25 mmol) in DMF (20 mL) was added to a stirring suspension of 4 angstrom molecular sieves. After 30 minutes of stirring at room temperature 2.8 mL (25 mmol) indoline was added dropwise. After one hour at room temperature 2.9 mL (26.25 mmol) Ethyl bromoacetate was added dropwise. After 1.5 h the solid material was filtered and the residue was washed with copious amounts of EtOAc. The organics were washed 3 times with water and the organic material was dried over MgSO$_4$. The solvents were evaporated under reduced pressure. The crude material was then dissolved in 75 mL anhydrous THF, charged into an oven dried round bottom under an atmosphere of nitrogen, cooled to −78° C., and then treated with 26.25 mL a 1M solution of NaHMDS. The solution was allowed to stir for 30 minutes at −78° C. after which the enolate was quenched with 5.4 g (26.25 mmol) of parachlorobenzyl bromide (solution in 25 mL anhydrous THF). The reaction was allowed to warm to room temperature overnight. The next day the reaction was quenched with water. The aqueous layer was extracted with 3 large portions of EtOAc. The combined organics were dried over MgSO$_4$. The solvents were removed under reduced pressure and the residue was purified by flash chromatography which yielded the title compound as a yellow oil. LC/MS m/e=331 (M+1). TLC R$_f$=0.22 (20:1 hexanes:EtOAc). $^1$H NMR (500 MHz, CDCl$_3$): δ 1.11 (t, J=3.55 Hz, 3H), 2.96 (m, 2H), 3.06 (m, 1H), 3.25 (m, 1H), 3.60 (t, 2H), 4.07 (m, 2H), 4.36 (t, J=3.75 Hz, 1H).

Step B. N,O-dimethyl-3-(4-chlorophenyl)-2-indolin-N-ylpropanamide

In an oven-dried flask under an atmosphere of nitrogen, 11.75 mL 1 M solution of (CH$_3$)$_2$AlCl in CH$_2$Cl$_2$ was added via addition funnel to a stirring suspension of 1.15 g (11.75 mmol) N,O-dimethylhydroxylamine hydrochloride at 0° C. After warming to room temperature a solution of 970 mg (2.94 mmol) of Ethyl 3-(4-chlorophenyl)-2-indolinylpropanoate in 10 mL was added via addition funnel. After stirring at room temperature for 5 h, 35 mL pH=8 phosphate buffer solution was added and the resulting solution was stirred vigorously for 30 minutes. The phases were separated and the aqueous layer was extracted 2 times with chloroform. The combined organics were washed with water and then dried over MgSO$_4$. The product was collected as a brown oil. The crude material was carried on to the next step.). TLC R$_f$=0.12 (10:1 hexanes:EtOAc). $^1$H NMR (500 MHz, CDCl$_3$): δ 2.83 (m, 1H), 2.97 (m, 2H), 3.13 (s, 3H), 3.34 (m, 1H), 3.45 (s, 3H), 3.61 (m, 2H), 4.87 (b, 1H), 6.54 (d, 1H), 6.66 (t, J=7.1 Hz, 1H), 7.07 (t, J=7.1 Hz, 2H), 7.18 (d, J=8.5 Hz, 2H), 7.24 (d, J=8.5 Hz, 2H)

Step C. 4-(4-chlorophenyl)-3-indolin-N-ylbutan-2-one

In an oven dried flask under an atmosphere of nitrogen, 2.8 mL 1 M solution of CH$_3$MgBr in THF was added dropwise to a stirring solution of N,O-dimethyl-3-(4-chlorophenyl)-2-indolinylpropanamide in 25 mL anhydrous THF. The solution was stirred for 4 h while being allowed to warm to room temperature. Then approximately 20 mL water was added. The solution was extract three times with 50 mL ether. The combined extracts were dried over MgSO$_4$. The solvents were removed under reduced pressure yielding a brown oil which was carried on to the next step without purification. LC/MS m/e=301 (M+1). TLC R$_f$=0.5 (4:1 hexanes:EtOAc). $^1$H NMR (500 MHz, CDCl$_3$): δ 2.14 (s, 3H), 2.81 (dd, J=14.6, 6.6 Hz, 1H), 2.97 (t, J=8.5 Hz, 2H), 3.26 (m, 2H), 3.5 (m, 1H), 4.21 (dd, J=6.6, 6.6 Hz), 6.39 (d, J=8 Hz, 1H), 6.66 (dd, J=7, 7 Hz, 1H), 7.07 (m, 2H), 7.13 (d, J=8.5 Hz), 7.22 (d, J=8.3 Hz).

Step D. 4-(4-chlorophenyl)-3-indolin-N-ylbutan-2-one methoxime

A solution of 472 mg (1.573 mmol) of the product of Step C and 263 mg (3.147 mmol) of methoxylamine hydrochloride in anhydrous ethanol was treated with 255 μL (3.147 mmol) of pyridine. The solution was stirred for 2 h at room temperature. Solvent was removed under reduced pressure and the residue was partitioned between water and ether. The water was extracted with ether again. The extracts were then combined and dried over MgSO$_4$, filtered and concentrate to obtain crude material. obtained. Both the E and Z isomers were carried onto the next step. LC/MS m/e=330 (M+1). TLC R$_f$=0.77 and 0.65 (4:1 hexanes:EtOAc). $^1$H NMR (500 MHz, CDCl$_3$): δ 1.78 (2s, 1H), 2.88 (dd, J=6.2, 13.8 Hz, 1H), 2.95 (m, 2H), 3.30 (m, 2H), 3.45 (m, 1H), 3.75 and 3.89 (2s, 3H), 4.21 (dd, J=6.9, 7.8 Hz, 1H), 6.28 and 6.47 (2d, J=8.1, 1H), 6.61 (m, 1H), 7.02 (m, 2H), 7.22 (m, 4H).

Step E. 2-Amino-3-indolin-N-yl-4(4-chloro)phenylbutane

In an oven-dried flask equipped with a water condenser under an atmosphere of nitrogen, a solution of 301 mg (0.914 mmol) 4-(4-chlorophenyl)-3-indolinylbutan-2-one methoxime in 1.5 mL anhydrous THF was treated with 3.7 mL (3.7 mmol) of 1M B$_3$.THF at room temperature. The solution was then heated to 75° C. for 2 days. The solution was then cooled to 0° C. and treated with chips of ice until bubbling subsided 500 μL of 20% KOH were then added and the solution was heated at 45° C. for 2 h. The solution was then cooled to room temperature and extracted with ether 3×. The combined extracts were dried over MgSO$_4$, filtered, and concentrated to afford crude amine which was used in the next experiment without further purification. LC/MS m/e=302 (M+1). $^1$H NMR (500 MHz, CDCl$_3$): δ 1.13, 1.14 (2d, J=6.5 Hz, 1H), 1.55-1.60 (m, 2H), 2.80-3.10 (m, 4H), 3.30-3.60 (m, 2H), 6.348 and 6.38 (2d, J=7.9 Hz, 1H), 6.50-6.78 (m, 2H), 6.95-7.24 (m, 5H)

REFERENCE EXAMPLE 58

2-Amino-3-indol-N-yl-4(4-chloro)phenylbutane

This compound was prepared in an analogous manner to Reference Example 57 except that during Step A, sodium hydride was used as the base instead of the lithium hydroxide monohydrate/molecular sieves combination and indole was substituted for indoline. LC/MS: calc'd for $C_{18}H_{19}ClN_2$ 299, observed m/e 300 $(M+H)^+$ (2.4 min).

REFERENCE EXAMPLE 59

2-Amino-3-(N-methyl, N-phenyl)amino-4(4-chloro)phenylbutane

This compound was prepared in an analogous manner to Reference Example 57, substituting N-methylaniline for indoline in Step A. LC/MS: calc'd for $C_{17}H_{21}ClN_2$ 289, observed m/e 290 $(M+H)^+$ (2.4 min).

REFERENCE EXAMPLE 60

2-Amino-3-(7-azaindol-N-yl)-4(4-chloro)phenylbutane

This compound was prepared in an analogous manner to Reference Example 57, substituting 7-aza-indole for indole in Step A. LC/MS: calc'd for $C_{17}H_{18}ClN_3$ 300, observed m/e 301 $(M+H)^+$ (2.7 min).

REFERENCE EXAMPLE 61

2-Amino-3-(benzisoxazol-3-yl)-4(4-chloro)phenylbutane

This compound was prepared in an analogous manner to Reference Example 57 except starting with ethyl(benzisoxazol-3-yl)acetate in Step B. LC/MS: calc'd for $C_{17}H_{17}ClN_2O$ 300, observed m/e 301 $(M+H)^+$ (2.2 min).

REFERENCE EXAMPLE 62

4-(4-Methylphenyl)-3-phenylbutan-2-amine (mixture of 4 isomers)

Step A 1-Phenylacetone

To a solution of N-methyl-N-methoxyacetamide (9.9 mL. 97 mmol) in ether (300 mL) at 0° C. was added benzylmagnesium chloride (97 mL a 1M solution in ether). The cloudy, white reaction mixture was warmed to room temperature for 2 h and then quenched by careful addition of 1N hydrochloric acid (100 mL). The organic phase was separated, washed with brine, dried over $MgSO_4$ and concentrated. The crude material was purified by column chromatography on silica gel eluting from 0-10% EtOAc/hexane to give the title compound. $^1$H NMR (500 MHz, CDCl$_3$): δ 7.36 (t, J=7.1 Hz, 2H), 7.30 (t, J=7.3 Hz, 1H), 7.24 (d, J=7.3 Hz, 2H), 3.72 (s, 2H), 2.18 (s, 3H). LC-MS: m/e 135 $(M+H)^+$ (1.95 min).

Step B 4-(4-Methylphenyl)-3-phenylbutan-2-one

1-Phenylacetone (200 mg, 1.49 mmol) was mixed with powdered potassium hydroxide (167 mg, 2.98 mmol) and tetra-n-butylammonium bromide (1 mol %, 5 mg) in a flask without solvent. This mixture was stirred at room temperature for 90 min. before the addition of 1-chloromethyl)-4-methylbenzene (198 µl, 1.49 mmol). The reaction mixture was then stirred overnight before diluting with water and $CH_2Cl_2$. The aqueous layer was separated and neutralized to pH 7 with 2N hydrochloric acid and extracted again into $CH_2Cl_2$. The combined organic washes were dried with $MgSO_4$ and concentrated. The crude material was purified by column chromatography on silica gel eluting from 0-10% EtOAc/hexane to give the title compound. $^1$H NMR (500 MHz, CDCl$_3$): δ 7.35 (t, J=7.0 Hz, 2H), 7.29 (t, J=7.4 Hz, 1H), 7.23 (d, J=7.1 Hz, 2H), 7.05 (d, 7.8 Hz, 2H), 6.98 (d, J=7.8 Hz, 2H), 3.94 (t, J=7.3 Hz, 1H), 3.43 (dd, J=13.9, 7.5 Hz, 1H), 2.91 (dd, J=14, 7.1 Hz, 1H), 2.32 (s, 3H), 2.08 (s, 3H). LC-MS: m/e 239 $(M+H)^+$ (3.61 min).

Step C 4-(4-Methylphenyl)-3-phenylbutan-2-amine

To a solution of the 4-(4-methylphenyl)-3-phenylbutan-2-one (308 mg, 1.29 mmol) in 7M ammonia in MeOH (5 mL) and acetic acid (3 mL) was added sodium cyanoborohydride (130 mg, 2.06 mmol) and the reaction stirred at room temperature overnight. The reaction was quenched by pouring into 2M sodium carbonate solution and extracted into EtOAc. The aqueous layer was salted and re-extracted. The combined organic extracts were dried over $MgSO_4$ and concentrated to give the title compound as a mixture of 4 isomers which was used without further purification. LC-MS: m/e 240 $(M+H)^+$ (2.22 min).

REFERENCE EXAMPLE 63

4-(4-Methoxyphenyl-3-phenylbutan-2-amine

Prepared using the procedures described in Example 62, Steps A-C, using 1-(chloromethyl)-4-methoxybenzene as the alkylating agent in Step B. LC-MS: m/e 256 $(M+H)^+$ (1.90 and 2.03 min).

REFERENCE EXAMPLE 64

3-[2-Amino-1-(4-fluorobenzyl)propyl]benzonitrile

Prepared using the procedures described in Example 10 using 3-(2-oxopropyl)benzonitrile and 1-(chloromethyl)-4-fluorobenzene as the reactants in Step B. LC-MS: m/e 269 $(M+H)^+$ (2.87 min).

REFERENCE EXAMPLE 65

N-[2-Phenyl-3-(4-fluorophenyl)-1-methylpropyl]amine hydrochloride (Diastereomer α)

The title compound was obtained by the method described in Reference Example 26, substituting 4-fluorobenzyl bromide for isobutyl iodide. LC-MS, $R_t$=2.2 min, m/e=244.

REFERENCE EXAMPLE 66

2-(2,3-Dihydro-1-H-indol-1-yl)-1,4-dimethylpentylamine

Step A Ethyl (2-(2,3-dihydro-1H-indol-1-yl)-4-methylpentanoate

A solution of 0.53 g (3.3 mmol) of ethyl (S)-2-hydroxyisocaproate in 8 mL dry $CH_2Cl_2$ was cooled in a −78° C. bath and 0.73 mL (4.34 mmol) of triflic anhydride and 0.6 mL (5.36 mmol) of 2,6 lutidine were added. After 15 min 2 mL (11.5 mmol) of diisopropylethylamine was added and stirred for 10 min. To this solution 0.36 mL (3.21 mmol) of 2,3-dihydroindoline was added and stirred overnight as it slowly warmed to room temperature. The reaction was quenched with saturated NaHCO$_3$ solution and extracted with ether. The combined organic layer was washed with water, brine, dried and concentrated. The residue was purified on a flash column using a gradient of 5-10% EtOAc/hexane to isolate the title compound. $^1$H NMR: (500 MHz, CDCl$_3$): δ 0.99 (d, 3H), 1.03 (d, 3H), 1.22 (t, 3H), 1.81 (m, 3H), 3.04 (m, 2H), 3.57 (m, 1H), 3.66 (m, 1H), 4.14 (q, 2H), 4.24 (t, 1H), 6.4-7.1 (m, 4H).

Step B 3-(2,3-Dihydro-1H-indol-1-yl)-5-methyl-hexan-2-one

To a solution of 0.54 g (2.07 mmol) of ethyl (2-(2,3-dihydro-1H-indol-1-yl)-4-methylpentanoate in 10 mL CH$_2$Cl$_2$, 1.98 g (10 mmol) of N,O-dimethylhydroxylamine hydrochloride and 1.4 mL triethylamine were added. The mixture was cooled in an ice bath and 10 mL (10 mmol) 1 M diethylaluminum chloride in toluene was added. The reaction was stirred overnight as it warmed to room temperature then carefully quenched by pouring into 1.2 N HCl. The solution was extracted with CH$_2$Cl$_2$. The organic layer was washed with brine, dried and concentrated leaving amide which was used without purification. This amide was dissolved in 5 mL THF and 2.5 mL (3.5 mmol) of 1.4 M methylmagnesium bromide was added. After 1 h, the solution was quenched with 1.2 N HCl and extracted with EtOAc. The EtOAc layer was washed with brine, dried and concentrated. The residue was chromatographed using a gradient of 5-10% EtOAc-hexane to isolate the title compound. $^1$H NMR: (500 MHz, CDCl$_3$): δ 0.96 (d, 3H), 0.99 (d, 3H), 1.7 (m, 3H), 2.17 (s, 3H), 3.06 (m, 2H), 3.04 (q, 1H), 3.52 (m, 1H), 4.11 (m, 1H) 6.4-7.1 (m, 4H).

Step C 2-(2,3-Dihydro-1-H-indol-1-yl)-1,4-dimethylpentylamine

To a solution of 0.185 g (0.8 mmol) of 3-(2,3-dihydro-1H-indol-1-yl)-5-methylhexan-2-one in 2 mL ethanol, 0.135 g O-methylhydroxylamine hydrochloride and 0.13 mL (1.6 mmol) of pyridine were added. After stirring for 2 h, the solution was concentrated and the residue was partitioned between water and EtOAc. The organic layer was washed with brine, dried and concentrated to give 0.2 g O-methyloxime as a mixture of isomers. This mixture was dissolved in 2 mLTHF and 1.5 mL 1 M B$_3$ in THF was added. After gas evolution ceased, the reaction was heated in a 50° C. bath. After 2 h another 1.5 mL 1 M B$_3$ in THF was added and heating was continued overnight. The reaction mixture was cooled and quenched with MeOH and concentrated. The residue was dissolved in 6 mL CH$_2$Cl$_2$ and 2 mL 1 N NaOH was added. After stirring for 15 min the layers were separated and the aqueous layer was extracted with CH$_2$Cl$_2$. The combined organic layer was washed with water, brine dried and concentrated to isolate title compound as a mixture of diastereomers which was used without purification. LC-MS, R$_t$=2.24 min, m/e=233.

The following amines were synthesized by the method of Reference Example 66.

| Reference Example | Name | LC/MS |
|---|---|---|
| 67 | 3-Cyclobutyl-2-(3,4-dihydroquinoline-1(2H)-yl)-1-methylpropylamine | R$_t$= 2., 8 min, m/e = 259 |
| 68 | 2-(3,4-Dihydroquinoline-1(2H)-yl)-1,4-dimethylpentylamine | R$_t$= 2.74 min, m/e = 248 |

REFERENCE EXAMPLE 69

2-(1H-1,2,3-Benzotriazol-1-yl)-3-(4-chlorophenyl)-1-methylpropylamine

Step A 2-(1H-1,2,3-Benzotriazol-1-yl)-N-methoxy-N-methylacetamide

A mixture of 1.77 g (10 mmol) of 2-(1H-1,2,3-benzotriazol-1-yl)acetic acid, 1.07 g (11 mmoles) of N,O-dimethylhydroxylamine hydrochloride, 5.8 g (11 mmol) of PyBOP, and 3.4 mL (24.2 mmol) of diisopropylethylamine in 50 mL CH$_2$Cl$_2$ was stirred overnight at RT. This mixture was partitioned between EtOAc and water. The organic layer was washed with brine and dried over anhydrous MgSO4. Solvent removal afforded a crude product which was purified on silica gel using 60% EtOAC in hexane as solvent to give 2.01 g the desired amide as a solid. $^1$H NMR: (CDCl$_3$): δ 3.26 (s, 3H), 3.84 (s, 3H), 5.63 (s, 2H), 7.35-8.2 (m, 4H).

Step B 2-(1H-1,2,3-Benzotriazol-1-yl)-3-(4-chlorophenyl)-N-methoxy-N-methyl-propanamide To a solution of 2.0 g (9 mmol) of 2-(1H-1,2,3-benzotriazol-1-yl)-N-methoxy-N-methylacetamide in 15 mL anhydrous THF at −78° C., 10 mL (10 mmol) of 1M lithium bis(trimethylsilyl)amide was added dropwise. After stirring for 25 min, a solution of 2.06 g (10 mmol) of 4-chlorobenzyl bromide in 2 mL anhydrous THF was added. The resulting reaction mixture was allowed to warm to RT and stirred for 6 h. This reaction was quenched, diluted with 75 mL EtOAc and washed 3 times with 10 mL each of brine. After drying the organic phase solvent removal afforded a crude product which was purified on silica gel using 40% EtOAc in hexane as solvent to afford the desired product as a solid. $^1$H NMR: (CDCl$_3$): δ 3.2 (s, 3H), 3.34 (s, 3H), 3.52 (m, 1H), 3.7 (m, 1H), 6.32 (t, 1H), 6.9-8.2 (m, 8H).

Step C 2-(1H-1,2,3-Benzotriazol-1-yl)-3-(4-chlorophenyl)-butan-2-one

To a solution of 1.73 g (5 mmol) of 2-(1H-1,2,3-benzotriazol-1-yl)-3-(4-chlorophenyl)-N-methoxy-N-methyl-propanamide in 10 mL anhydrous THF at 0° C., 4 mL (10 mmol) of 2.5M methyl magnesium bromide in ether was added. The reaction mixture was stirred for 4 h as it warmed to RT. The reaction was quenched by adding 10 mL 1N HCl and the resulting mixture was partitioned between EtOAc and water. The organic phase was washed with brine and dried over anhydrous MgSO$_4$. Solvent removal gave a crude ketone, which was purified on silica gel using 40% EtOAc in hexane to provide the desired ketone.

Step D 2-(1H-1,2,3-Benzotriazol-1-yl)-3-(4-chlorophenyl)-1-methyl propylamine To a solution of 1.18 g (4 mmol) of 2-(1H-1,2,3-benzotriazol-1-yl)-3-(4-chlorophenyl)-butan-2-one in 8.5 mL (60 mmol) of 7N ammonia in MeOH at 0° C., 4 mL (964 mmol) of glacial acetic acid was added followed by 410 mg (6.5 mmol) of sodium cyanoborohydride. The reaction mixture was allowed to warm to RT and stirred overnight. The reaction was partitioned between EtOAc and saturated NaHCO$_3$ solution. The organic phase was dried over anhydrous MgSO$_4$. The solvent was removed in vacuo and the residue was purified on silica gel using a mixture of 5% 2N methanolic ammonia solution and 95% CH$_2$Cl$_2$ to give the desired amine as a mixture of diastereomers. LC-MS, R$_t$=2.0 min, m/e=301.

REFERENCE EXAMPLE 70

3-(4-Chlorophenyl)-2-(thiophene-3-yl)-1-methylpropylamine

The title amine was prepared by the method described in Reference Example 69, substituting thiophene-3-acetic acid for 2-(1H-1,2,3-benzotriazol-1-yl)acetic acid in Step A. LC-MS, R$_t$=2.19 min, m/e=266.

REFERENCE EXAMPLE 71

3-(4-Chlorophenyl)-2-(thiophene-2-yl)-1-methylpropylamine

Step A 3-(4-Chlorophenyl)-2-(thiophen-2-yl)-butan-2-one

The title compound was obtained from 2-thiopheneacetic acid according to the procedure described in Reference Example 10, Steps A-D.

Step B 3-(4-Chlorophenyl)-2-(thiophene-2-yl)-1-methylpropylamine

This amine was synthesized by the method of Reference Example 69, Step D. LC-MS, R$_t$=2.18 min, m/e=266.

REFERENCE EXAMPLE 72

3-(4-Chlorophenyl)-1-methyl-2-(1-methyl-1H-indol-3-yl)propylamine

The title compound was prepared according to the method described in Reference Example 69. LC-MS: R$_t$=2.5 min, m/e=313.

REFERENCE EXAMPLE 73

3-(4-Chlorophenyl)-1-methyl-2-(1H-indazol-1-yl)propylamine

Step A 3-(4-Chlorophenyl)-2-(1H-indazol-1-yl)-butan-2-one

The title compound was obtained from indazol-1-yl-acetic acid by following the procedure of Reference Example 10, Steps A-D.

Step B 3-(4-Chlorophenyl)-1-methyl-2-(1H-indazol-1-yl)propylamine

The title amine was prepared according to the procedure of Reference Example 69, Step D. LC-MS: Rt=2.24 min, m/e=300.

REFERENCE EXAMPLE 74

3-(4-Chlorophenyl)-1-methyl-2-(1-methyl-1H-indol-4-yl)propylamine

Step A 4-Chloro-1-methylindole

In a 100 mL flask, 0.3 g (7.5 mmol) sodium hydride was washed twice with dry hexane. The solid was suspended in 15 mL dry THF and 1 g (6.6 mmol) 4-chloroindole was drop wise added. After 15 min, 0.5 mL (7.9 mmol) methyl iodide was added and the solution was stirred overnight. The reaction was quenched with 1.2 N HCl and partitioned between ether and water. The organic layer was washed with brine, dried and concentrated keeping the bath temperature below 30° C. The residue was purified on a flash column using a gradient of 5-10% EtOAc/hexane to isolate the desired product. $^1$H NMR: (500 MHz, CDCl$_3$): δ 3.84 (s, 3H), 6.63 (d, 1H), 7-7.3 (m, 4H).

Step B 1-(1-Methyl-1H-indol-4-yl)acetone

To a solution of 0.852 g (5.14 mmol) of 4-chloro-1-methylindole in 15 mL dry toluene, 0.85 mL (7.73 mmol) isopropenyl acetate and 2.3 mL (8 mmol) tributyltin methoxide were added. The solution was heated to 100° C. After 15 min, 0.24 g (0.61 mmol) 2-dicyclohexylphosphino-2'-(N,N-dimethylamino)biphenyl and 0.14 g (0.153 mmol) tris(dibenzylidineacetone)dipalladium were added and heating was continued. After 2 h the solution was cooled, filtered through a pad of CELITE diatomaceous earth and the filtrate was concentrated to ca. 5 mL. This solution was purified on a silica column using a gradient of 5-20% EtOAc/hexane to obtain the title compound. $^1$H NMR: (500 MHz, CDCl$_3$): δ 2.14 (s, 3H), 3.84 (s, 3H), 3.97 (s, 2H), 6.51 (d, 1H), 7-7.3 (m, 4H).

Step C 4-(4-Chlorophenyl)-3-(1-methyl-1H-indol-4-yl)-butan-2-one

To a suspension of 135 mg (3.38 mmol) of sodium hydride in 8 mL dry THF, a solution of 605 mg (3.23 mmol) 1-(1-methyl-1H-indol-4-yl)acetone in 2 mL THF was added. The mixture was stirred for 45 min during which time the sodium hydride dissolved and a yellow orange solution resulted. The reaction was cooled in ice bath and 660 mg (3.24 mmol) 4-chlorobenzyl bromide in 1 mL THF was added. The cold bath was removed and the solution was stirred for 1.5 h. The reaction was quenched with 1.2 N HCl and extracted with EtOAc. The organic layer was washed with brine, dried and concentrated. The residue was chromatographed using a gradient of 10-20% EtOAc/hexane to isolate the desired product. $^1$H NMR: (500 MHz, CDCl$_3$): δ 2.03 (s, 3H), 3.07 (m, 1H), 3.58 (m, 1H), 3.84 (s, 3H), 4.23 (t, 1H), 6.52 (d, 1H), 6.9-7.3 (m, 8H).

Step D 3-(4-Chlorophenyl)-1-methyl-2-(1-methyl-1H-indol-4-yl)propylamine

The title compound was prepared from 4-(4-chlorophenyl)-3-(1-methyl-1H-indol-4-yl)-butan-2-one by following the procedure of Reference Example 106, Step C. LC-MS, Rt=2.4 min, m/e=313.

REFERENCE EXAMPLE 75

3-(4-Chlorophenyl)-1-methyl-2-(pyridazin-3-yl)propylamine

Step A 4-(4-Chlorophenyl)-3-pyridazin-3-yl-butan-2-one

This compound was synthesized from 3-iodopyridazine following Reference Example 42, Steps A-D.

Step B N-2,4-Dimethoxybenzyl-N(3-(4-chlorophenyl)-1-methyl-2-pyridazin-3-yl)propyl)amine A solution of 300 mg (1.15 mmol) 4-(4-chlorophenyl)-3-(pyridazin-3-yl)-butan-2-one in 4 mL dichloroethane was treated with 234 mg (1.15 mmol) 2,4-dimethoxybenzyl amine hydrochloride, 0.16 mL (1.15 mmol) triethylamine and 488 mg (2.3 mmol) sodium triacetoxyborohydride. After stirring the reaction overnight, it was partitioned between water and $CH_2Cl_2$. The organic layer was washed with brine, dried and concentrated and the residue was purified on a flash column using 3% MeOH—$CH_2Cl_2$ to isolate the desired amine.

Step C 3-(4-Chlorophenyl)-1-methyl-2-(pyridazin-3-yl)propylamine

A solution of 300 mg N-2,4-dimethoxybenzyl-N(3-(4-chlorophenyl)-1-methyl-2-(pyridazin-3-yl)propyl)amine in 5 mL trifluoroacetic acid was heated in a 70° C. bath over night followed by 6 h in a 100° C. bath. The reaction was cooled, concentrated and the residue was diluted with EtOAc. This solution was quenched (to pH 10) with 1N NaOH and the layers were separated. The organic layer was washed with brine, dried and concentrated. The residue was purified on a prep TLC using 10% MeOH/$CH_2Cl_2$ with 1% $NH_4OH$ to isolate the title compound (mixture of diastereomers), starting material was also recovered. LC-MS, Rt=1.63 min, m/e=262.

REFERENCE EXAMPLE 76

3-(4-Chlorophenyl)-1-methyl-2-(pyrimidin-5-yl)propylamine

Step A 4-(4-Chlorophenyl)-3-(pyrimidin-5-yl)-butan-2-one

The title compound was obtained from 5-bromopyrimidine following the method of Reference Example 75, Steps A-C except that 2-(di-t-butylphosphino)biphenyl was used in place of dicyclohexylphosphino-2'-(N,N-dimethylamino)biphenyl in Step B.

Step B 3-(4-Chlorophenyl)-1-methyl-2-(pyrimidin-5-yl)propylamine

The title compound was prepared by the procedure described in Reference Example 10, Steps E-I. LC-MS, Rt=1.57 min, m/e=262.

REFERENCE EXAMPLE 77

2-(3-Cyanophenyl)-3-cyclobutyl-1-methylpropylamine

Step A 1-(3-Cyanophenyl)acetone

The title compound was prepared from 3-bromobenzonitrile and isopropenyl acetate by the procedure of Reference Example 42, Step A.

Step B 3-(3-Cyanophenyl)-4-cyclobutyl-butan-2-one

To a solution of 1.45 g (9.07 mmol) of 1-(3-cyanophenyl) acetone in 18 mL acetonitrile, 1.1 mL (9.5 mmol) cyclobutyl bromide and 5.91 g (18.1 mmol) cesium carbonate were added. After heating the solution in a 60° C. bath overnight, it was cooled and filtered. The filtrate was partitioned between water and EtOAc and the aqueous layer was extracted with EtOAc. The combined organic layer was washed with brine, dried and concentrated. The residue was purified on a flash column using a gradient of 5-10% EtOAc/hexane to isolate the title compound. $^1$H NMR: (500 MHz, $CDCl_3$): δ 1.5-2.2 (m, 9H), 2.13 (s, 3H), 3.64 (m, 1H), 7.4-7.7 (m, 4H).

Step C
2-(3-Cyanophenyl)-3-cyclobutyl-1-methylpropylamine

This amine was prepared by following the method of Reference Example 10, Steps E-I. LC-MS, Rt=2.48 min, m/e=229.

The compounds of Reference Examples 78-80 were obtained by procedures described in Reference Example 77.

| Reference Example | Name | LC/MS |
|---|---|---|
| 78 | 2-(3-Cyanophenyl)-3-cyclopropyl-1-methylpropylamine | Rt = 1.8 min, m/e = 215 |
| 79 | 2-(3-Cyanophenyl)-3-cyclopentyl-1-methylpropylamine | Rt = 2.7 min, m/e = 243 |
| 80 | 2-(3-Cyanophenyl)-3-cyclohexyl-1-methylpropylamine | Rt = 2.8 min, m/e = 257 |

REFERENCE EXAMPLE 81

2-(3-Cyanophenyl)-3-(1-tert-butyloxycarbonyl-piperidin-4-yl)-1-methylpropylamine Step A 3-(3-Cyanophenyl)-4-(1-tert-butyloxycarbonyl-piperidin-4-yl)-butan-2-one The title compound was synthesized by the method of Reference Example 77, Steps A-B.

Step B 2-(3-Cyanophenyl)-3-(1-tert-butyloxycarbonyl-piperidin-4-yl)-1-methylpropylamine The title amine was obtained by the method of Reference Example 10, steps E-G except that di-tert-butyl dicarbonate was not added in Step G. LC-MS, Rt=2.72 min, m/e=258 (M−99). (0.70 min).

REFERENCE EXAMPLE 82

N-[3-(4-Chlorophenyl)-2-(3-methylthiophenyl)-1-methylpropyl]amine hydrochloride (Diastereomer α)

The title compound was prepared following the same procedure as described in Example 42 substituting 3,5-dibromopyridine with 3-bromothioanisole at Step A. LC-MS: m/e 306 (M+H)+ (2.68 min).

EXAMPLES 1 AND 2

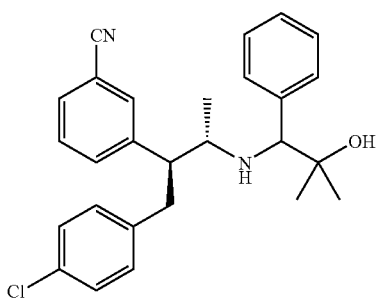

3-(1(S)-(4-Chlorobenzyl)-2(S)-((2-hydroxy-2-methyl-1-phenylpropyl)amino)propyl)benzonitrile (Diastereomer A) and 3-(1(S)-4-Chlorobenzyl)-2(S)-((2-hydroxy-2-methyl-1-phenylpropyl)amino)propyl)benzonitrile. (Diastereomer B)

To a solution of 250 mg (0.877 mmol) of 3-(4-chlorophenyl)-2(S)(3-cyanophenyl)-1(S)-methyl-propylamine in 3 mL of dichloroethane, 134 μL (0.88 mmol) of 2-hydroxy-2-methylpropiophenone and 280 mg (1.32 mmol) of sodium triacetoxyborohydride were added. After stirring for 3 hr, the reaction was quenched with water and the organic layer was removed with a pipet. This layer was purified by prep TLC using 50% EtOAc/hexane as an eluant to isolate 3-(1(S)-(4-chlorobenzyl)-2(S)-((2-hydroxy-2-methyl-1-phenylpropyl)amino)propyl)benzonitrile (diastereomer A) as a higher Rf isomer (LC-MS: m/e=433 (M+1), 3.09 min) and 3-(1(S)-(4-Chlorobenzyl)-2(S)-((2-hydroxy-2-methyl-1-phenylpropyl)amino)propyl)benzonitrile (diastereomer B) as a lower Rf isomer. LC-MS: m/e=433 (M+1), 3.09 min.

EXAMPLE 3

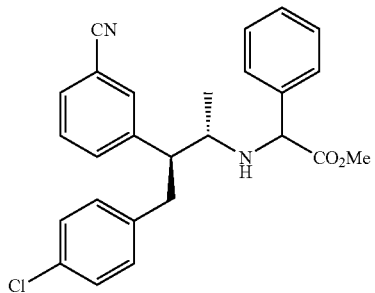

Methyl ((3-(4-Chlorophenyl)-2(S)-(3-cyanophenyl)-1(S)-methyl-propyl)amino)(phenyl)acetate A solution of 100 mg (0.35 mmol) of 3-(4-chlorophenyl)-2(S)-(3-cyanophenyl)-1(S)-methyl-propylamine in 2 mL of dichloroethane was treated with 53 mg (0.32 mmol) of phenylpyruvic acid and 112 mg (0.53 mmol) of sodium triacetoxyborohydride. After stirring for 3 hr the reaction was quenched with water and the layers were separated. The organic layer was dried and concentrated. The residue was diluted with 1 mL of $CH_2Cl_2$, 1 mL of methanol and 0.5 mL of 2 M (trimethylsilyl)diazomethane in hexane was added. After stirring for 1 hr, the solution was concentrated. The residue was purified on a prep TLC plate using 20% EtOAc/hexane to isolate the title product as a mixture of two diastereomers. LC-MS: m/e=433 (M+1), 3.15 min.

EXAMPLE 4

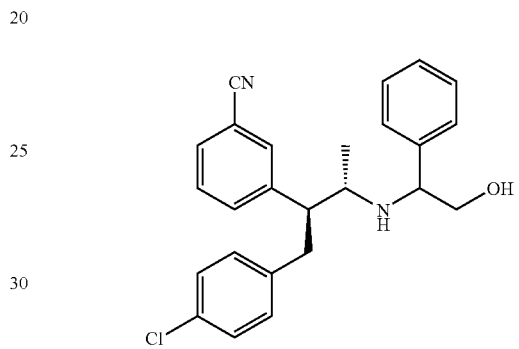

3-(1(S)-1-(4-Chlorobenzyl)-2(S)-((2-hydroxy-1-phenylethyl)amino)propyl)benzonitrile The title compound (mixture of two isomers) was prepared by the method of example 1 by substituting 2-hydroxyacetophenone for 2-hydroxy-2-methylpropiophenone. LC-MS: m/e=405 (M+1), (2.99 min).

EXAMPLE 5

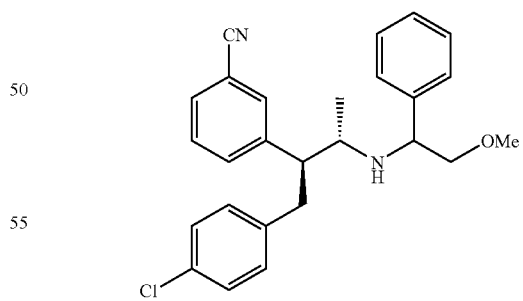

3-(1(S)-(4-Chlorobenzyl)-2(S)-((2-methoxy-1-phenylethyl)amino)propyl)benzonitrile The title compound (mixture of two isomers) was synthesized by the method of example 1 by substituting 2-methoxyacetophenone for 2-hydroxy-2-methylpropiophenone. LC-MS: m/e=419 (M+1), (3.09 min).

EXAMPLES 6 AND 7

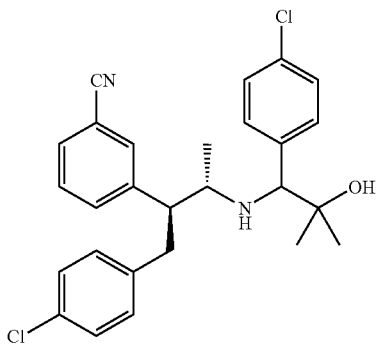

3-(1(S)-(4-Chlorobenzyl)-2(S)-((1-(4-chlorophenyl)-2-hydroxy-2-methyl-propyl)amino)propyl)benzonitrile (diastereomer A) and 3-(1(S)-(4Chlorobenzyl)-2(S)-((1-(4-chlorophenyl)-2-hydroxy-2-methyl-propyl)amino)propyl)benzonitrile (diastereomer B)

Step A: 1-(4-chlorophenyl)-2-methyl-2-trimethylsilyloxy-propan-1-one

A mixture of 3.67 g (26.1 mmol) of 4-chlorobenzaldehyde and 3.48 mL of trimethylsilyl cyanide was heated at 80° C. overnight to form (4-chlorophenyl)-(trimethylsilyloxy)acetonitrile. In a dry flask LDA was prepared by adding 5.5 mL of 2.5 M n-butyllithium to 1.92 mL of diisopropylamine in 5 mL of THF at 0° C. This LDA solution was cooled in ice bath and 3 g (12.5 mmol) of the cyanohydrin prepared above in 20 mL of THF was added. After 15 min, 0.92 mL (12.5 mmol) of acetone was added and the ice bath was removed. After stirring for 1 hr, the reaction was quenched with aqueous NH$_4$Cl and extracted with CH$_2$Cl$_2$. The organic layer was washed with water, brine, dried and concentrated to furnish 1-(4-chlorophenyl)-2-methyl-2-trimethylsilyloxy-propan-1-one which was sufficiently pure to use in the next step without purification. $^1$H NMR: (500 MHz, CDCl$_3$): δ 0.09 (s, 9H), 1.60 (s, 6H), 7.42 (d, 2H), 8.2 (d, 2H).

Step B: 1-(4-Chlorophenyl)-2-methyl-2-hydroxy-propan-1-one

To a solution of 3.4 g of 1-(4-chlorophenyl)-2-methyl-2-trimethylsilyloxy-propan-1-one in 10 mL of methanol 4 mL of 2N HCl was added and the mixture was stirred for 3 hr. The reaction was diluted with CH$_2$Cl$_2$ and washed with water, brine, dried and concentrated to give the title compound which was used in the next step without purification. $^1$H NMR: (500 MHz, CDCl$_3$): δ 1.65 (s, 6H), 7.47 (d, 2H), 8.03 (d, 2H)

Step C: 3-(1(S)-(4-Chlorobenzyl)-2(S)-((2-hydroxy-2-methyl-1-phenylpropyl)amino)propyl)benzonitrile To a solution of 100 mg (0.31 mmol) of 3-(4-chlorophenyl)-2(S)-(3-cyanophenyl)-1(S)-methyl-propylamine hydrochloride in 2 mL of CH$_2$Cl$_2$, 54 µL (0.31 mmol) of diisopropylethylamine and 62 mg (0.31 mmol) of 1-(4-chlorophenyl)-2-methyl-2-hydroxy-propan-1-one were added. After 5 min, 99 mg (0.47 mmol) of sodium triacetoxyborohydride was added and stirred for 3 hr. The reaction was quenched with water and the layers were separated. The organic layer was dried and concentrated. The residue was purified on a prep TLC plate using 30% EtOAc/hexane as an eluant to isolate two products. The higher Rf band gave 3-(1(S)-(4-chlorobenzyl)-2(S)-((2-hydroxy-2-methyl-1-phenylpropyl)amino)propyl)benzonitrile (diastereomer A) and the lower Rf band gave 3-(1(S)-4-chlorobenzyl)-2(S)-((2-hydroxy-2-methyl-1-phenylpropyl)amino)propyl)benzonitrile (diastereomer B). Diastereomer A, LC-MS: m/e=467 (M+1), 469 (M+3) (3.28 min). Diastereomer B, LC-MS: m/e=467 (M+1), 469 (M+3) (3.28 min).

The compounds in the table below were synthesized by the method described in Example 6 by substituting appropriate aldehyde for 4-chlorobenzaldehyde and the requisite ketone for acetone.

| Ex. No. | Name | retention time (min) | HPLC-mass spectrum m/e | Structure |
|---|---|---|---|---|
| 8 | 3-(1-(S)-(4-Chlorobenzyl)-2(S)-((1-(3,5-difluorophenyl)-2-hydroxy-2-methyl-propyl)amino)propyl)-benzonitrile (Diastereomer A) | 3.2 | 469 | 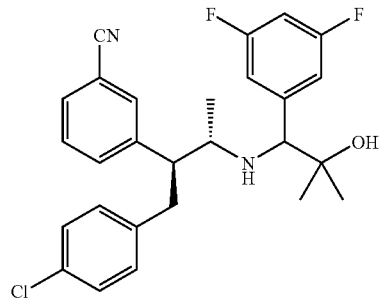 |

-continued

| Ex. No. | Name | retention time (min) | HPLC-mass spectrum m/e | Structure |
|---|---|---|---|---|
| 9 | 3-(1-(S)-(4-Chlorobenzyl)-2(S)-((1-(3,5-difluorophenyl)-2-hydroxy-2-methyl-propyl)amino)propyl)-benzonitrole (Diastereomer B) | 3.2 | 469 | 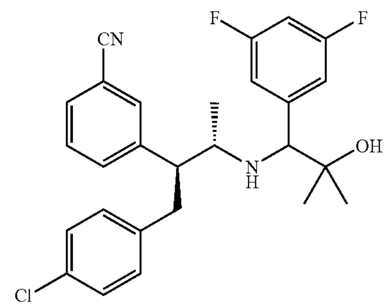 |
| 10 | 3-(1(S)-(4-Chlorobenzyl)-2(S)-((1-(2-chlorophenyl)-2-hydroxy-2-methyl-propyl)amino)propyl)-benzonitrile | 3.17 | 467 | 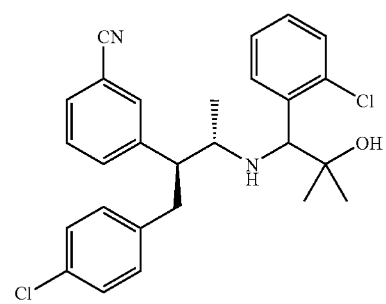 |
| 11 | 3-(1(S)-(4-Chlorobenzyl)-2(S)-((1-(3-chlorophenyl)-2-hydroxy-2-methyl-propyl)amino)propyl)-benzonitrile | 3.20 | 467 | 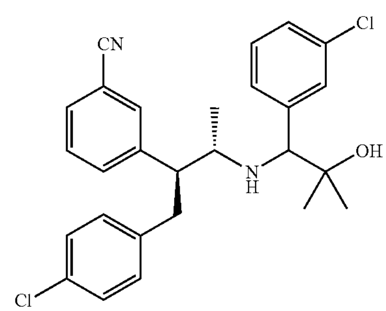 |
| 12 | 3-(1(S)-(4-Chlorobenzyl)-2(S)-((1-(2,4-difluorophenyl)-2-hydroxy-2-methyl-propyl)amino)propyl)-benzonitrile | 3.15 | 469 | 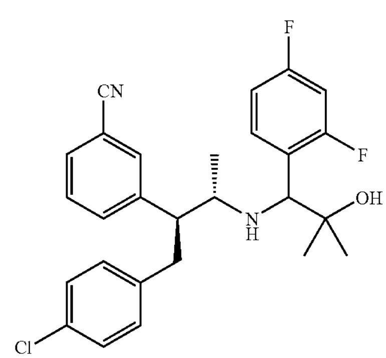 |

-continued

| Ex. No. | Name | retention time (min) | HPLC-mass spectrum m/e | Structure |
|---|---|---|---|---|
| 13 | 3-(1(S)-(4-Chlorobenzyl)-2(S)-((1-(3,4-difluorophenyl)-2-hydroxy-2-methyl-propyl)amino)propyl)-benzonitrile (Diastereomer A) | 3.15 | 469 | 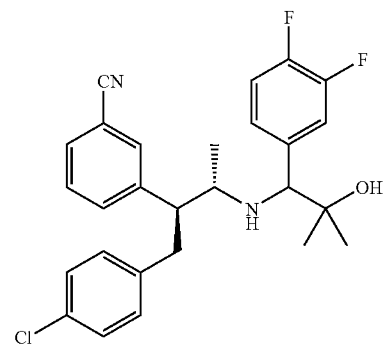 |
| 14 | 3-(1(S)-(4-Chlorobenzyl)-2(S)-((1-(3,4-difluorophenyl)-2-hydroxy-2-methyl-propyl)amino)propyl)-benzonitrile (Diastereomer B) | 3.15 | 469 | 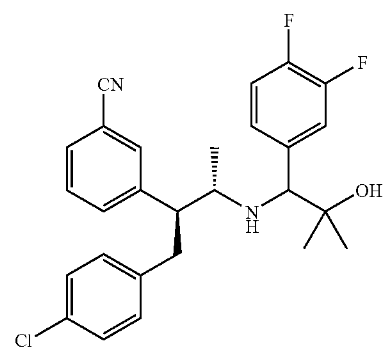 |
| 15 | 3-(1(S)-(4-Chlorobenzyl)-2(S)-((1-(2-chloro-4-fluorophenyl)-2-hydroxy-2-methyl-propyl)amino)propyl)-benzonitrile | 3.23 | 485 | 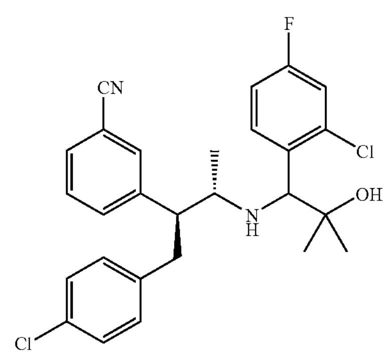 |
| 16 | 3-(1(S)-(4-Chlorobenzyl)-2(S)-((1-(2-fluoro-4-chlorophenyl)-2-hydroxy-2-methyl-propyl)amino)propyl)-benzonitrile | 3.28 | 485 | 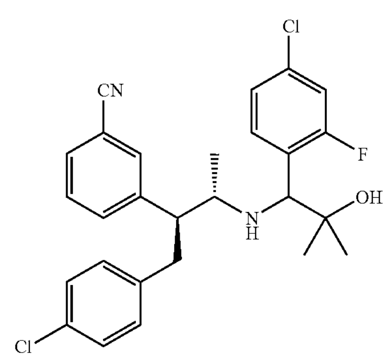 |

-continued

| Ex. No. | Name | retention time (min) | HPLC-mass spectrum m/e | Structure |
|---|---|---|---|---|
| 17 | 3-(1(S)-(4-Chlorobenzyl)-2(S)-((1-(4-fluorophenyl)-2-hydroxy-2-methyl-propyl)amino)propyl)-benzonitrile (Diastereomer A) | 3.09 | 451 | 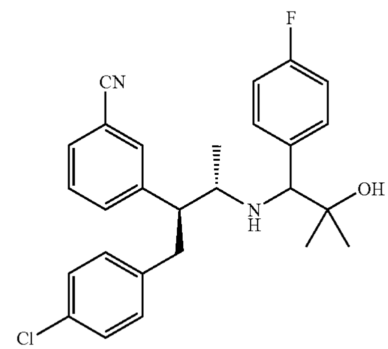 |
| 18 | 3-(1(S)-(4-Chlorobenzyl)-2(S)-((1-(4-fluorophenyl)-2-hydroxy-2-methyl-propyl)amino)propyl)-benzonitrile (Diastereomer B) | 3.09 | 451 | 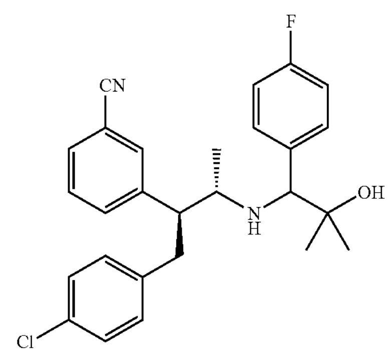 |
| 19 | 3-(1(S)-(4-Chlorobenzyl)-2(S)-(((1-hydroxycyclobutyl)-(3,5-difluorophenyl)methyl)amino)propyl)benzonitrile (Diastereomer A) | 3.12 | 481 | 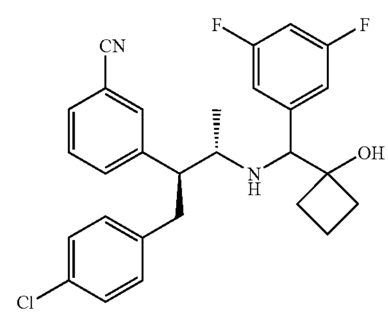 |
| 20 | 3-(1(S)-(4-Chlorobenzyl)-2(S)-(((1-hydroxycyclobutyl)-(3,5-difluorophenyl)methyl)amino)propylbenzonitrile (Diastereomer B) | 3.23 | 481 | 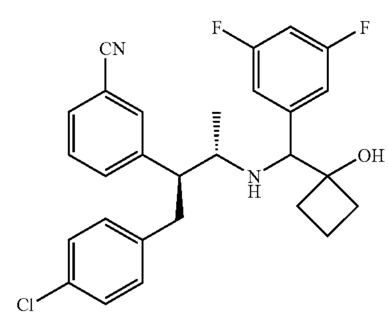 |

| Ex. No. | Name | retention time (min) | HPLC-mass spectrum m/e | Structure |
|---|---|---|---|---|
| 21 | 3-(1(S)-(4-Chlorobenzyl)-2(S)-(((1-hydroxycyclohexyl)-(3,5-difluorophenyl)methyl)amino)propyl)benzonitrile | 3.41 | 509 | 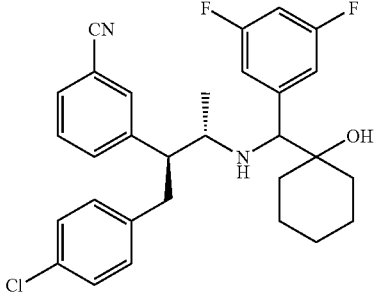 |
| 22 | 3-(1(S)-(4-Chlorobenzyl)-2(S)-((1-(3,5-difluorophenyl)-2-hydroxy-2-ethyl-butyl)amino)propyl)benzonitrile | 3.33 | 497 | 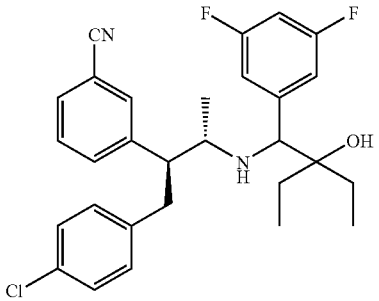 |
| 23 | 3-(1(S)-(4-Chlorobenzyl)-2(S)-((1-(3,5-difluorophenyl)-2-hydroxy-2-methoxymethyl-propyl)amino)propyl)-benzonitrile | 3.15 | 499 | 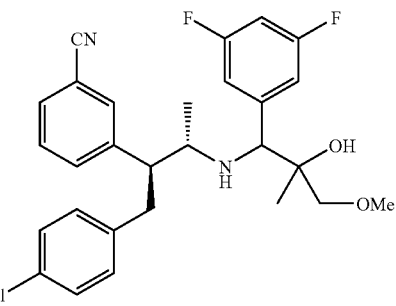 |
| 24 | 3-(1(S)-(4-Chlorobenzyl)-2(S)-((1-(3,5-difluorophenyl)-2-hydroxy-propyl)amino)propyl)-benzonitrile (Diastereomer A) | 3.11 | 455 | 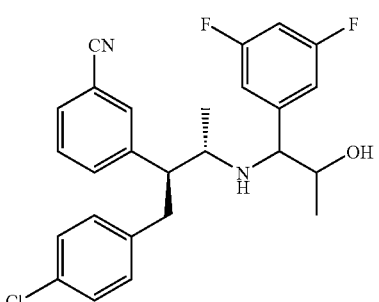 |
| 25 | 3-(1(S)-(4-Chlorobenzyl)-2(S)-((1-(3,5-difluorophenyl)-2-hydroxy-propyl)amino)propyl)-benzonitrile (Diastereomer B) | 3.22 | 455 | 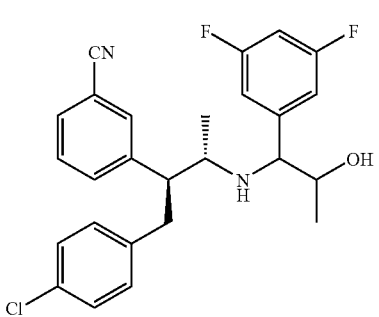 |

-continued

| Ex. No. | Name | retention time (min) | HPLC-mass spectrum m/e | Structure |
|---|---|---|---|---|
| 26 | 3-(1(S)-(4-Chlorobenzyl)-2(S)-((1-(3,5-difluorophenyl)-2-hydroxy-propyl)amino)propyl)-benzonitrile (Diastereomers C and D) | 3.12 | 455 | 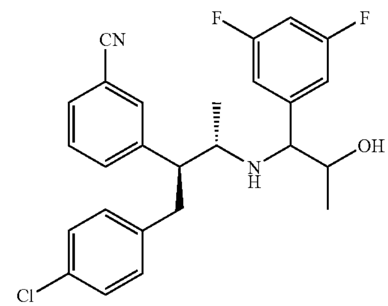 |
| 27 | 3-(1(S)-(4-Chlorobenzyl)-2(S)-((1-phenyl-3-hydroxy-2,2-dimethylpropyl)amino)propyl)-benzonitrile (Diastereomer A) | 3.12 | 447 | 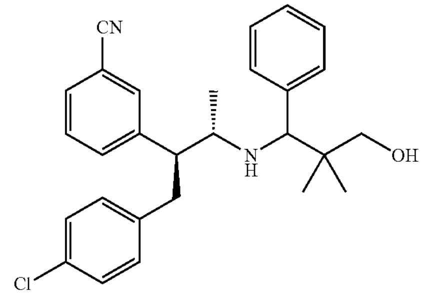 |
| 28 | 3-(1(S)-(4-Chlorobenzyl)-2(S)-((1-phenyl-3-hydroxy-2,2-dimethylpropyl)amino)propyl)-benzonitrile (Diastereomer B) | 3.15 | 447 | 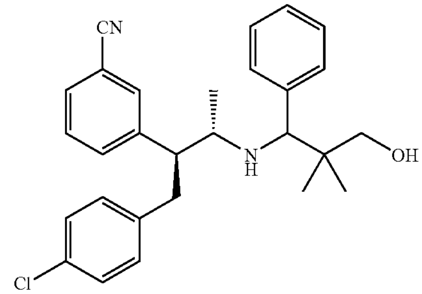 |
| 29 | 3-(1(S)-(4-Chlorobenzyl)-2(S)-((1-phenyl)-2-acetylamino-propyl)amino)propyl)-benzonitrile (mixture of isomers) | 3.10 | 460 | 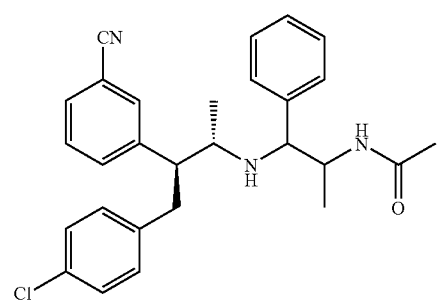 |
| 30 | 3-(1(S)-(4-Chlorobenzyl)-2(S)-((1-phenyl-2-t-butyloxycarbonylaminoethyl)-amino)propyl)-benzonitrile (mixture of isomers) | 3.27 | 504 | 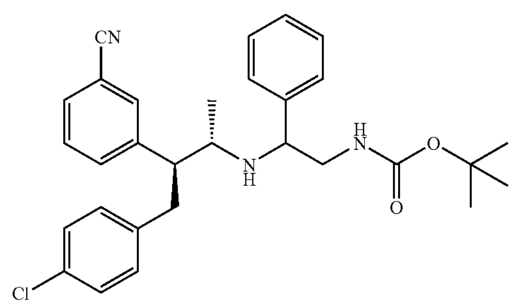 |

| Ex. No. | Name | retention time (min) | HPLC-mass spectrum m/e | Structure |
|---|---|---|---|---|
| 31 | 3-(1(S)-(4-Chlorobenzyl)-2(S)-((1-phenyl-2-aminoethyl)-amino)propyl)-benzonitrile (Diastereomer A) | 2.63 | 404 | 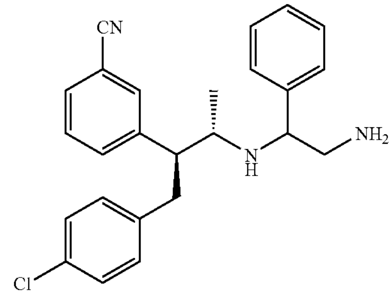 |
| 32 | 3-(1(S)-(4-Chlorobenzyl)-2(S)-((1-phenyl-2-aminoethyl)-amino)propyl)-benzonitrile (Diastereomer B) | 2.61 | 404 | 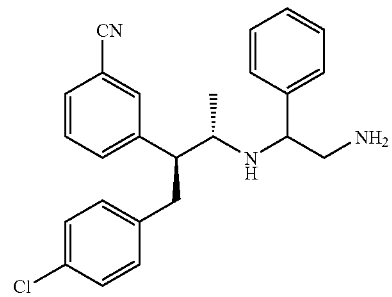 |

EXAMPLE 33 AND 34

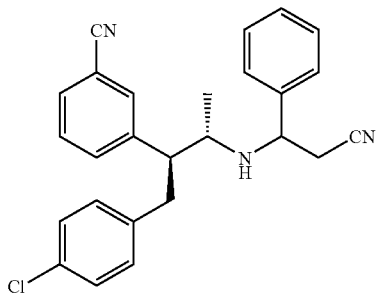

3-(1(S)-(4-Chlorobenzyl)-2(S)-((1-phenyl-2-cyanoethyl)amino)propyl)benzonitrile. (Diastereomer A) and 3-(1(S)-(4-Chlorobenzyl)-2(S)-((1-phenyl-2-cyanoethyl)amino)propyl)benzonitrile. (Diastereomer B)

A sample of 200 mg (0.62 mmol) of 3-(4-chlorophenyl)-2 (S)(3-cyanophenyl)-1(S)-methyl-propylamine hydrochloride was partitioned between 1N NaOH and ether. The layers were separated and the aqueous layer was extracted with ether. The combined ether solution was dried and concentrated. The residue was diluted with 3 mL of toluene and 145 mg (1 mmol) of benzylacetonitrile was added followed by 3 mg of toluenesulfonic acid. Few beads of 4A molecular sieves were added to the mixture and it was heated to reflux for 18 hr. The solution was cooled, filtered and the filtrate was concentrated to ca. 1 mL. This residue was diluted with 1 mL of acetic acid, cooled in an ice bath and 100 mg (2.6 mmol) of NaBH$_4$ was added in portions. After 30 min the cold bath was removed and the solution was stirred for an additional 30 min. The reaction was quenched with 10% Na$_2$CO$_3$ solution and extracted with EtOAc. The EtOAc layer was washed with brine, dried and concentrated. The residue was chromatographed on a flash column using a gradient of 10-30% EtOAc/hexane to isolate the less polar isomer (diastereomer A), LC-MS: m/e=414 (M+1), 416 (M+3) (3.18 min) and the more polar isomer (diastereomer B), LC-MS: m/e=414 (M+1), 416 (M+3) (3.11 min).

EXAMPLE 35

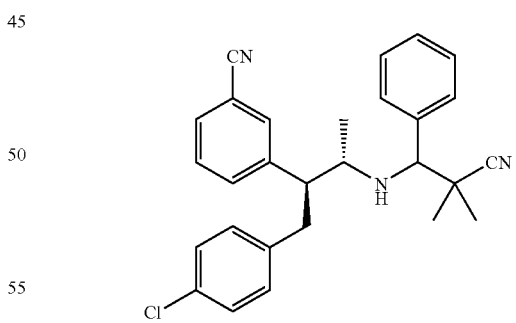

3-(1(S)-(4-Chlorobenzyl)-2(S)-((1-phenyl-2-cyano-2-methylpropyl)amino)propyl)benzonitrile (Diastereomer A)

A solution of 98 mg (0.237 mmol) of 3-((1(S)-(4-chlorobenzyl)-2(S)-((1-phenyl-2-cyanoethyl)amino)propyl)benzonitrile (diastereomer A) in 1 ml of dry THF was cooled in a −78° C. bath and 0.7 mL of 1M lithium bis(trimethylsilyl) amide was added. After 15 min, 50 μL (0.79 mmol) of methyl iodide was added and stirred for 30 min. The cold bath was removed and the reaction was continued for 30 min more. The solution was quenched with aqueous NH₄Cl and extracted with EtOAc. The EtOAc layer was washed with brine, dried and concentrated. The residue was purified on a reverse phase HPLC on a C-18 column, using a gradient of 10-90% MeCN-water containing 0.1% TFA to isolate the title compound. LC-MS: m/e=442 (M+1), 444 (M+3) (3.98 min).

EXAMPLE 36

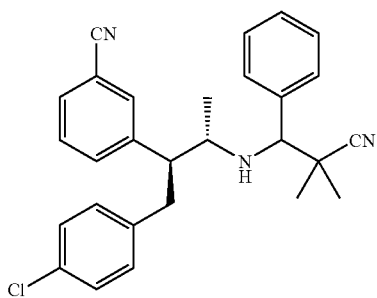

3-(1(S)-(4-Chlorobenzyl)-2(S)-((1-phenyl-2-cyano-2-methylpropyl)amino)propyl)benzonitrile (Diastereomer B)

The title compound was prepared from by 3-(1(S)-(4-chlorobenzyl)-2(S)-((1-phenyl-2-cyanoethyl)amino)propyl)benzonitrile (diastereomer B) by the method of example 35. LC-MS: m/e=442 (M+1), 444 (M+3) (4.05 min).

EXAMPLE 37

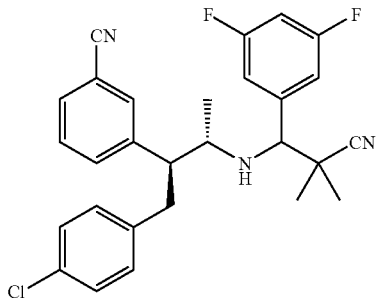

3-(1(S)-(4-Chlorobenzyl)-2(S)-((1-(3,5-difluorophenyl)-2-cyano-2-methylpropyl)amino)propyl)benzonitrile (Diastereomer A)

Step A: 3,5-Difluorobenzoyl-acetonitrile

To a solution of 0.9 g (5.8 mmol) of 3,5-difluoroacetophenone in 5 mL of CH₂Cl₂ and 1 mL of acetic acid, 0.3 mL (5.9 mmol) of bromine was added over 3-4 min. After stirring for 1 hr when all the bromine was consumed and the reaction was clear, the reaction was diluted with CH₂Cl₂. The solution was washed with water, saturated NaHCO₃, brine, dried and concentrated leaving 1.4 g of a clear liquid. A 0.7 g portion of this bromoketone was dissolved in 4 mL of ethanol and 0.4 g (6.17 mmol) of potassium cyanide was added. After stirring for 1 hr, the reaction was concentrated and the residue was acidified to pH 2 by adding 1.2 N HCl (caution!) This solution was extracted with ether and each ether layer was washed with brine, combined, dried and concentrated. The residue was purified on a flash column using a gradient of 10-20% EtOAc-hexane to isolate the desired product. ¹H NMR: (500 MHz, CDCl₃): δ 4.11 (s, 2H), 7.17 (m, 1H), 7.49 (m, 2H).

Step B: 3-(1(S)-(4-Chlorobenzyl)-2(S)-((1-(3,5-difluorophenyl)-2-cyanoethyl)amino)propyl)benzonitrile (Diastereomer A)

This compound was synthesized according to the procedure of Example 33 from 205 mg (1.13 mmol) of 3,5-difluorobenzoyl-acetonitrile and 300 mg (0.93 mmol) of 3-(4-chlorophenyl)-2(S)(3-cyanophenyl)-1(S)-methyl-propylamine hydrochloride. LC-MS: m/e=450 (M+1), 452 (M+3) (3.55 min).

Step C: 3-(1(S)-(4-Chlorobenzyl)-2(S)-((1-(3,5-difluorophenyl)-2-cyano-2-methylpropyl)amino)propyl)benzonitrile (Diastereomer A)

The title compound was prepared by the method of Example 35. LC-MS: m/e=478 (M+1), 480 (M+3) (4.24 min).

EXAMPLE 38

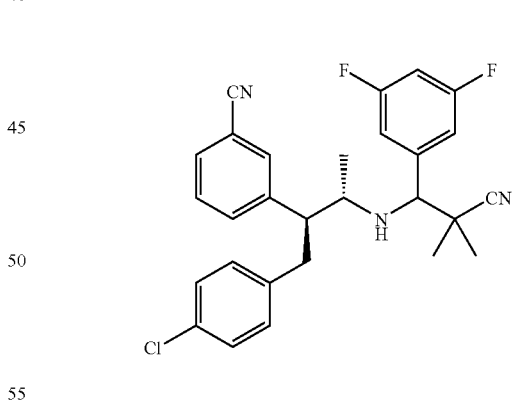

3-(1(S)-(4-Chlorobenzyl)-2(S)-((1-(3,5-difluorophenyl)-2-cyano-2-methylpropyl)amino)propyl)benzonitrile (Diastereomer B)

The title compound was obtained from 3-(1(S)-(4-chlorobenzyl)-2(S)-(1-(3,5-difluorophenyl)-2-cyanoethyl)amino)propyl)benzonitrile (diastereomer B) by the method of Example 35. LC-MS: m/e=478 (M+1), 480 (M+3) (4.25 min).

EXAMPLE 39

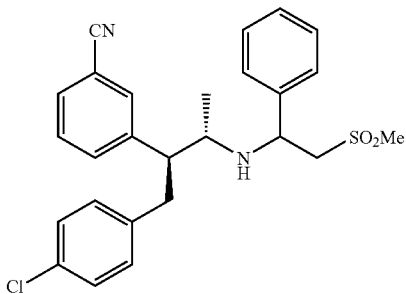

3-(1(S)-(4-Chlorobenzyl)-2(S)-((1-phenyl-2-methanesulfonylethyl)amino)propyl)benzonitrile The title compound was prepared from 3-(4-chlorophenyl)-2(S)(3-cyanophenyl)-1(S)-methyl-propylamine hydrochloride and 2-methanesulfonylacetophenone by the procedure of Example 33 as a mixture of two diastereomers. LC-MS: m/e=467 (M+1), 469 (M+3) (3.05 min and 4.05 min).

EXAMPLES 40 AND 41

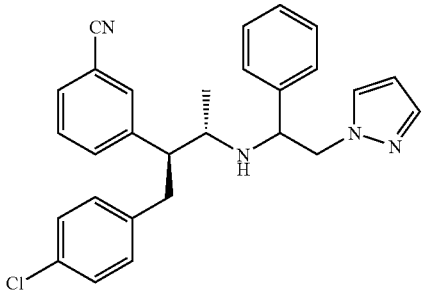

3-(1(S)-(4-Chlorobenzyl)-2(S)-((1-phenyl-2-(1H-pyrazol-1-yl)ethyl)amino)propyl)benzonitrile (Diastereomer A) and 3-(1(S)-(4-chlorobenzyl)-2(S)-((1-phenyl-2-(1H-pyrazol-1-yl)ethyl)amino)propyl) benzonitrile (Diastereomer B)

Step A: 1-Phenyl-2(1H-pyrazol-1-yl)ethanone

To a solution of 1.5 g (9.7 mmol) of 2-chloroacetophenone in 10 mL of MeCN, 0.7 g (10.3 mmol) of pyrazole was added. After all the solids dissolved, 1.4 g (10.1 mmol) of ground $K_2CO_3$ was added and the mixture was stirred for 5 h. The reaction was diluted with EtOAc, filtered, and the solid was washed with EtOAc. The filtrate was washed with water and brine, then was dried and concentrated. The residue was chromatographed on a flash column using a gradient of 10-50% EtOAc-hexane to isolate desired product.

Step B: 3-(1(S)-(4-Chlorobenzyl)-2(S)-((1-phenyl-2-(1H-pyrazol-1-yl)ethyl)amino)propyl)benzonitrile (Diastereomer A) and 3-(1(S)-(4-chlorobenzyl)-2(S)-((1-phenyl-2-(1H-pyrazol-1-yl)ethyl)amino)propyl) benzonitrile (Diastereomer B)

To a solution of 80 mg (0.28 mmol) of 3-(4-chlorophenyl)-2(S)(3-cyanophenyl)-1(S)-methyl-propylamine in 1.5 mL of toluene, 60 mg of 1-phenyl-2(1H-pyrazol-1-yl)ethanone and 5 mg of TsOH were added. Powdered 4A molecular sieves (~300 mg) were added to the reaction and it was heated to reflux for 5 hr. The mixture was allowed to cool overnight, filtered and the solid washed with EtOAc. The filtrate was concentrated and the residue was dissolved in 1.5 mL of THF, 0.1 mL of acetic acid. This solution was treated with 20 mg of $NaCNBH_3$ for 1.5 hr. The reaction was diluted with EtOAc, washed with saturated $NaHCO_3$, brine, dried and concentrated. The residue was purified on a prep TLC plate using 50% EtOAC-hexane as eluant to isolate of the higher $R_f$ isomer, 3-(1(S)-(4-chlorobenzyl)-2(S)-((1-phenyl-2-(1H-pyrazol-1-yl)ethyl)amino)propyl)benzonitrile (Diastereomer A) LC-MS: m/e=455 (M+1), 457 (M+3) (3.16 min). and the lower $R_f$ isomer, 3-(1(S)-(4-chlorobenzyl)-2(S)-(1-phenyl-2-(1H-pyrazol-1-yl)ethyl)amino)propyl)benzonitrile (Diastereomer B) LC-MS: m/e=455 (M+1), 457 (M+3) (3.12 min).

EXAMPLE 42

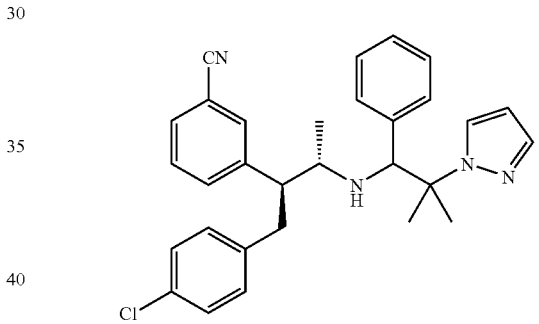

3-(1(S)-(4-Chlorobenzyl)-2(S)-((2-methyl-1-phenyl-2-(1H-pyrazol-1-yl)propyl)amino)propyl)benzonitrile To a solution of 80 mg (0.28 mmol) of 3-(4-chlorophenyl)-2(S)(3-cyanophenyl)-1(S)-methyl-propylamine in 1.5 mL of toluene, 60 mg of 1-phenyl-2(1H-pyrazol-1-yl)ethanone and 5 mg of TsOH were added. Powdered 4A molecular sieves (~300 mg) were added to the reaction, which was heated to reflux for 5 hr. The mixture was cooled, filtered, and the solid was washed with EtOAc. The filtrate was concentrated and the residue was diluted with 1.5 mL of THF. The solution was cooled in −78° C. bath and 1.4 mL of 1 M $LiN(TMS)_2$ was added. After 5 min 0.1 mL of MeI was added and the reaction was stirred overnight while it warmed to room temperature. The solution was quenched with saturated $NH_4Cl$ and extracted with EtOAc. The organic layer was washed with brine, dried and concentrated. The residue was predominantly monomethyl imine. It was dissolved in 1.5 mL of THF cooled in −78° C. bath and treated with 1.5 mL of $LiN(TMS)_2$ and 0.12 mL of MeI. After 10 min, the cold bath was removed, and the mixture was stirred for 5 hr. The reaction was quenched with saturated $NH_4Cl$ and extracted with EtOAc.

The organic layer was washed with brine, dried, and concentrated. The residue was dissolved in 1.5 mL of THF, 0.1 mL of HOAc, and 32 mg (0.5 mmol) of NaCNBH₃ was added. After stirring overnight, the solution was quenched with saturated NaHCO₃ and extracted with ETOAc. The organic layer was washed with brine, dried and concentrated. The residue was purified on a prep TLC plate using 50% EtOAc-hexane to isolate the title compound as a mixture of diastereomers. LC-MS: m/e=483 (M+1), 485 (M+3) (3.36 min). Additional two bands containing diastereomers of 3-(1(S)-(4-chlorobenzyl)-2(S)-((1-phenyl-2-(1H-pyrazol-1-yl)propyl)amino)propyl)benzonitrile were also isolated. LC-MS: m/e=469 (M+1), 471 (M+3) (3.24 min) and LC-MS: m/e=469 (M+1), 471 (M+3) (3.94 min).

EXAMPLE 43 AND 44

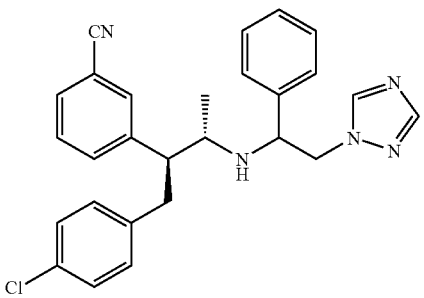

3-(1(S)-(4-Chlorobenzyl)-2(S)-((1-phenyl-2-(1H-1,2,4-triazol-1-yl)ethyl)amino)propyl)benzonitrile (Diastereomer A) and 3-(1(S)-(4-chlorobenzyl)-2(S)-(1-phenyl-2-(1H-1,2,4-triazol-1-yl)ethyl)amino)propyl)benzonitrile (Diastereomer B)

The title compounds were prepared by the procedure of example 40-41 by substituting 1,2,4-triazole for pyrazole. LC-MS: m/e=456 (M+1), 458 (M+3) (3.26 min) and LC-MS: m/e=456 (M+1), 458 (M+3) (3.39 min).

EXAMPLE 45 AND 46

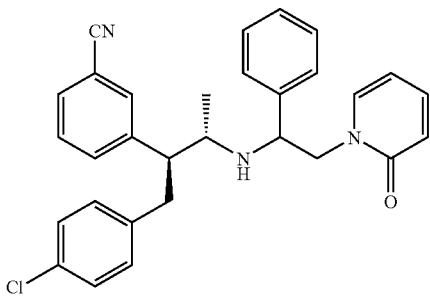

3-(1(S)-(4-Chlorobenzyl)-2(S)-((2-(2-oxopyridin-1(2H)-yl-1-phenyl-ethyl)amino)propyl)benzonitrile (Diastereomer A) and. 3-(1(S)-(4-chlorobenzyl)-2(S)-((2-(2-oxopyridin-1(2H)-yl-1-phenyl-ethyl)amino)propyl)benzonitrile (Diastereomer B)

The title compounds were prepared by the procedure of Examples 40-41 by substituting 2-hydroxypyridine for pyrazole. LC-MS: m/e=482 (M+1), 484 (M+3) (3.01 min) and LC-MS: m/e=482 (M+1), 484 (M+3) (2.98 min).

EXAMPLE 47

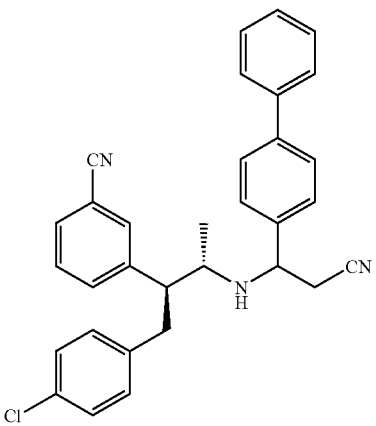

3-(1(S)-4-Chlorobenzyl)-2(S)-((1-biphenyl-4-yl-2-cyanoethylamino)propyl)benzonitrile (Diastereomer A)

Step A: 3-Biphenyl-4-yl-3-oxo-propanenitrile

To a solution of 105 mg (1.6 mmol) of KCN in 1 mL of water, 220 mg (0.8 mmol) of 2-bromo-4'-phenylacetophenone in 3 mL of MeCN was added. The mixture was warmed in a 50° C. bath to dissolve some of the halide. After ~20 min the solids dissolved. The reaction was stirred for 30 min, then partitioned between 1.2 N HCl and EtOAc. The organic layer was washed with brine, dried and concentrated leaving 210 mg of the title compound which was used in the next step without purification.

Step B: 3-(1(S)-(4-Chlorobenzyl)-2(S)-((1-biphenyl-4-yl-2-cyanoethylamino)propyl)benzonitrile (Diastereomer A)

Free base was extracted into ether by neutralizing 200 mg of 3-(4-chlorophenyl)-2(S)-(3-cyanophenyl)-1(S)-methyl-propylamine hydrochloride with aq. NaOH in presence of ether. The layers were separated and the ether layer was washed with brine, dried and concentrated. The residue was dissolved in 3 mL of toluene, 210 mg of 3-biphenyl-4-yl-3-oxo-propanenitrile and a few crystals of TsOH were added. The mixture was heated in a 145° C. bath, and toluene was distilled off. After most of the toluene was removed fresh toluene was added and distillation was continued. After removing 6×3 mL of toluene, the reaction was cooled and diluted with 2 mL toluene and 1 mL of HOAc. The solution was cooled in an ice bath and 100 mg of NaBH₄ was added in portions. After 30 min, the ice bath was removed, and stirring was continued for another 45 min. The reaction was quenched with saturated NaHCO₃, and extracted with EtOAc. The organic layer was washed with brine, dried and concentrated. The residue was purified on a flash column using a gradient of 10-40% EtOAc-hexane to obtain the title compound as the less polar isomer. LC-MS: m/e=490 (M+1), 492 (M+3) (3.58 min). The more polar isomer was also isolated. LC-MS: m/e=490 (M+1), 492 (M+3) (3.46 min).

EXAMPLE 48

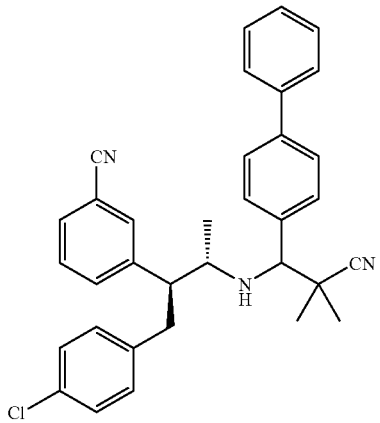

3-(1(S)-(4-Chlorobenzyl)-2(S)-(1-biphenylyl-2-cyano-2-methylpropyl)amino)propyl)benzonitrile (Diastereomer A)

A solution of 92 mg (0.19 mmol) of 3-(1(S)-(4-chlorobenzyl)-2(S)-(1-biphenyl-4-yl-2-cyanoethylamino)propyl)benzonitrile (Diastereomer A) in 1 mL of THF was cooled in −78° C. bath and 1 mL of 1 M LiN(TMS)$_2$ was added. After 5 min, 0.1 mL (1.59 mmol) of MeI was added. The cold bath was removed after 30 min, and stirring was continued for another 30 min. The reaction was quenched with saturated NH$_4$Cl and extracted with EtOAc. The EtOAc layer was washed with brine, dried and concentrated. The residue was purified on a prep TLC plate using 30% EtOAc-hexane to isolate the title compound. LC-MS: m/e=518 (M+1), 520 (M+3) (4.44 min).

The following compounds were prepared by the method of example 47, using the commercially available cyano-ketone, or by making the cyanoketone as described in example 37, step A.

TABLE 1

EXAMPLES 49–72

| Ex. No. | Name | Structure | HPLC-retention time (min) | mass spectrum m/e |
|---|---|---|---|---|
| 49 | 3-(1(S)-(4-Chlorobenzyl)-2(S)-((1-(3-bromophenyl)-2-cyanoethyl)-amino)propyl)benzonitrile (Diastereomer A) | 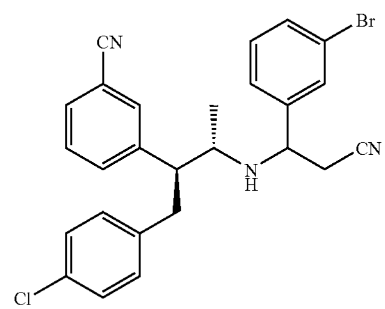 | 3.73 | 492 494 496 |
| 50 | 3-(1(S)-(4-Chlorobenzyl)-2(S)-((1-(3-bromophenyl)-2-cyanoethyl)-amino)propyl)benzonitrile (Diastereomer B) | 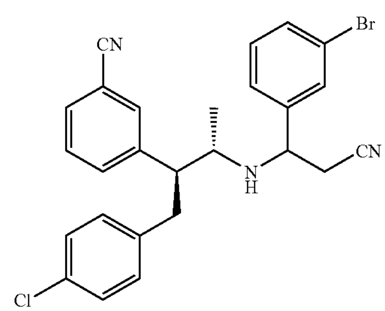 | 3.51 | 492 494 496 |

TABLE 1-continued

EXAMPLES 49–72

| Ex. No. | Name | Structure | retention time (min) | HPLC-mass spectrum m/e |
|---|---|---|---|---|
| 51 | 3-(1(S)-(4-Chlorobenzyl)-2(S)-((1-(3-chlorophenyl)-2-cyanoethyl)-amino)propyl)benzonitrile (Diastereomer A) | 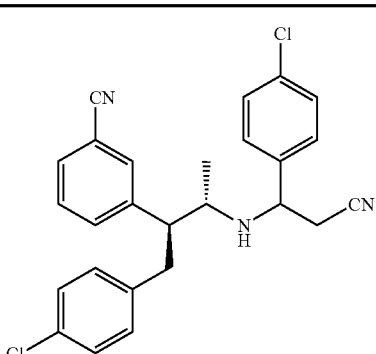 | 3.59 | 448 450 |
| 52 | 3-(1(S)-(4-Chlorobenzyl)-2(S)-((1-(3-chlorophenyl)-2-cyanoethyl)-amino)propyl)benzonitrile (Diastereomer B) | 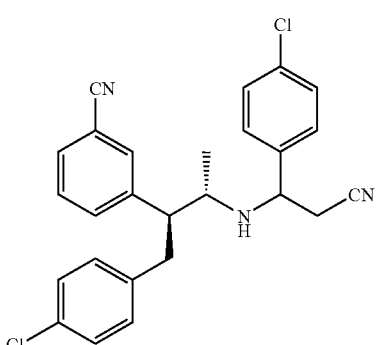 | 3.40 | 448 450 |
| 53 | 3-(1(S)-(4-Chlorobenzyl)-2(S)-((1-(4-fluorophenyl)-2-cyanoethyl)-amino)propyl)benzonitrile (Diastereomer A) | 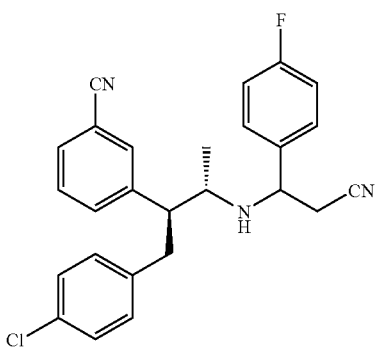 | 3.39 | 432 434 |
| 54 | 3-(1(S)-(4-Chlorobenzyl)-2(S)-((1-(4-fluorophenyl)-2-cyanoethyl)-amino)propyl)benzonitrile (Diastereomer B) | 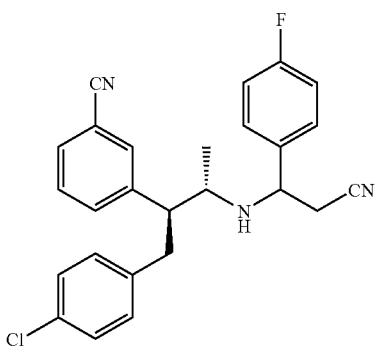 | 3.22 | 432 434 |

TABLE 1-continued

EXAMPLES 49–72

| Ex. No. | Name | Structure | retention time (min) | HPLC-mass spectrum m/e |
|---|---|---|---|---|
| 55 | 3-(1(S)-(4-Chlorobenzyl)-2(S)-((1-(3-chlorophenyl)-2-cyanoethyl)-amino)propyl)benzonitrile (Diastereomer A) | 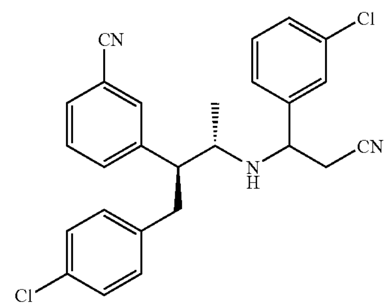 | 3.72 | 448 450 |
| 56 | 3-(1(S)-(4-Chlorobenzyl)-2(S)-((1-(3-chlorophenyl)-2-cyanoethyl)-amino)propyl)benzonitrile (Diastereomer B) | 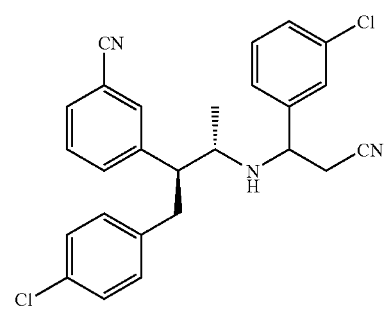 | 3.47 | 448 450 |
| 57 | 3-(1(S)-(4-Chlorobenzyl)-2(S)-((1-(3-trifluoromethylphenyl)-2-cyano-ethyl)amino)propyl)benzonitrile (Diastereomer A) | 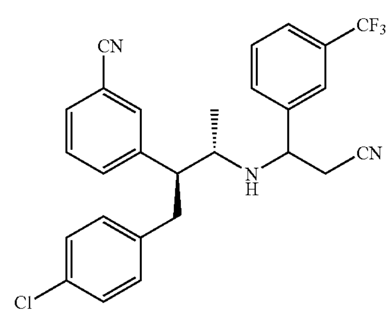 | 3.88 | 482 484 |
| 58 | 3-(1(S)-(4-Chlorobenzyl)-2(S)-((1-(3-trifluoromethylphenyl)-2-cyano-ethyl)amino)propyl)benzonitrile (Diastereomer B) | 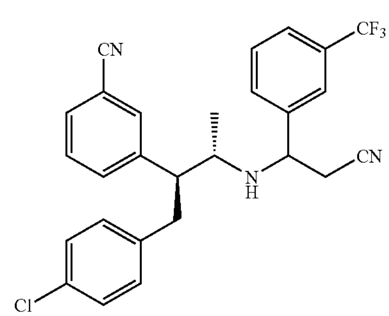 | 3.66 | 482 484 |

TABLE 1-continued

EXAMPLES 49–72

| Ex. No. | Name | Structure | retention time (min) | HPLC-mass spectrum m/e |
|---|---|---|---|---|
| 59 | 3-(1(S)-(4-Chlorobenzyl)-2(S)-((1-(4-trifluoromethylphenyl)-2-cyano-ethyl)amino)propyl)benzonitrile (Diastereomer A) | 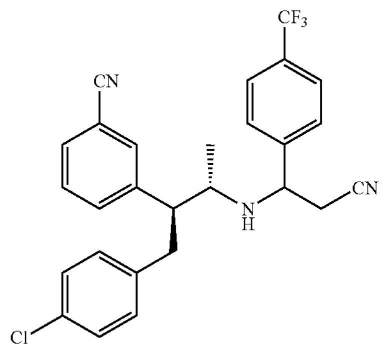 | 3.88 | 482 484 |
| 60 | 3-(1(S)-(4-Chlorobenzyl)-2(S)-((1-(4-trifluoromethylphenyl)-2-cyano-ethyl)amino)propyl)benzonitrile (Diastereomer B) | 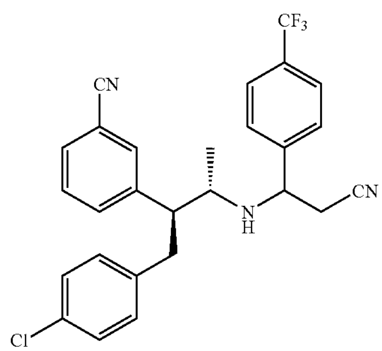 | 3.66 | 482 484 |
| 61 | 3-(1(S)-(4-Chlorobenzyl)-2(S)-((1-(4-methylphenyl)-2-cyanoethyl) amino)propyl)benzonitrile (Diastereomer A) | 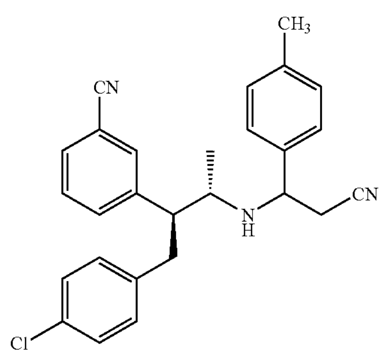 | 3.3 | 428 430 |
| 62 | 3-(1(S)-(4-Chlorobenzyl)-2(S)-((1-(4-methylphenyl)-2-cyanoethyl)-amino)propyl)benzonitrile (Diastereomer B) | 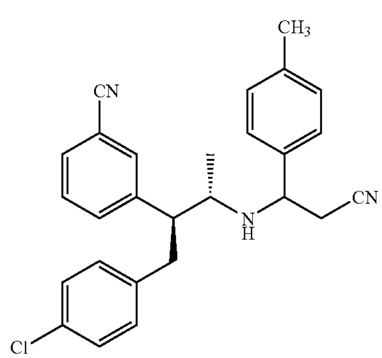 | | |

TABLE 1-continued

EXAMPLES 49–72

| Ex. No. | Name | Structure | retention time (min) | HPLC- mass spectrum m/e |
|---|---|---|---|---|
| 63 | 3-(1(S)-(4-Chlorobenzyl)-2(S)-((1-(4-methoxycarbonylphenyl)-2-cyanoethyl)amino)propyl) benzonitrile (Diastereomer A) | 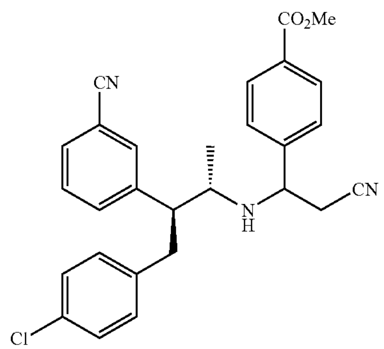 | 3.32 | 472 474 |
| 64 | 3-(1(S)-(4-Chlorobenzyl)-2(S)-((1-(4-methoxycarbonylphenyl)-2-cyanoethyl)amino)propyl) benzonitrile (Diastereomer B) | 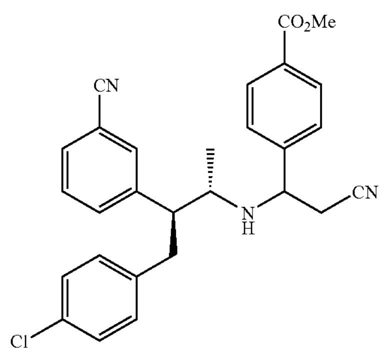 | 3.12 | 472 474 |
| 65 | 3-(1(S)-(4-Chlorobenzyl)-2(S)-((1-(3-trifluoromethoxyphenyl)-2-cyanoethyl)amino)propyl) benzonitrile (Diastereomer A) | 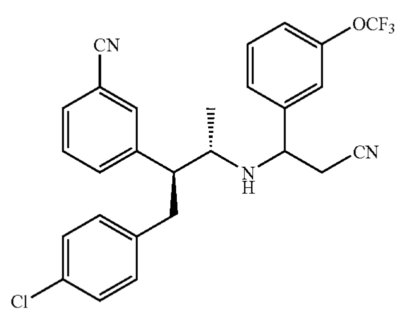 | 3.62 | 498 500 |
| 66 | 3-(1(S)-(4-Chlorobenzyl)-2(S)-((1-(3-trifluoromethoxyphenyl)-2-cyanoethyl)amino)propyl) benzonitrile (Diastereomer B) | 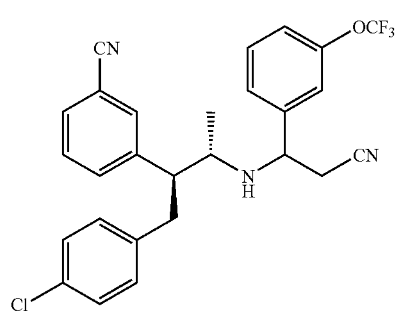 | 3.45 | 498 500 |

TABLE 1-continued

EXAMPLES 49–72

| Ex. No. | Name | Structure | retention time (min) | HPLC-mass spectrum m/e |
|---|---|---|---|---|
| 67 | 3-(1(S)-(4-Chlorobenzyl)-2(S)-((1-(3-methylphenyl)-2-cyanoethyl)amino)propyl)benzo-nitrile (Diastereomer A) | 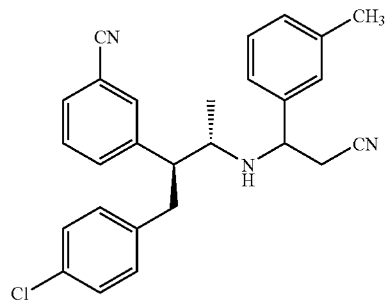 | 3.38 | 428 430 |
| 68 | 3-(1(S)-(4-Chlorobenzyl)-2(S)-((1-(3-methylphenyl)-2-cyanoethyl)amino)propyl)benzo-nitrile (Diastereomer B) | 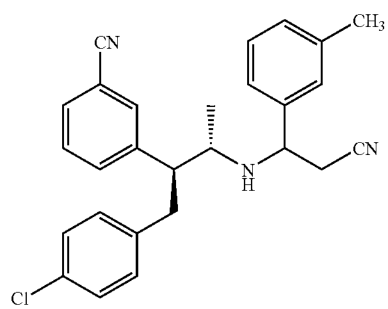 | 3.2 | 428 430 |
| 69 | 3-(1(S)-(4-Chlorobenzyl)-2(S)-((1-(2-chlorophenyl)-2-cyanoethyl)amino)propyl)benzo-nitrile (Diastereomer A) | 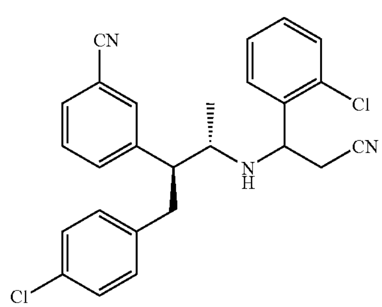 | 3.50 | 448 450 |

TABLE 1-continued

EXAMPLES 49–72

| Ex. No. | Name | Structure | retention time (min) | HPLC-mass spectrum m/e |
|---|---|---|---|---|
| 70 | 3-(1(S)-(4-Chlorobenzyl)-2(S)-((1-(2-chlorophenyl)-2-cyanoethyl)amino)propyl)benzonitrile (Diasteromer A) | 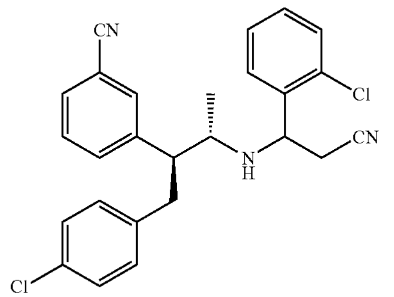 | 3.74 | 448 450 |
| 71 | 3-(1(S)-(4-Chlorobenzyl)-2(S)-((1-(3,4-dichlorophenyl)-2-cyanoethyl)amino)propyl)benzonitrile (Diasteromer A) | 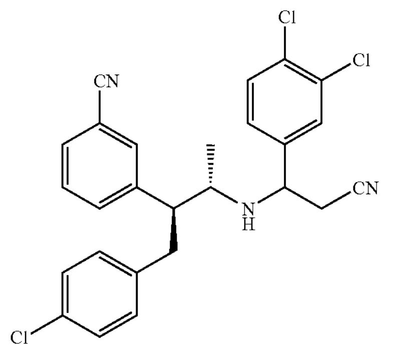 | 4.09 | 482 484 |
| 72 | 3-(1(S)-(4-Chlorobenzyl)-2(S)-((1-(3,4-dichlorophenyl)-2-cyanoethyl)amino)propyl)benzonitrile (Diastereomer B) | 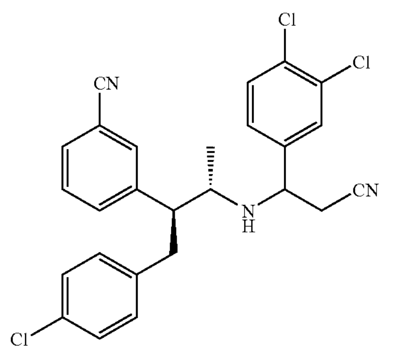 | 3.92 | 482 484 |

EXAMPLES 73 AND 74

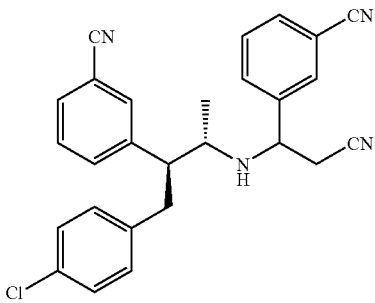

3-(1(S)-(4-Chlorobenzyl)-2(S)-((1-(3-cyanophenyl)-2-cyanoethyl)amino)propyl)benzonitrile (Diastereomer A) and 3-(1(S)-4-Chlorobenzyl)-2(S)-((1-(3-cyanophenyl)-2-cyanoethyl)amino)propyl)benzonitrile (Diastereomer B)

A solution of 164 mg (0.33 mmol) of 3-(1(S)-(4-chlorobenzyl)-2(S)-((1-(3-bromophenyl)-2-cyanoethyl)amino)propyl)benzonitrile (mixture of two diastereomers) in 2 mL of DMF and 0.02 mL of water was treated with 35 mg of Zinc cyanide, 7 mg (0.008 mmol) of tris(dibenzylidineacetone)dipalladium and 11 mg (0.02 mmol) of 1,1'-bis(diphenylphosphino)ferrocene. The solution was degassed by bubbling $N_2$ for 30 min, while the color changed from brown to yellow-orange. The vial was sealed and heated in a microwave reactor at 180° C. for 1 hr. After the reaction cooled, it was filtered through a pad of CELITE, diatomaceous earth, and the solids were washed with ether. The filtrate was diluted with ether, washed with water, and brine, then dried and concentrated. The residue was purified by prep TLC to obtain the less polar isomer, 3-(1(S)-(4-chlorobenzyl)-2(S)-((1-(3-cyanophenyl)-2-cyanoethyl)amino)propyl)benzonitrile (Diastereomer A); LC-MS: m/e=439 (M+1), 441 (M+3) (3.62 min) and more polar isomer 3-(1(S)-(4-Chlorobenzyl)-2(S)-((1-(3-cyanophenyl)-2-cyanoethyl)amino)propyl)benzonitrile (Diastereomer B); LC-MS: m/e=439 (M+1), 441 (M+3) (3.41 min).

hexane as eluant to isolate the higher $R_f$ isomer 3-(1(S)-(4-chlorobenzyl)-2(S)-((1-(3-cyanophenyl)-2-cyano-2-methyl-propyl)amino)propyl)benzonitrile (Diastereomer A), LC-MS: m/e=467 (M+1), 469 (+3) (4.14 min) and the lower Rf isomer 3-(1(S)-(4-chlorobenzyl)-2(S)-((1-(3-cyanophenyl)-2-cyano-2-methyl-propyl)amino)propyl)benzonitrile (Diastereomer B) LC-MS: m/e=467 (M+1), 469 (M+3) (4.15 min).

EXAMPLES 77 AND 78

EXAMPLE 75 AND 76

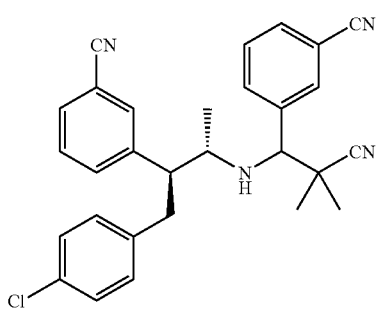

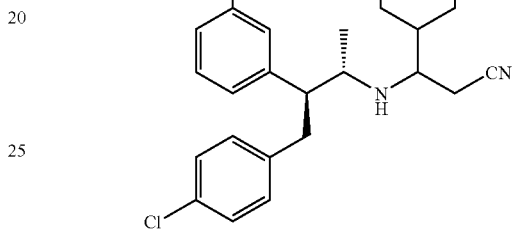

3-(1(S)-(4-Chlorobenzyl)-2(S)-((1-(3-cyanophenyl)-2-cyano-2-methyl-propyl)amino)propyl)benzonitrile (Diastereomer A) and 3-(1(S)-(4-Chlorobenzyl)-2(S)-((1-(3-cyanophenyl)-2-cyano-2-methyl-propyl)amino)propyl)benzonitrile (Diastereomer B)

Step A: 3-(1(S)-(4-Chlorobenzyl)-2(S)-((1-(3-cyanophenyl)-2-cyanoethyl)amino)propyl)benzonitrile The desired compound was obtained as described in EXAMPLES 71 and 72, except that the two diastereomers were not separated.

Step B: 3-(1(S)-4Chlorobenzyl)-2(S)-((1-(3-cyanophenyl)-2-cyano-2-methyl-propyl)amino)propyl)benzonitrile (Diastereomer A) and 3-(1(S)-(4-Chlorobenzyl)-2(S)-(1-(3-cyano-phenyl)-2-cyano-2-methyl-propyl)amino)propyl)benzonitrile (Diastereomer B)

A solution of 100 mg (0.23 mmol) of 3-(1(S)-(4-chlorobenzyl)-2(S)-(1-(3-cyanophenyl)-2-cyanoethyl)amino)propyl)benzonitrile (mixture of two isomers) in 1 mL of THF was cooled in −78° C. bath and 1 mL of LiN(TMS)$_2$ was added. After 5 min 0.1 mL (1.59 mmol) of MeI was added. After 30 min, the cold bath was removed, and stirring was continued for another 30 min. The reaction was quenched with saturated NH$_4$Cl and extracted with EtOAc. The organic layer was washed with brine, dried and concentrated. The residue was purified on a prep TLC plate using 30% EtOAc- 3-(1(S)-(4-Chlorobenzyl)-2(S)-((1-cyclohexyl-2-cyanoethyl)amino)propyl)benzonitrile (Diastereomer A) and 3-(1(S)-(4-Chlorobenzyl)-2(S)-((1-cyclohexyl-2-cyanoethyl)amino)propyl)benzonitrile (Diastereomer B)

Step A: 3-Cyclohexyl-3-oxo-propanenitrile

A solution of 0.53 mL (10 mmol) of MeCN in 5 ml of THF was cooled in −78° C. bath and 12 mL of 1M LiN(TMS)$_2$ was added. After 5 min, 0.75 mL (5.2 mmol) of methyl cyclohexane carboxylate was added. The cold bath was removed after 1 hr and stirring was continued for another 1 hr. The reaction was acidified with 1.2 N HCl and extracted with ether. The ether layer was washed with brine, dried and concentrated. The residue was chromatographed using a gradient of 10-50% EtOAc-hexane to furnish the desired product.

Step B: 3-(1(S)-(4-Chlorobenzyl)-2(S)-((1-cyclohexyl-2-cyanoethyl)amino)propyl)benzonitrile (Diastereomer A) and 3-(1(S)-(4-Chlorobenzyl)-2(S)-((1-cyclohexyl-2-cyanoethyl)amino)propyl)benzonitrile (Diastereomer B)

The title compounds were prepared by the method described in EXAMPLE 47, step B. Diastereomer A, LC-MS: m/e=420 (M+1), 422 (M+3) (3.20 min) and Diastereomer B, LC-MS: m/e=420 (M+1), 422 (M+3) (3.21 min).

The compounds listed in TABLE 2 were synthesized by the procedure of EXAMPLES 77-78 by substituting appropriate ester for methyl cyclohexanecarboxylate in Step A.

TABLE 2

EXAMPLES 81–88

| Ex. No. | Name | Structure | retention time (min) | HPLC-mass spectrum m/e |
|---|---|---|---|---|
| 81 | 3-(1(S)-(4-Chlorobenzyl)-2(S)-((1-(4-methylthiophenyl)-2-cyano-ethyl)amino)propyl)benzonitrile (Diastereomer A) | 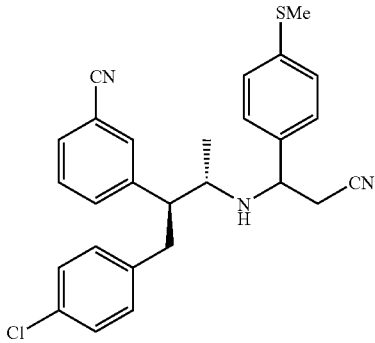 | 3.22 | 460 462 |
| 82 | 3-(1(S)-(4-Chlorobenzyl)-2(S)-((1-(4-methylthiophenyl)-2-cyano-ethyl)amino)propyl)benzonitrile (Diastereomer B) | 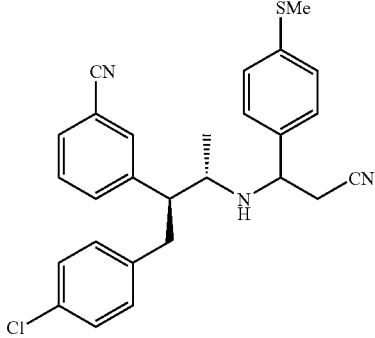 | 3.17 | 460 462 |
| 83 | 3-(1(S)-(4-Chlorobenzyl)-2(S)-((1-(4-cyanophenyl)-2-cyanoethyl)amino)propyl)benzonitrile (Diastereomer A) | 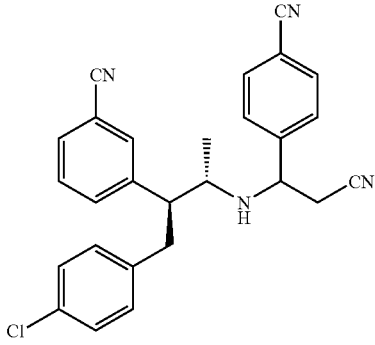 | 3.62 | 439 441 |
| 84 | 3-(1(S)-(4-Chlorobenzyl)-2(S)-((1-(4-methoxyphenyl)-2-cyanoethyl)amino)propyl)benzonitrile (Diastereomer A) | 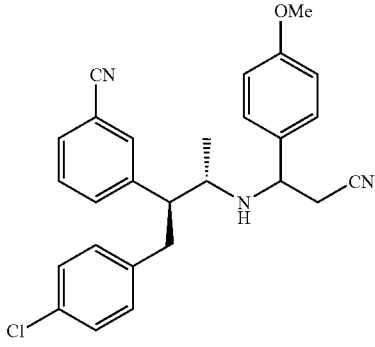 | 3.20 | 444 446 |

TABLE 2-continued

EXAMPLES 81–88

| Ex. No. | Name | Structure | retention time (min) | HPLC-mass spectrum m/e |
|---|---|---|---|---|
| 85 | 3-(1(S)-(4-Chlorobenzyl)-2(S)-((1-(3-methylthiophenyl)-2-cyano-ethyl)amino)propyl)benzonitrile (Diastereomer A) | 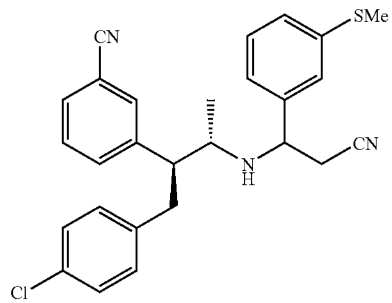 | 3.40 | 460 462 |
| 86 | 3-(1(S)-(4-Chlorobenzyl)-2(S)-((1-(3-methylthiophenyl)-2-cyano-ethyl)amino)propyl)benzonitrile (Diastereomer B) | 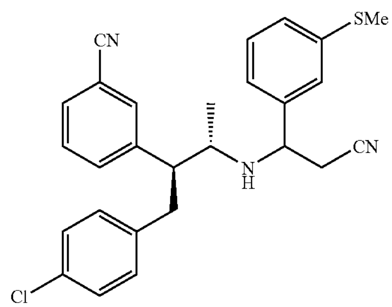 | 3.28 | 460 462 |
| 87 | 3-(1(S)-(4-Chlorobenzyl)-2(S)-((1-biphenyl-3-yl-2-cyanoethyl)amino)propyl)benzonitrile (Diastereomer A) | 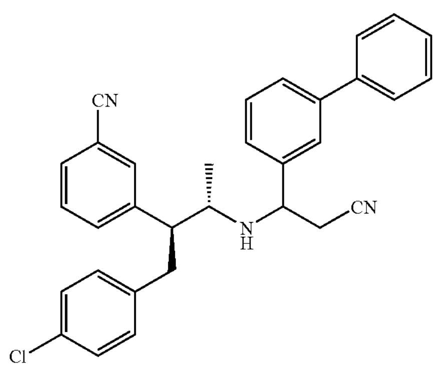 | 3.56 | 490 492 |
| 88 | 3-(1(S)-(4-Chlorobenzyl)-2(S)-((1-biphenyl-3-yl-2-cyanoethyl)amino)propyl)benzonitrile (Diastereromer B) | 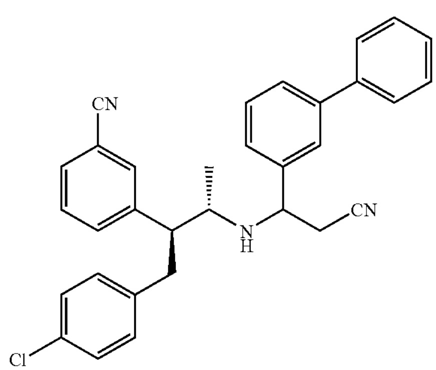 | 3.45 | 490 492 |

EXAMPLE 89

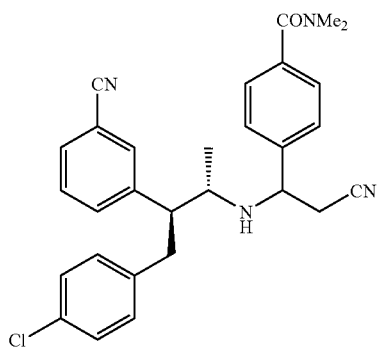

3-(1(S)-(4-Chlorobenzyl)-2(S)-((1-(4-dimethylaminocarbonylphenyl)-2-cyanoethyl)amino)propyl)benzonitrile (Diastereomer A)

To 0.7 mL of 1M dimethylamine in hexane, 0.35 mL of 2M trimethylaluminum in hexane was added. After 10 min 83 mg (0.175 mmol) of 3-(1(S)(4-chlorobenzyl)-2(S)-((1-(3-methoxycarbonylphenyl)-2-cyanoethyl)amino)propyl)benzonitrile (Diastereomer A) in 1 mL of toluene was added. After stirring for 1 hr, the mixture was heated in a 60° C. bath overnight. The reaction was neutralized with 1.2 N HCl and extracted with EtOAc. The organic layer was washed with brine, dried and concentrated. The residue was purified by prep TLC using 50% EtOAc-hexane to isolate the title compound. LC-MS: m/e=485 (M+1), 487 (M+3) (2.97 min).

EXAMPLE 90

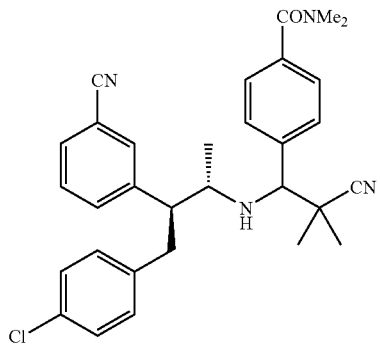

3-(1(S)-(4-Chlorobenzyl)-2(S)-(1-(4-dimethylaminocarbonylphenyl)-2-cyano-2-methylpropyl)amino)propyl)benzonitrile (Diastereomer A)

This compound was prepared from 3-(1(S)-(4-chlorobenzyl)-2(S)-((1-(4-dimethylaminocarbonylphenyl)-2-cyanoethyl)amino)propyl)benzonitrile (Diastereomer A) by the method of example 48. LC-MS: m/e=513 (M+1), 515 (M+3) (3.69 min).

EXAMPLE 91

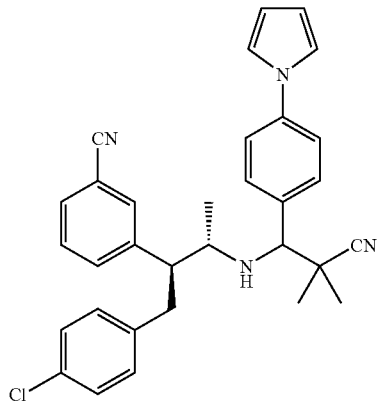

3-(1(S)-(4-Chlorobenzyl)-2(S)-((1-(4-(1H-pyrrol-1-yl)phenyl)-2-cyano-2-methylpropyl)amino)propyl) benzonitrile (Diastereomer A)

Step A: 3-(1(S)-(4-Chlorobenzyl)-2(S)-((1-(4-(1H-pyrrol-1-yl)phenyl)-2-cyanoethyl)amino)propyl) benzonitrile (Diastereomer A)

This compound was obtained from methyl 4-(1H-pyrrol-1-yl)-benzoate by the procedure of EXAMPLE 47.

Step B: 3-(1(S)-(4-Chlorobenzyl)-2(S)-((1-(4-(1H-pyrrol-1-yl)phenyl)-2-cyano-2-methylpropyl)amino) propyl)benzonitrile (Diastereomer A)

The title compound was prepared by the method of EXAMPLE 48. LC-MS: m/e=507 (M+1), 509 (M+3) (4.25 min).

The compounds of EXAMPLES 92-94 were prepared by a procedure analogous to example 91.

EXAMPLE 92

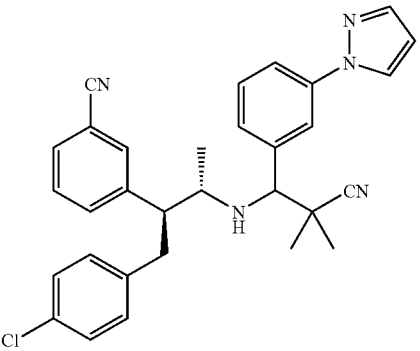

3-(1(S)-(4-Chlorobenzyl)-2(S)-((1-(3-(1H-pyrazol-1-yl)phenyl)-2-cyano-2-methylpropyl)amino)propyl) benzonitrile (Diastereomer A)

LC-MS: m/e=508 (M+1), 510 (M+3) (4.18 min).

EXAMPLE 93

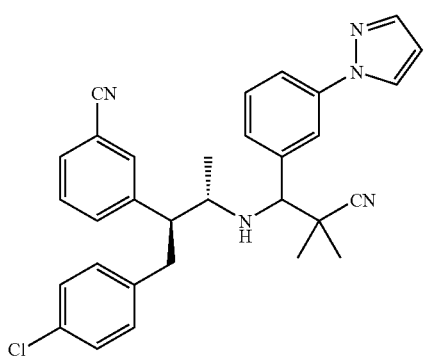

3-(1(S)-(4-Chlorobenzyl)-2(S)-((1-(3-(1H-pyrazol-1-yl)phenyl)-2-cyano-2-methylpropyl)amino)propyl)benzonitrile (Diastereomer B)

LC-MS: m/e=508 (M+1), 510 (M+3) (4.09 min).

EXAMPLE 94

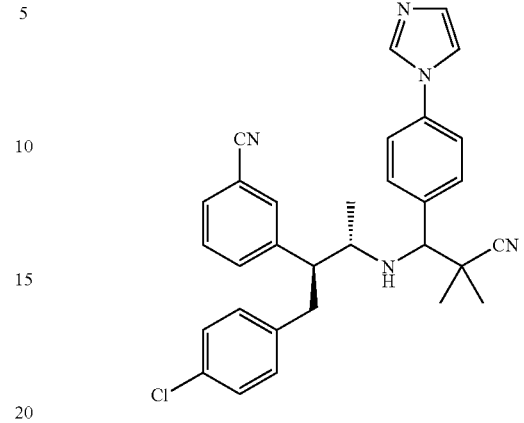

3-(1(S)-(4-Chlorobenzyl)-2(S)-((1-(4-(1H-imidazol-1-yl)phenyl)-2-cyano-2-methylpropyl)amino)propyl)benzonitrile (Diastereomer A)

LC-MS: m/e=508 (M+1), 510 (M+3) (3.15 min).

The compounds in TABLE 3 were synthesized by the procedure described in EXAMPLE 48.

TABLE 3

EXAMPLES 95–113

| Ex. No. | Name | Structure | retention time (min) | HPLC-mass spectrum m/e |
|---|---|---|---|---|
| 95 | 3-(1(S)-(4-Chlorobenzyl)-2(S)-((1-(4-chlorophenyl)-2-cyano-2-methylpropyl)amino)propyl)benzonitrile (Diastereomer A) | 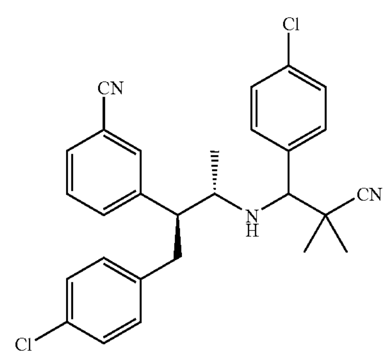 | 4.42 | 476 478 |
| 96 | 3-(1(S)-(4-Chlorobenzyl)-2(S)-((1-(4-chlorophenyl)-2-cyano-2-methylpropyl)amino)propyl)benzonitrile (Diastereomer B) | 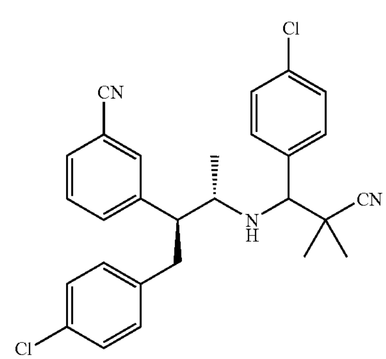 | 4.39 | 476 478 |

TABLE 3-continued

EXAMPLES 95–113

| Ex. No. | Name | Structure | HPLC-retention time (min) | mass spectrum m/e |
|---|---|---|---|---|
| 97 | 3-(1(S)-(4-Chlorobenzyl)-2(S)-((1-(4-fluorophenyl)-2-cyano-2-methylpropyl)amino)propyl)benzonitrile (Diastereomer A) | 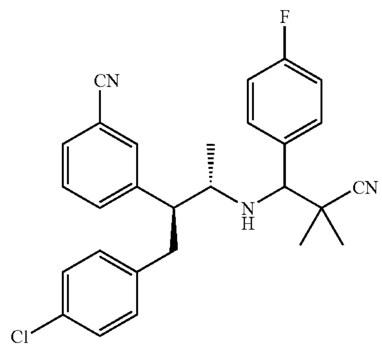 | 4.21 | 460 462 |
| 98 | 3-(1(S)-(4-Chlorobenzyl)-2(S)-((1-(3-chlorophenyl)-2-cyano-2-methylpropyl)amino)propyl)benzonitrile (Diastereomer A) | 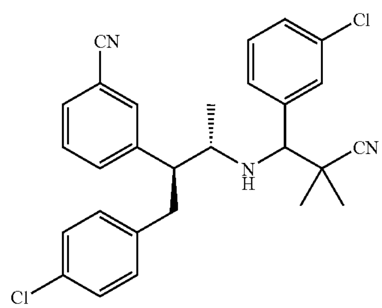 | 4.37 | 476 478 |
| 99 | 3-(1(S)-(4-Chlorobenzyl)-2(S)-((1-(3-trifluoromethylphenyl)-2-cyano-2-methylpropyl)amino)propyl)benzonitrile (Diastereomer A) | 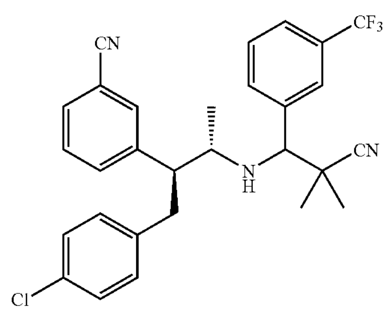 | 4.39 | 510 512 |
| 100 | 3-(1(S)-(4-Chlorobenzyl)-2(S)-((1-(4-trifluoromethylphenyl)-2-cyano-2-methylpropyl)amino)propyl)benzonitrile (Diastereomer A) | 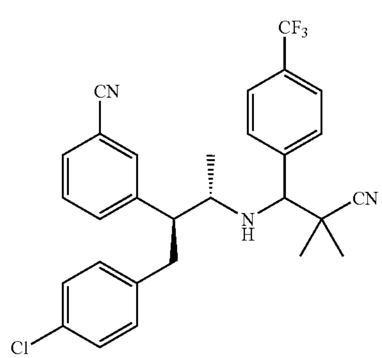 | 4.40 | 510 512 |

TABLE 3-continued

EXAMPLES 95–113

| Ex. No. | Name | Structure | retention time (min) | HPLC-mass spectrum m/e |
|---|---|---|---|---|
| 101 | 3-(1(S)-(4-Chlorobenzyl)-2(S)-((1-(4-methylphenyl)-2-cyano-2-methylpropyl)amino)propyl) benzonitrile (Diastereomer A) | 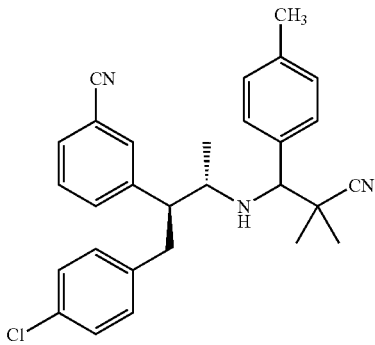 | 4.00 | 456 458 |
| 102 | 3-(1(S)-(4-Chlorobenzyl)-2(S)-((1-(4-methoxycarbonylphenyl)-2-cyano-2-methylpropyl)amino)propyl) benzonitrile (Diastereomer A) | 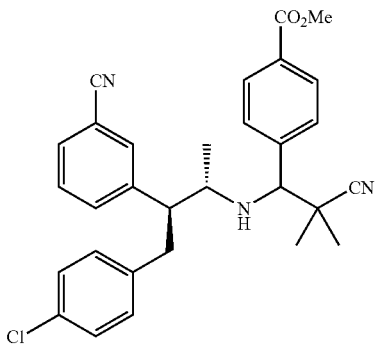 | 4.14 | 500 502 |
| 103 | 3-(1(S)-(4-Chlorobenzyl)-2(S)-((1-(4-trifluoromethoxyphenyl)-2-cyano-2-methylpropyl)amino)propyl) benzonitrile (Diastereomer A) | 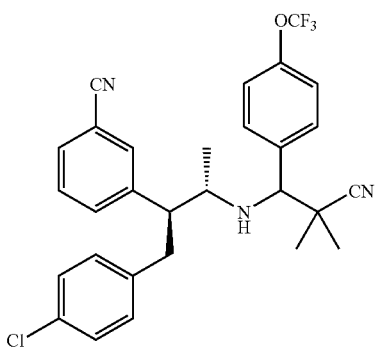 | 4.43 | 526 528 |
| 104 | 3-(1(S)-(4-Chlorobenzyl)-2(S)-((1-(3-methylphenyl)-2-cyano-2-methylpropyl)amino)propyl) benzonitrile (Diastereomer A) | 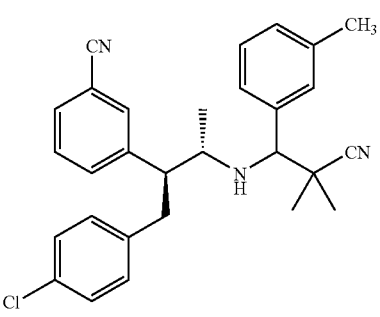 | 4.16 | 456 458 |

TABLE 3-continued

EXAMPLES 95–113

| Ex. No. | Name | Structure | retention time (min) | HPLC-mass spectrum m/e |
|---|---|---|---|---|
| 105 | 3-(1(S)-(4-Chlorobenzyl)-2(S)-((1-(4-cyanophenyl)-2-cyano-2-methylpropyl)amino)propyl)benzonitrile (Diastereomer A) | 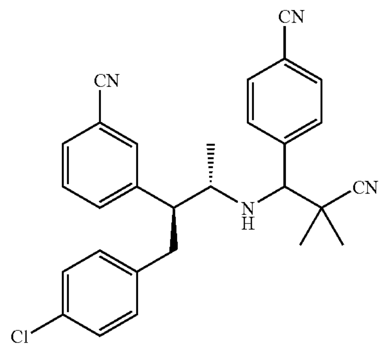 | 4.11 | 467 469 |
| 106 | 3-(1(S)-(4-Chlorobenzyl)-2(S)-((1-(3,4-dichlorophenyl)-2-cyano-2-methylpropyl)amino)propyl)benzonitrile (Diastereomer A) | 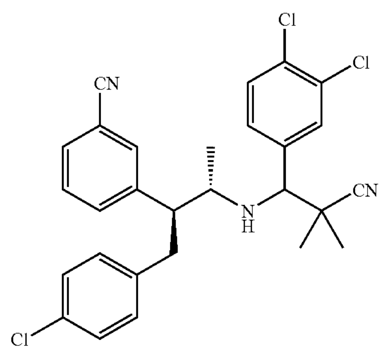 | 4.50 | 510 512 |
| 107 | 3-(1(S)-(4-Chlorobenzyl)-2(S)-((1-(2-chlorophenyl)-2-cyano-2-methylpropyl)amino)propyl)benzonitrile (Diastereomer A) | 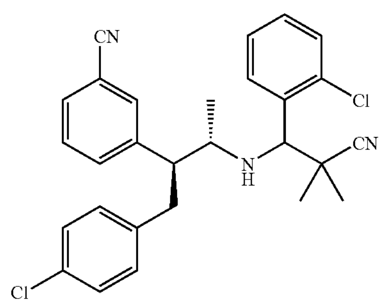 | 4.46 | 476 478 |
| 108 | 3-(1(S)-(4-Chlorobenzyl)-2(S)-((1-(4-methylthiophenyl)-2-cyano-2-methylpropyl)amino)propyl)benzonitrile (Diastereomer A) | 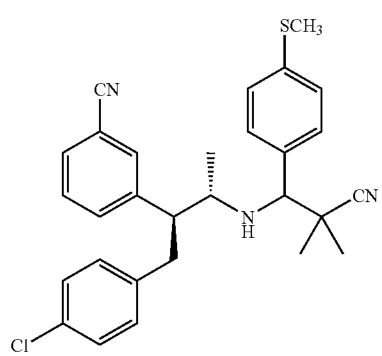 | 4.01 | 488 490 |

TABLE 3-continued

EXAMPLES 95–113

| Ex. No. | Name | Structure | retention time (min) | HPLC-mass spectrum m/e |
|---|---|---|---|---|
| 109 | 3-(1(S)-(4-Chlorobenzyl)-2(S)-((1-(4-methoxyphenyl)-2-cyano-2-methylpropyl)amino)propyl)benzonitrile (Diastereomer A) | 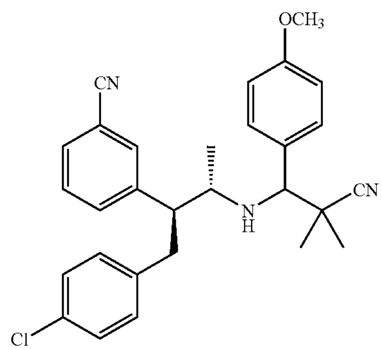 | 3.83 | 494 496 |
| 110 | 3-(1(S)-(4-Chlorobenzyl)-2(S)-((1-(3-methylthiophenyl)-2-cyano-2-methylpropyl)amino)propyl)benzonitrile (Diastereomer A) | 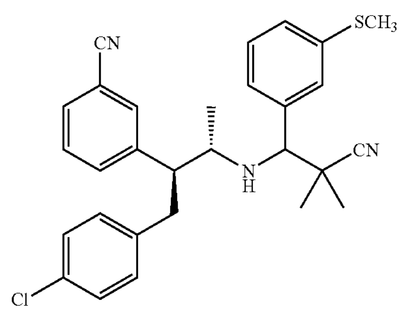 | 4.26 | 488 490 |
| 111 | 3-(1(S)-(4-Chlorobenzyl)-2(S)-((1-(3-phenylphenyl)-2-cyano-2-methylpropyl)amino)propyl)benzonitrile (Diastereomer A) | 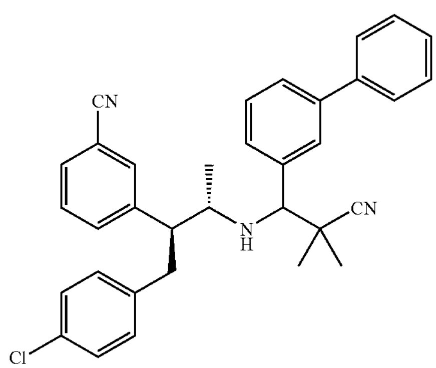 | 4.40 | 518 520 |
| 112 | 3-(1(S)-(4-Chlorobenzyl)-2(S)-((1-(4-bromophenyl)-2-cyano-2-methylpropyl)amino)propyl)benzonitrile (Diastereomer A) | 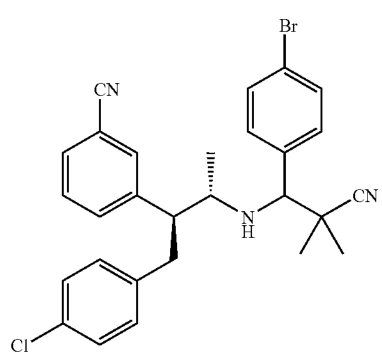 | 4.42 | 520 522 |

TABLE 3-continued

EXAMPLES 95–113

| Ex. No. | Name | Structure | retention time (min) | HPLC-mass spectrum m/e |
|---|---|---|---|---|
| 113 | 3-(1(S)-(4-Chlorobenzyl)-2(S)-((1-cyclohexyl-2-cyano-2-methylpropyl)amino)propyl)benzonitrile (Diastereomer A) | 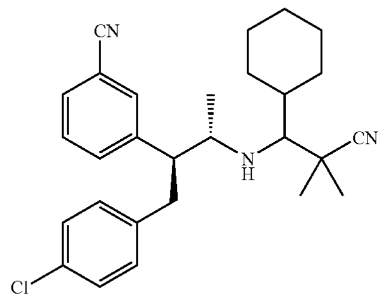 | 4.30 | 448 450 |

EXAMPLE 114

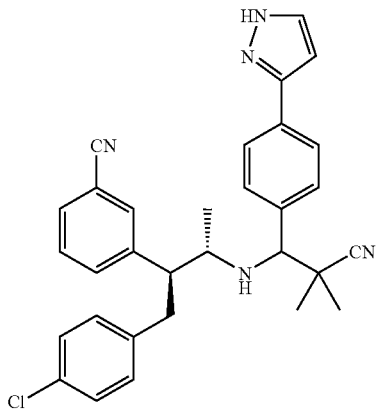

3-(1(S)-4-Chlorobenzyl)-2(S)-(1-(4-(1H-pyrazol-3-yl)phenyl)-2-cyano-2-methylpropyl)amino)propyl)benzonitrile (Diastereomer A)

To a solution of 49 mg (0.094 mmol) 3-(1(S)-4-chlorobenzyl)-2(S)-(1-(4-bromophenyl)-2-cyano-2-methylpropyl)amino)propyl)benzonitrile (Diastereomer A) in 0.5 mL of methanol and 1 mL of toluene, 12 mg (0.094 mmol) of pyrimidine-5-boronic acid, 32.5 mg (0.235 mmol) of $K_2CO_3$, and 11 mg (0.0094 mmol) of tetrakis(triphenylphosphine)palladium were added. The mixture was heated in a microwave reactor at 120° C. for 10 min. After the reaction cooled to room temperature, it was purified on a prep TLC plate using 40% EtOAc-hexane to isolate the title compound. LC-MS: m/e=508 (M+1), 510 (M+3) (3.68 min).

The compounds in TABLE 4 were prepared by reacting the appropriate boronic acid with either 3-(1(S)-(4-chlorobenzyl)-2(S)(1-(4-bromophenyl)-2-cyano-2-methylpropyl)amino)propyl)benzonitrile or 3-(1(S)-(4-chlorobenzyl)-2(S)-((1-(3-bromophenyl)-2-cyano-2-methylpropyl)amino)propyl)benzonitrile as described in EXAMPLE 114.

TABLE 4

EXAMPLES 115–125

| Ex. No. | Name | Structure | retention time (min) | HPLC-mass spectrum m/e |
|---|---|---|---|---|
| 115 | 3-(1(S)-(4-Chlorobenzyl)-2(S)-((1-(4-pyridin-4-yl-phenyl)-2-cyano-2-methylpropyl)amino)propyl)benzonitrile (Diasteromer A) | 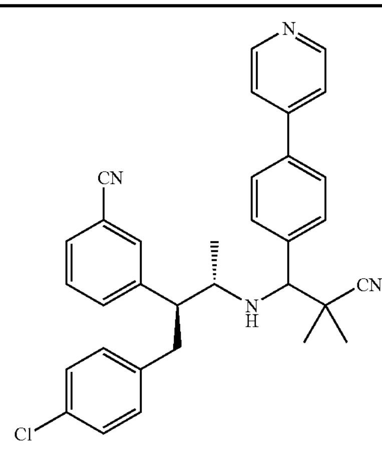 | 3.22 | 519 521 |

TABLE 4-continued

EXAMPLES 115–125

| Ex. No. | Name | Structure | retention time (min) | HPLC-mass spectrum m/e |
|---|---|---|---|---|
| 116 | 3-(1(S)-(4-Chlorobenzyl)-2(S)-((1-(4-pyridin-3-yl-phenyl)-2-cyano-2-methylpropyl)amino) = propyl) benzonitrile (Diastereomer A) | 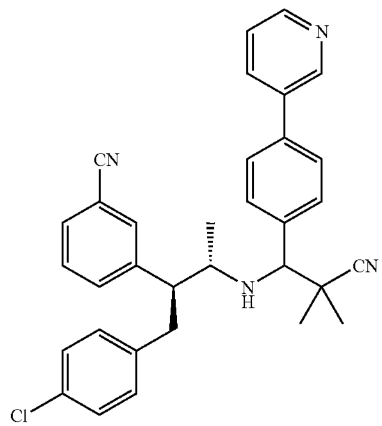 | 3.26 | 519 521 |
| 117 | 3-(1(S)-(4-Chlorobenzyl)-2(S)-((1-(4'-cyanbiphen-4-yl)-2-cyano-2-methylpropyl)amino)propyl) benzonitrile (Diastereomer A) | 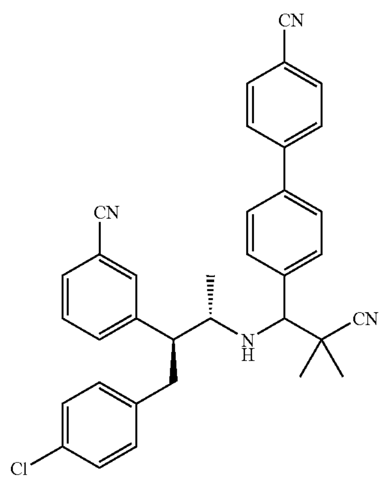 | 4.28 | 543 545 |
| 118 | 3-(1(S)-(4-Chlorobenzyl)-2(S)-((1-(4-pyrimidin-5-yl-phenyl)-2-cyano-2-methylpropyl)amino)propyl) benzonitrile (Diastereomer A) | 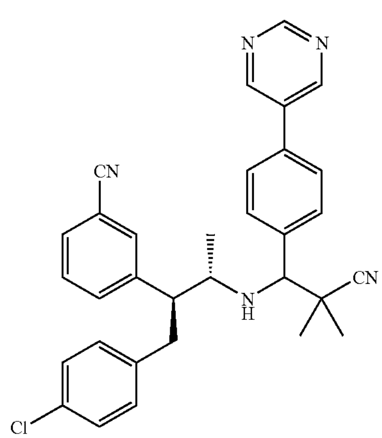 | 3.86 | 520 522 |

TABLE 4-continued

EXAMPLES 115–125

| Ex. No. | Name | Structure | retention time (min) | HPLC-mass spectrum m/e |
|---|---|---|---|---|
| 119 | 3-(1(S)-(4-Chlorobenzyl)-2(S)-((1-(4-(2-fluoropyridin-4-yl)-phenyl)-2-cyano-2-methylpropyl)amino)propyl)benzonitrile (Diastereomer A) | 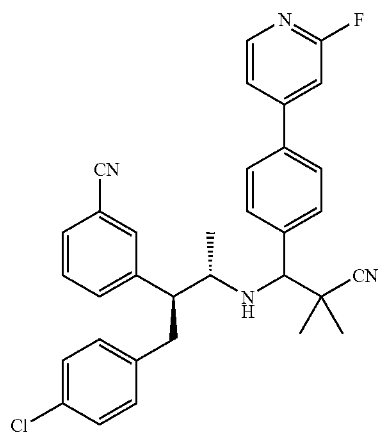 | 3.97 | 537 539 |
| 120 | 3-(1(S)-(4-Chlorobenzyl)-2(S)-((1-(4'-cyanobiphen-3-yl)-2-cyano-2-methylpropyl)amino)propyl)benzonitrile (Diastereomer A) | 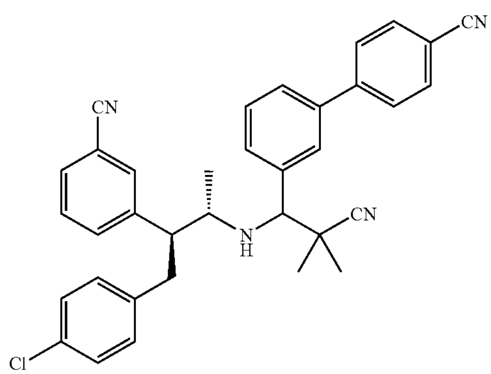 | 4.28 | 543 545 |
| 121 | 3-(1(S)-(4-Chlorobenzyl)-2(S)-((1-(3-pyridin-3-yl-phenyl)-2-cyano-2-methylpropyl)amino)propyl)benzonitrile (Diastereomer A) | 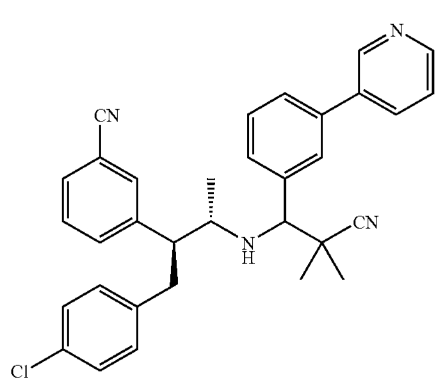 | 3.35 | 519 521 |

TABLE 4-continued

EXAMPLES 115–125

| Ex. No. | Name | Structure | HPLC-retention time (min) | mass spectrum m/e |
|---|---|---|---|---|
| 122 | 3-(1(S)-(4-Chlorobenzyl)-2(S)-((1-(3-pyrimidin-5-yl-phenyl)-2-cyano-2-methylpropyl)amino)propyl)benzonitrile (Diastereomer A) | 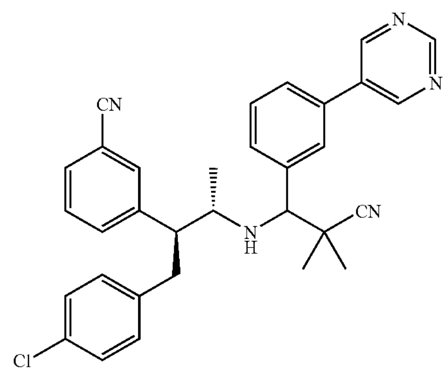 | 3.87 | 520 522 |
| 123 | 3-(1(S)-(4-Chlorobenzyl)-2(S)-((1-(3-pyridin-4-yl-phenyl)-2-cyano-2-methylpropyl)amino)propyl)benzonitrile (Diastereomer A) | 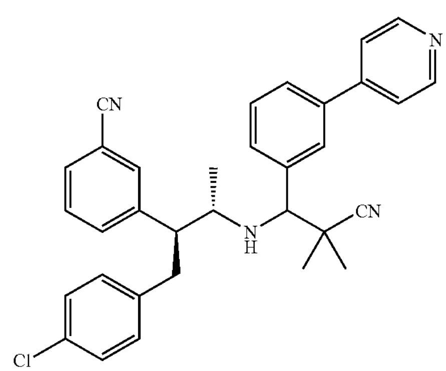 | 3.29 | 519 521 |
| 124 | 3-(1(S)-(4-Chlorobenzyl)-2(S)-((1-(3-(1H-pyrazol-3-yl)-phenyl)-2-cyano-2-methylpropyl)amino)propyl)benzonitrile (Diastereomer A) | 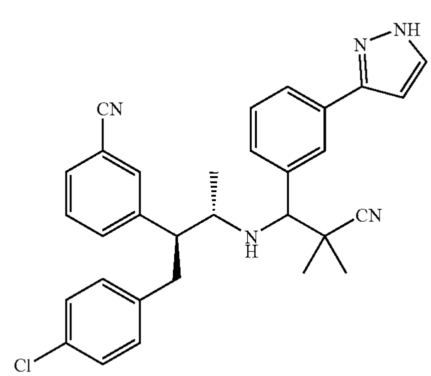 | | |

TABLE 4-continued

EXAMPLES 115–125

| Ex. No. | Name | Structure | retention time (min) | HPLC-mass spectrum m/e |
|---|---|---|---|---|
| 125 | 3-(1(S)-(4-Chlorobenzyl)-2(S)-((1-(3'-cyanobiphen-3-yl)-2-cyano-2-methylpropyl)amino)propyl)benzonitrile (Diastereomer A) | 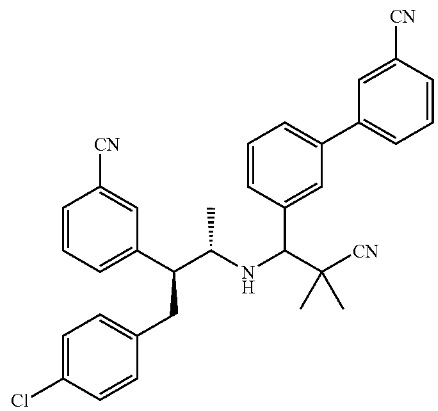 | 4.29 | 543 545 |

EXAMPLE 126 AND 127

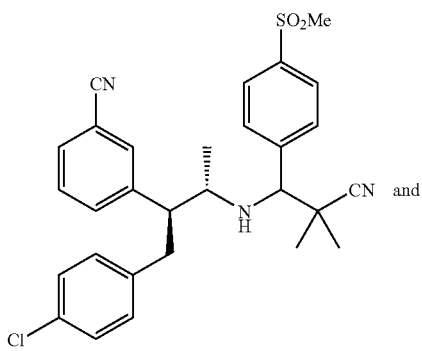

and

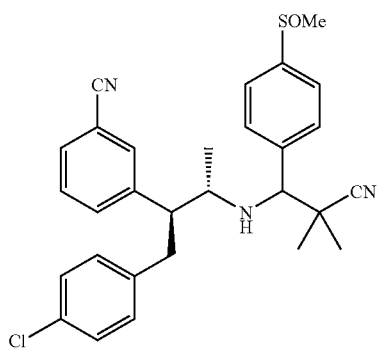

3-(1(S)-(4-Chlorobenzyl)-2(S)-((1-(4-methanesulfonylphenyl)-2-cyano-2-methylpropyl)amino)propyl)benzonitrile (Diastereomer A) and 3-(1 (S)-(4-Chlorobenzyl)-2(S)-((1-(4-methanesulfonylphenyl)-2-cyano-2-methylpropyl)amino)propyl)benzonitrile (Diastereomer A)

A solution of 49 mg (0.1 mmol) 3-(1(S)-(4-Chlorobenzyl)-2(S)-((1-(4-methylthiophenyl)-2-cyano-2-methylpropyl)amino)propyl)benzonitrile (Diastereomer A) in 1 mL of methanol was cooled in ice bath and 186 mg (0.3 mmol) of oxone in 1 mL of water was added. The bath was removed and the reaction was stirred for 3 hr. The solution was diluted with EtOAc, washed with water, brine, dried and concentrated. The residue was purified on a prep TLC plate using 50% EtOAC-hexane to isolate 3-(1(S)-(4-Chlorobenzyl)-2(S)-((1-(4-methanesulfonylphenyl)-2-cyano-2-methylpropyl)no)propyl)benzonitrile, LC-MS: m/e=520 (M+1), 522 (M+3) (3.88 min). and 7 mg of 3-(1(S)-(4-Chlorobenzyl)-2(S)-((1-(4-methanesulfonylphenyl)-2-cyano-2-methylpropyl)amino)propyl)benzonitrile. LC-MS: m/e=504 (M+1), 506 (M+3) (3.32 min).

EXAMPLE 128 AND 129

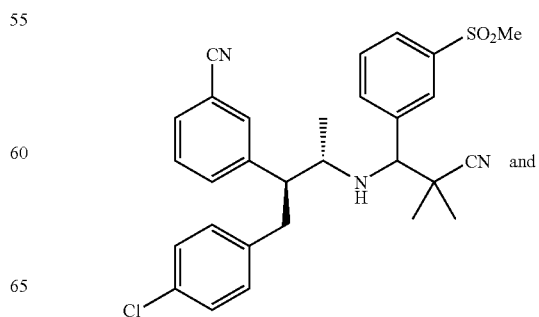

and

EXAMPLE 130

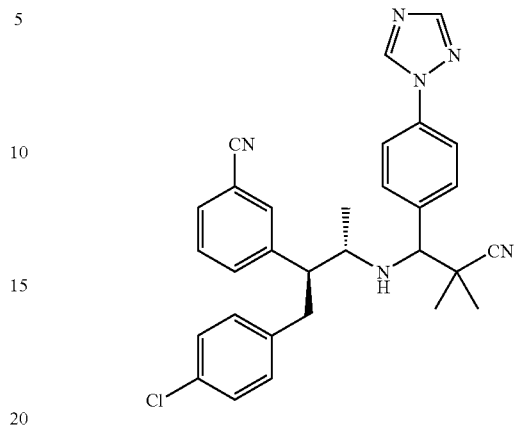

3-(1(S)-(4-Chlorobenzyl)-2(S)-((1-(4-(1H-1,2,4-triazol-1-yl)phenyl)-2-cyano-2-methylpropyl)amino)propyl)benzonitrile (Diastereomer A)

To a solution of 22.5 mg (0.043 mmol) of 3-(1(S)-(4-chlorobenzyl)-2(S)-((1-(4-bromophenyl)-2-cyano-2-methylpropyl)amino)propyl)benzonitrile in 0.5 mL of N-methylpyrrolidone, 12 mg (0.173 mmol) of 1,2,4-triazole, 2.3 mg of CuI and 24 mg of $K_2CO_3$ were added. The mixture was heated in a microwave reactor at 195° C. for 4 hr. The reaction was diluted with ether, washed with water, brine, dried and concentrated. The residue was purified by prep TLC using 50% EtOAc-hexane to isolate the title compound.

The compounds in TABLE 5 were synthesized by the method of EXAMPLE 130 using either 3-(1(S)-(4-chlorobenzyl)-2(S)-((1-(4-bromophenyl)-2-cyano-2-methylpropyl)amino)propyl)benzonitrile or 3-(1(S)-(4-chlorobenzyl)-2(S)-((1-(3-bromophenyl)-2-cyano-2-methylpropyl)amino)propyl)benzonitrile.

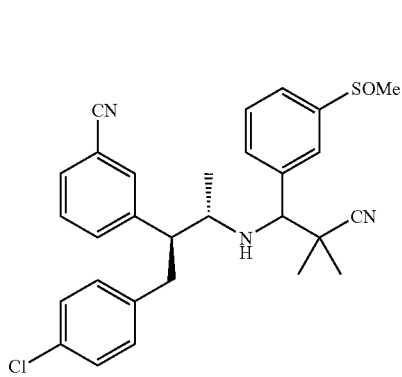

3-(1(S)-(4-Chlorobenzyl)-2(S)-((1-(3-methanesulfonylphenyl)-2-cyano-2-methylpropyl)amino)propyl)benzonitrile (Diastereomer A) and 3-(1(S)-(4-Chlorobenzyl)-2(S)-((1-(3-methanesulfonylphenyl)-2-cyano-2-methylpropyl)amino)propyl)benzonitrile (Diastereomer A)

The title compounds were prepared by the procedure of EXAMPLES 126-127. LC-MS: m/e=520 (M+1), 522 (M+3) (3.90 min) and LC-MS: m/e=504 (M+1), 506 (M+3) (3.69 min).

TABLE 5

EXAMPLES 131–142

| Ex. No. | Name | Structure | retention time (min) | HPLC-mass spectrum m/e |
|---|---|---|---|---|
| 131 | 3-(1(S)-(4-Chlorobenzyl)-2(S)-((1-(4-(1H-1,2,5-triazol-1-yl)phenyl-2-cyano-2-methylpropyl)amino)propyl)benzonitrile (Diastereomer A) | 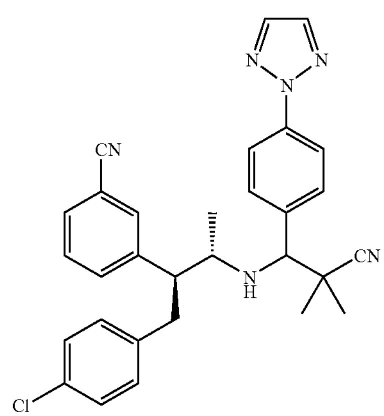 | 4.1 | 509 |

TABLE 5-continued

EXAMPLES 131–142

| Ex. No. | Name | Structure | retention time (min) | HPLC-mass spectrum m/e |
|---|---|---|---|---|
| 132 | 3-(1(S)-(4-Chlorobenzyl)-2(S)-((1-(4-(1H-1,2,3-triazol-1-yl)phenyl)-2-cyano-2-methylpropyl)amino)propyl)benzonitrile (Diastereomer A) | 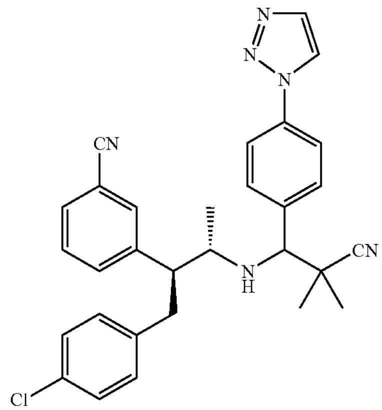 | 3.8 | 509 511 |
| 133 | 3-(1(S)-(4-Chlorobenzyl)-2(S)-((1-(3-(1H-1,2,4-triazol-1-yl)phenyl)-2-cyano-2-methylpropyl)amino)propyl)benzonitrile (Diastereomer A) | 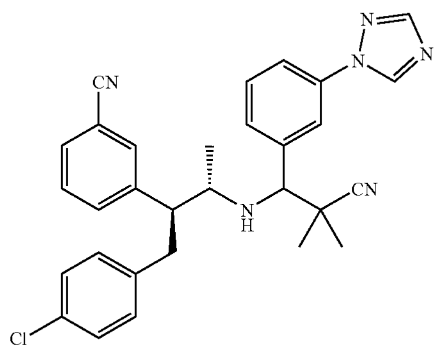 | 3.9 | 509 511 |
| 134 | 3-(1(S)-(4-Chlorobenzyl)-2(S)-((1-(3-(1H-1,2,5-triazol-1-yl)phenyl)-2-cyano-2-methylpropyl)amino)propyl)benzonitrile (Diastereomer A) | 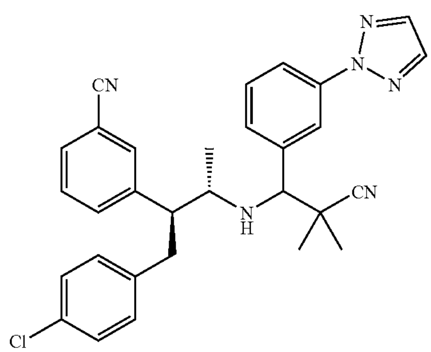 | 4.2 | 509 511 |
| 135 | 3-(1(S)-(4-Chlorobenzyl)-2(S)-((1-(3-(1H-1,2,3-triazol-1-yl)phenyl)-2-cyano-2-methylpropyl)amino)propyl)benzonitrile (Diastereomer A) | 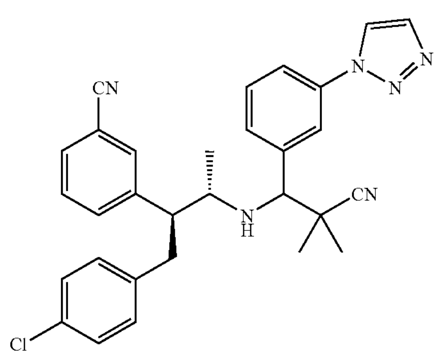 | 3.9 | 509 511 |

TABLE 5-continued

EXAMPLES 131–142

| Ex. No. | Name | Structure | HPLC-retention time (min) | mass spectrum m/e |
|---|---|---|---|---|
| 136 | 3-(1(S)-(4-Chlorobenzyl)-2(S)-((1-(4-(1H-pyrazol-1-yl)phenyl)-2-cyano-2-methylpropyl)amino)propyl)benzonitrile (Diastereomer A) | 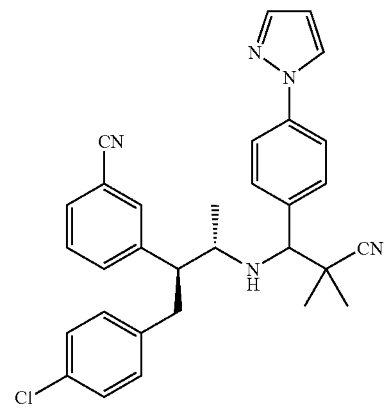 | 4.1 | 508 |
| 137 | 3-(1(S)-(4-Chlorobenzyl)-2(S)-((1-(4-(1H-pyrazol-3-ylamino)phenyl)-2-cyano-2-methylpropyl)amino)propyl)benzonitrile (Diastereomer A) | 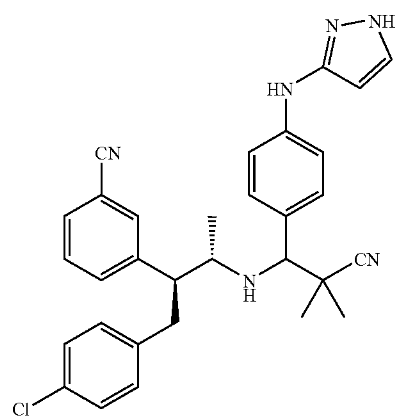 | 3.5 | 523 525 |
| 138 | 3-(1(S)-(4-Chlorobenzyl)-2(S)-((1-(4-(1H-1,2,4-triazol-3-ylamino)phenyl)-2-cyano-2-methylpropyl)amino)propyl)benzonitrile (Diastereomer A) | 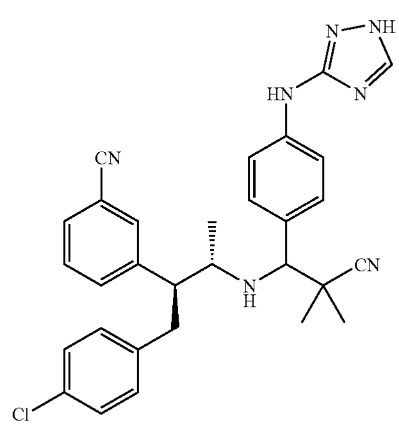 | 3.4 | 524 526 |

TABLE 5-continued

EXAMPLES 131–142

| Ex. No. | Name | Structure | retention time (min) | HPLC-mass spectrum m/e |
|---|---|---|---|---|
| 139 | 3-(1(S)-(4-Chlorobenzyl)-2(S)-((1-(4-(3-amino-1H-1,2,4-triazol-1-yl)phenyl)-2-cyano-2-methyl-propyl)amino)propyl)benzonitrile (Diastereomer A) | 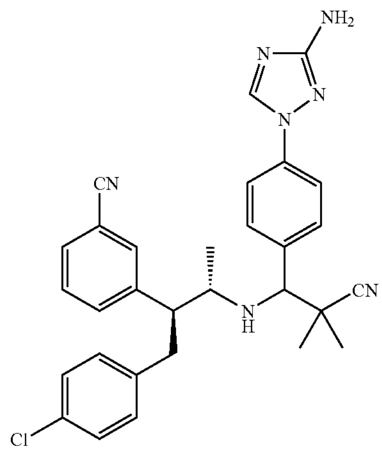 | 3.3 | 524 526 |
| 140 | 3-(1(S)-(4-Chlorobenzyl)-2(S)-((1-(3-(1H-pyrazol-3-ylamino)phenyl)-2-cyano-2-methylpropyl)amino) propyl)benzonitrile (Diastereomer A) | 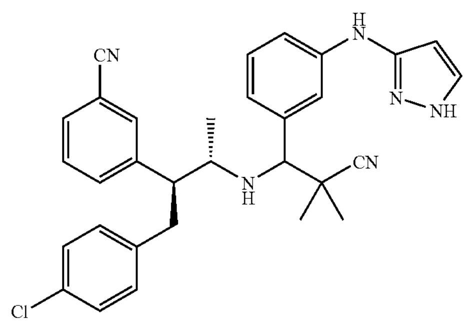 | 3.6 | 523 525 |
| 141 | 3-(1(S)-(4-Chlorobenzyl)-2(S)-((1-(3-(1H-1,2,4-triazol-3-ylamino)phenyl)-2-cyano-2-methylpropyl)amino)propyl) benzonitrile (Diastereomer A) | 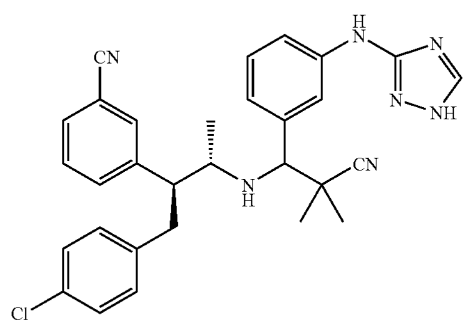 | 3.5 | 524 526 |
| 142 | 3-(1(S)-(4-Chlorobenzyl)-2(S)-((1-(3-(pyridine-2-ylamino)phenyl)-2-cyano-2-methylpropyl)amino) propyl)benzonitrile (Diastereomer A) | 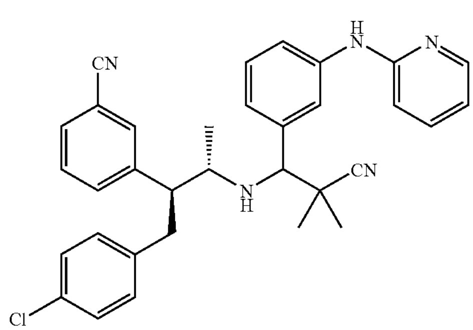 | 3.3 | 524 526 |

BIOLOGICAL EXAMPLE 1

Cannabinoid Receptor-1 (CB1) Binding Assay.

Binding affinity determination is based on recombinant human CB1 receptor expressed in Chinese Hamster Ovary (CHO) cells (Felder et al, Mol. Pharmacol. 48: 443-450, 1995). Total assay volume is 250 μL (240 μL CB1 receptor membrane solution plus 5 μL test compound solution plus 5 μL [3H]CP-55940 solution). Final concentration of [3H]CP-55940 is 0.6 nM. Binding buffer contains 50 mM Tris-HCl, pH7.4, 2.5 mM EDTA, 5 nM $MgCl_2$, 0.5 mg/mL fatty acid free bovine serum albumin and protease inhibitors (Cat#P8340, from Sigma). To initiate the binding reaction, 5 μL of radioligand solution is added, the mixture is incubated with gentle shaking on a shaker for 1.5 hours at 30° C. The binding is terminated by using 96-well harvester and filtering through GF/C filter presoaked in 0.05% polyethylenimine. The bound radiolabel is quantitated using scintillation counter. Apparent binding affinities for various compounds are calc'd from $IC_{50}$ values (DaBlasi et al., Trends Pharmacol Sci 10: 227-229, 1989).

The binding assay for CB2 receptor is done similarly with recombinant human CB2 receptor expressed in CHO cells.

The exemplified compounds were tested in the above assay and found to have an $IC_{50}$ value of 2 micromolar or less.

Selective CB1 antagonist/inverse agonist compounds have $IC_{50}$s 100-fold greater in the CB2 binding assay than in the CB1 assay, and generally have $IC_{50}$s of greater than one micromolar in the CB2 binding assay.

BIOLOGICAL EXAMPLE 2

Cannabinoid Receptor-1 (CB1) Functional Activity Assay.

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 μL of CB1-CHO cell suspension are mixed with test compound and 70 uL assay buffer containing 0.34 mM 3-isobutyl-1-methylxanthine and 5.1 μM of forskolin in 96-well plates. The assay buffer is comprised of Earle's Balanced Salt Solution supplemented with 5 mM $MgCl_2$, 1 mM glutamine, 10 mM HEPES, and 1 mg/mL bovine serum albumin. The mixture is incubated at room temperature for 30 minutes, and terminated by adding 30 μl/well of 0.5M HCl. The total intracellular cAMP level is quantitated using the New England Nuclear Flashplate and cAMP radioimmunoassay kit. To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

CB1 antagonist/inverse agonist compounds of the present invention generally have $EC_{50}$s of less than 1 micromolar in the CB1 functional assay and selective CB1 antagonist/inverse agonists have generally have $EC_{50}$s of greater than 1 micromolar in the CB2 functional assay.

BIOLOGICAL EXAMPLE 3

Acute Food Intake Studies in Rats or Mice: General Procedure

Adult rats or mice are used in these studies. After at least 2 days of acclimation to the vivarium conditions (controlled humidity and temperature, lights on for 12 hours out of 24 hours) food is removed from rodent cages. Experimental compounds or their vehicles are administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calc'd as grams of food eaten per gram of body weight within each time interval and the appetite-suppressant effect of the compounds are compared to the effect of vehicle. In these experiments many strains of mouse or rat, and several standard rodent chows can be used.

BIOLOGICAL EXAMPLE 4

Chronic Weight Reduction Studies in Rats or Mice: General Procedure

Adult rats or mice are used in these studies. Upon or soon after weaning, rats or mice are made obese due to exclusive access to diets containing fat and sucrose in higher proportions than in the control diet. The rat strains commonly used include the Sprague Dawley bred through Charles River Laboratories. Although several mouse strains may be used, c57B1/6 mice are more prone to obesity and hyperinsulinemia than other strains. Common diets used to induce obesity include: Research Diets D12266B (32% fat) or D12451 (45% fat) and BioServ S3282 (60% fat). The rodents ingest chow until they are significantly heavier and have a higher proportion of body fat than control diet rats, often 9 weeks. The rodents receive injections (1 to 4 per day) or continuous infusions of experimental compounds or their vehicles either orally, intraperitoneally, subcutaneously or intravenously. Food intake and body weights are measured daily or more frequently. Food intake is calc'd as grams of food eaten per gram of body weight within each time interval and the appetite-suppressant and weight loss effects of the compounds are compared to the effects of vehicle.

While the foregoing specification teaches the principles of the present invention, with examples provided for the purpose of illustration, it is understood that the practice of the invention encompasses all of the usual variations, adoptions, or modifications, as being within the scope of the following claims and their equivalents. It is intended, therefore, that the invention be defined by the scope of the claims which follow and that such claims be interpreted as broadly as is reasonable.

The invention claimed is:

1. A compound of structural formula I:

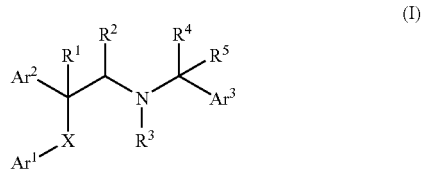

or a pharmaceutically acceptable salt thereof, wherein:
$R^1$ is
  (1) hydrogen
  (4);
$R^2$ is —$CH_3$,
  wherein each —$CH_3$ is unsubstituted or substituted with 1, 2 or 3 $R^e$ substituents;
$R^3$ is
  hydrogen
  (2);
$R^4$ is selected from:
  (1) hydrogen,
  (2) $C_{1-10}$alkyl,
  (3) $C_{2-10}$alkenyl,
  (4) $C_{2-10}$alkynyl,
  (5) $C_{1-10}$alkyloxycarbonyl-,
  (6) $C_{3-10}$cycloalkyl,
  (7) aryl-$C_{1-6}$alkyl-, and
  (8) heteroaryl-$C_{1-6}$alkyl-,
    wherein each alkyl, alkenyl, and alkynyl moiety is unsubstituted or substituted with one to four substituents independently selected from $R^a$ and each aryl, heteroaryl, and cycloalkyl moeity is unsubstituted or substituted with one, two or three substituents independently selected from $R^b$ and oxo;
$R^5$ is
  hydrogen
  (2);
$Ar^1$ is phenyl,
  (7)
  wherein each phenyl is unsubstituted or substituted with one to four substituents independently selected from $R^b$;
$Ar^2$ is phenyl,
  wherein each phenyl is unsubstituted or substituted with one to four substituents independently selected from $R^b$;
$Ar^3$ is phenyl,
  wherein each phenyl is unsubstituted or substituted with one to four substituents independently selected from $R^b$;
X is —$CH_2$-;
each $R^a$ is independently selected from:
  (1) —$OR^d$,
  (2) —$NR^cS(O)_mR^d$,
  (3) halogen,
  (4) —$SR^d$,
  (5) —$S(O)_mR^d$,
  (6) —$S(O)_mNR^cR^d$,
  (7) —$NR^cR^d$,
  (8) —$C(O)R^d$,
  (9) —$CO_2R^d$,
  (10) —CN,
  (11) —$C(O)NR^cR^d$,
  (12) —$NR^cC(O)R^d$,
  (13) —$NR^cC(O)OR^d$,
  (14) —$NR^cC(O)NR^cR^d$,
  (15) —$CF_3$,
  (16) —$OCF_3$, and
  (17) cycloheteroalkyl;
each $R^b$ is independently selected from:
  (1) $R^a$,
  (2) $C_{1-10}$alkyl,
  (3) aryl,
  (4) aryl$C_{1-4}$alkyl,
  (5) heteroaryl, and
  (6) heteroaryl$C_{1-4}$alkyl,
    wherein aryl and heteroaryl moieties are unsubstituted or substituted with one, two or three substituents independently selected from $R^f$;
$R^c$ and $R^d$ are independently selected from:
  (1) hydrogen,
  (2) $C_{1-10}$alkyl,
  (3) $C_{2-10}$ alkenyl,
  (4) cycloalkyl,
  (5) cycloalkyl-$C_{1-10}$alkyl-,
  (6) cycloheteroalkyl,
  (7) cycloheteroalkyl-$C_{1-10}$ alkyl-,
  (8) aryl,
  (9) heteroaryl,
  (10) aryl-$C_{1-10}$alkyl-, and
  (11) heteroaryl-$C_{1-10}$alkyl-, or
$R^c$ and $R^d$ together with the atom(s) to which they are attached form a heterocyclic ring of 4 to 7 members containing 0-2 additional heteroatoms independently selected from oxygen, sulfur and N—$R^g$,
each $R^c$ and $R^d$ are unsubstituted or substituted with one to three substituents selected from $R^h$;
$R^e$ is selected from:
  (1) hydroxy,
  (2) methoxy-,
  (3) trifluoromethoxy-,
  (4) methylcarbonyloxy-,
  (5) halogen, and
  (6) cyano;
$R^f$ is selected from:
  (1) halogen,
  (2) methyl,
  (3) cyano, and
  (4) amino;
each $R^g$ is independently selected from
  (1) $C_{1-10}$alkyl, and
  (2) —$C(O)R^i$;
each $R^h$ is independently selected from:
  (1) halogen,
  (2) $C_{1-10}$alkyl,
  (3) —O—$C_{1-4}$alkyl,
  (4) —S—$C_{1-4}$alkyl,
  (5) —CN,
  (6) —$NO_2$,
  (7) —$CF_3$, and
  (8) —$OCF_3$;
each $R^i$ is independently selected from:
  (1) hydrogen,
  (2) $C_{1-10}$alkyl,
  (3) $C_{2-10}$ alkenyl,
  (4) cycloalkyl,
  (5) cycloalkyl-$C_{1-10}$alkyl-,
  (6) cycloheteroalkyl,
  (7) cycloheteroalkyl-$C_{1-10}$ alkyl-,
  (8) aryl,
  (9) heteroaryl,
  (10) aryl-$C_{1-10}$alkyl-, and
  (11) heteroaryl-$C_{1-10}$alkyl-; and
m is selected from 1 and 2.

2. The compound according to claim 1, wherein:
X is
  —$CH_2$—;
each $R^a$ is independently selected from:
  (1) —$OR^d$,
  (2) —$NHS(O)_2R^d$,
  (3) halogen,
  (4) —$SR^d$,
  (5) —$S(O)_2R^d$ (6) —S(O)$_2$NR$^c$R$^d$,
(7) —NR$^c$R$^d$,
(8) —C(O)R$^d$,
(9) —CO$_2$R$^d$,
(10) —CN,
(11) —C(O)NR$^c$R$^d$,
(12) —NHC(O)R$^d$,
(13) —NHC(O)OR$^d$,
(14) —NHC(O)NR$^c$R$^d$,
(15) —CF$_3$, and
(16) —OCF$_3$;

each R$^b$ is independently selected from:
(1) R$^a$,
(2) C$_{1-3}$alkyl,
(3) phenyl, and
(4) heteroaryl,
wherein aryl and heteroaryl moieties are unsubstituted or substituted with one or two substituents independently selected from R$^f$, each R$^c$ is selected from hydrogen and methyl, and each R$^d$ is selected from:
(1) hydrogen,
(2) C$_{1-6}$alkyl,
(3) cycloalkyl,
(4) cycloalkyl-C$_{1-3}$alkyl-,
(5) cycloheteroalkyl,
(6) cycloheteroalkyl-C$_{1-3}$ alkyl-,
(7) phenyl,
(8) pyridyl,
(9) triazolyl,
(10) pyrazolyl
(11) phenyl-C$_{1-3}$alkyl-,
(12) pyridyl-C$_{1-3}$alkyl-,
(13) triazolyl-C$_{1-3}$alkyl-, and
(14) pyrazolyl-C$_{1-3}$alkyl-,
wherein each R$^c$ and R$^d$ may be unsubstituted or substituted with one to three substituents selected from R$^h$;

and pharmaceutically acceptable salts thereof.

3. The compound according to claim 1, wherein:
R$^4$ is selected from:
(1) C$_{1-6}$alkyl,
(2) C$_{1-5}$alkyloxycarbonyl-, and
(3) C$_{3-6}$cycloalkyl,
(4) aryl-C$_{1-3}$alkyl-, and
(5) heteroaryl-C$_{1-3}$alkyl-,
wherein each alkyl moiety is unsubstituted or substituted with one to two substituents independently selected from R$^a$ and each aryl, heteroaryl and cycloalkyl moeity is unsubstituted or substituted with a hydroxy or oxo substituent.

4. The compound according to claim 3, wherein: Ar$^3$ is phenyl, unsubstituted or substituted with one or two substituents selected from halogen, cyano, —CH$_3$, —OCH$_3$, —CF$_3$, —OCF$_3$, —CO$_2$CH$_3$, —SCH$_3$, —S(O)CH$_3$, —S(O)$_2$CH$_3$, —C(O)N(CH$_3$)$_2$, phenyl, pyridinyl, pyrimidinyl, pyrazolyl, pyrrolyl, triazolyl, —NH—R$^d$ wherein phenyl and heteroaryl moieties are unsubstituted or substituted with a substituent selected from halogen, methyl, cyano and amino,
and pharmaceutically acceptable salts thereof.

5. The compound according to claim 4, wherein: R$^2$ is methyl, X is —CH$_2$—, Ar$^1$ is 4-chlorophenyl, and Ar$^2$ is 3-cyanophenyl.

6. The compound according to claim 1 selected from:
(1) 3-(1(S)(4-chlorobenzyl)-2(S)-((2-hydroxy-2-methyl-1-phenylpropyl)amino)propyl)-benzonitrile,
(2) methyl ((3-(4-chlorophenyl)-2(S)-(3-cyanophenyl)-1(S)-methyl-propyl)-amino)(phenyl)acetate,
(3) 3-(1(S)-1-(4-chlorobenzyl)-2(S)-((2-hydroxy-1-phenylethyl)amino)-propyl)benzonitrile,
(4) 3-(1(S)-(4-chlorobenzyl)-2(S)-((2-methoxy-1-phenylethyl)amino)-propyl)-benzonitrile,
(5) 3-(1(S)-(4-chlorobenzyl)-2(S)-((1-(4-chlorophenyl)-2-hydroxy-2-methyl-propyl)amino)propyl)benzonitrile,
(6) 3-(1(S)-(4-chlorobenzyl)-2(S)-((1-(3,5-difluorophenyl)-2-hydroxy-2-methyl-propyl)amino)propyl)-benzonitrile,
(7) 3-(1(S)-(4-chlorobenzyl)-2(S)-((1-(2-chlorophenyl)-2-hydroxy-2-methyl-propyl)amino)propyl)-benzonitrile,
(8) 3-(1(S)-(4-chlorobenzyl)-2(S)-((1-(3-chlorophenyl)-2-hydroxy-2-methyl-propyl)amino)propyl)-benzonitrile,
(9) 3-(1(S)-(4-chlorobenzyl)-2(S)-((1-(2,4-difluorophenyl)-2-hydroxy-2-methyl-propyl)amino)propyl)benzonitrile,
(10) 3-(1(S)-(4-chlorobenzyl)-2(S)-((1-(3,4-difluorophenyl)-2-hydroxy-2-methyl-propyl)amino)propyl)benzonitrile,
(11) 3-(1(S)-(4-chlorobenzyl)-2(S)-((1-(2-chloro-4-fluorophenyl)-2-hydroxy-2-methyl-propyl)amino)propyl)benzonitrile,
(12) 3-(1(S)-(4-chlorobenzyl)-2(S)-((1-(2-fluoro-4-chlorophenyl)-2-hydroxy-2-methyl-propyl)amino)propyl)benzonitrile,
(13) 3-(1(S)-(4-chlorobenzyl)-2(S)-((1-(4-fluorophenyl)-2-hydroxy-2-methyl-propyl)amino)propyl)benzonitrile,
(14) 3-(1(S)-(4-chlorobenzyl)-2(S)-(((1-hydroxycyclobutyl)-(3,5-difluorophenyl)methyl)amino)propyl)benzonitrile,
(15) 3-(1(S)-(4-chlorobenzyl)-2(S)-(((1-hydroxycyclohexyl)-(3,5-difluorophenyl)methyl)amino)propyl)benzonitrile,
(16) 3-(1(S)-(4-chlorobenzyl)-2(S)-((1-(3,5-difluorophenyl)-2-hydroxy-2-ethyl-butyl)amino)propyl)benzonitrile,
(17) 3-(1(S)-(4-chlorobenzyl)-2(S)-((1-(3,5-difluorophenyl)-2-hydroxy-2-methoxymethyl-propyl)amino)propyl)benzonitrile,
(18) 3-(1(S)-(4-chlorobenzyl)-2(S)-((1-(3,5-difluorophenyl)-2-hydroxy-propyl)amino)propyl)-benzonitrile,
(19) 3-(1(S)-(4-chlorobenzyl)-2(S)-((1-phenyl-3-hydroxy-2,2-dimethylpropyl)amino)propyl) benzonitrile,
(20) 3-(1(S)-(4-chlorobenzyl)-2(S)-((1-phenyl-2-acetylamino-propyl)amino)propyl)benzonitrile,
(21) 3-(1(S)-(4-chlorobenzyl)-2(S)-((1-phenyl-2-t-butyloxycarbonyl-aminoethyl)-amino)propyl)benzonitrile,
(22) 3-(1(S)-(4-chlorobenzyl)-2(S)-((1-phenyl-2-aminoethyl)amino)-propyl)benzonitrile,
(23) 3-(1(S)-(4-chlorobenzyl)-2(S)-((1-phenyl-2-cyanoethyl)amino)propyl)benzonitrile,
(24) 3-(1(S)-(4-chlorobenzyl)-2(S)-((1-phenyl-2-cyano-2-methylpropyl)-amino)propyl)benzonitrile,
(25) 3-(1(S)-(4-chlorobenzyl)-2(S)-((1-(3,5-difluorophenyl)-2-cyano-2-methylpropyl)amino)propyl) benzonitrile, or
(26) 3-(1(S)-(4-chlorobenzyl)-2(S)-((1-phenyl-2-methane-sulfonylethyl)amino)propyl)benzonitrile,
and pharmaceutically acceptable salts thereof.

7. The compound according to claim 1 selected from:
(1) 3-(1(S)-(4-chlorobenzyl)-2(S)-((1-phenyl-2-(1H-pyrazol-1-yl)ethyl) amino)propyl)benzonitrile, (2) 3-(1(S)-(4-chlorobenzyl)-2(S)-((2-methyl-1-phenyl-2-(1H-pyrazol-1-yl)propyl) amino)propyl)benzonitrile, (3) 3-(1(S)-(4-chlorobenzyl)-2(S)-((1-phenyl-2-(1H,1,2,4-triazol-1-yl)ethyl) amino)propyl)benzonitrile, (4) 3-(1(S)-(4-chlorobenzyl)-2(S)-((2-(2-oxopyridin-1(2H)-yl-1-phenyl-ethyl) amino)propyl)benzonitrile, (5) 3-(1(S)-(4-chlorobenzyl)-2(S)-((1-biphenyl-4-yl-2-cyanoethylamino)-propyl)benzonitrile (diastereomer A), (6) 3-(1(S)-(4-chlorobenzyl)-2(S)-((1-biphenyl-4-yl-2-cyano-2-methyl-propyl)amino)propyl) benzonitrile (diastereomer A), (7) 3-(1(S)-(4-chlorobenzyl)-2(S)-((1-(3-bromophenyl)-2-cyanoethyl) amino)propyl)benzonitrile, (8) 3-(1(S)-(4-chlorobenzyl)-2(S)-((1-(4-chlorophenyl)-2-cyanoethyl) amino)propyl)benzonitrile, (9) 3-(1(S)-(4-chlorobenzyl)-2(S)-((1-(4-fluorophenyl)-2-cyanoethyl) amino)propyl)benzonitrile,

(10) 3-(1(S)-(4-chlorobenzyl)-2(S)-((1-(3-chlorophenyl)-2-cyanoethyl) amino)propyl)benzonitrile,

(11) 3-(1(S)-(4-chlorobenzyl)-2(S)-((1-(3-trifluoromethylphenyl)-2-cyano-ethyl)amino)propyl)benzonitrile,

(12) 3-(1(S)-(4-chlorobenzyl)-2(S)-((1-(4-trifluoromethylphenyl)-2-cyano-ethyl)amino)propyl)benzonitrile,

(13) 3-(1(S)-(4-chlorobenzyl)-2(S)-((1-(4-methylphenyl)-2-cyanoethyl)-amino)propyl)benzonitrile,

(14) 3-(1(S)-(4-chlorobenzyl)-2(S)-((1-(4-methoxycarbonylphenyl)-2-cyano-ethyl)amino)propyl) benzonitrile

(15) 3-(1(S)-(4-chlorobenzyl)-2(S)-((1-(3-trifluoromethoxyphenyl)-2-cyano-ethyl)amino)propyl) benzonitrile,

(16) 3-(1(S)-(4-chlorobenzyl)-2(S)-((1-(3-methylphenyl)-2-cyanoethyl)-amino)propyl)benzonitrile,

(17) 3-(1(S)-(4-chlorobenzyl)-2(S)-((1-(2-chlorophenyl)-2-cyanoethyl)-amino)propyl)benzonitrile (diastereomer A),

(18) 3-(1(S)-(4-chlorobenzyl)-2(S)-((1-(3,4-dichlorophenyl)-2-cyanoethyl) amino)propyl)benzonitrile,

(19) 3-(1(S)-(4-chlorobenzyl)-2(S)-((1-(3-cyanophenyl)-2-cyanoethyl)-amino) propyl)benzonitrile,

(20) 3-(1(S)-(4-chlorobenzyl)-2(S)-((1-(3-cyanophenyl)-2-cyano-2-methyl-propyl)amino) propyl)benzonitrile,

(21) 3-(1(S)-(4-chlorobenzyl)-2(S)-((1-(4-methylthiophenyl)-2-cyano-ethyl)amino)propyl)benzonitrile,

(22) 3-(1(S)-(4-chlorobenzyl)-2(S)-((1-(4-cyanophenyl)-2-cyanoethyl)-amino)propyl)benzonitrile (diastereomer A),

(23) 3-(1(S)-(4-chlorobenzyl)-2(S)-((1-(4-methoxyphenyl)-2-cyanoethyl)-amino)propyl)benzonitrile (diastereomer A),

(24) 3-(1(S)-(4-chlorobenzyl)-2(S)-((1-(3-methylthiophenyl)-2-cyano-ethyl)amino)propyl)benzonitrile,

(25) 3-(1(S)-(4-chlorobenzyl)-2(S)-((1-biphenyl-3-yl-2-cyanoethyl)-amino)propyl)benzonitrile,

(26) 3-(1(S)-(4-chlorobenzyl)-2(S)-((1-(4-dimethylaminocarbonylphenyl)-2-cyanoethyl)amino)propyl) benzonitrile (diastereomer A),

(27) 3-(1(S)-(4-chlorobenzyl)-2(S)-((1-(4-dimethylaminocarbonylphenyl)-2-cyano-2-methylpropyl)amino) propyl)benzonitrile (diastereomer A),

(28) 3-(1(S)-(4-chlorobenzyl)-2(S)-((1-(4-(1H-pyrrol-1-yl)phenyl)-2-cyano-2-methylpropyl)amino)propyl) benzonitrile (diastereomer A),

(29) 3-(1(S)-(4-chlorobenzyl)-2(S)-((1-(3-(1H-pyrazol-1-yl)phenyl)-2-cyano-2-methylpropyl)amino)propyl) benzonitrile,

(30) 3-(1(S)-(4-chlorobenzyl)-2(S)-((1-(4-(1H-imidazol-1-yl)phenyl)-2-cyano-2-methylpropyl)amino)propyl) benzonitrile (diastereomer A),

(31) 3-(1(S)-(4-chlorophenyl)-2(S)-((1-(4-chlorophenyl)-2-cyano-2-methylpropyl)amino)propyl) benzonitrile,

(32) 3-(1(S)-(4-chlorobenzyl)-2(S)-((1-(4-fluorophenyl)-2-cyano-2-methylpropyl)amino)propyl) benzonitrile (diastereomer A),

(33) 3-(1(S)-(4-chlorobenzyl)-2(S)-((1-(3-chlorophenyl)-2-cyano-2-methylpropyl)amino)propyl) benzonitrile (diastereomer A),

(34) 3-(1(S)-(4-chlorobenzyl)-2(S)-((1-(3-trifluoromethylphenyl)-2-cyano-2-methylpropyl)amino)propyl) benzonitrile (diastereomer A),

(35) 3-(1(S)-(4-chlorobenzyl)-2(S)-((1-(4-trifluoromethylphenyl)-2-cyano-2-methylpropyl)amino)propyl) benzonitrile (diastereomer A),

(36) 3-(1(S)-(4-chlorobenzyl)-2(S)-((1-(4-methylphenyl)-2-cyano-2-methylpropyl)amino)propyl) benzonitrile (diastereomer A),

(37) 3-(1(S)-(4-chlorobenzyl)-2(S)-((1-(4-methoxycarbonylphenyl)-2-cyano-2-methylpropyl)amino)propyl) benzonitrile (diastereomer A),

(38) 3-(1(S)-(4-chlorobenzyl)-2(S)-((1-(4-trifluoromethoxyphenyl)-2-cyano-2-methylpropyl)amino) propyl) benzonitrile (diastereomer A),

(39) 3-(1(S)-(4-chlorobenzyl)-2(S)-((1-(3-methylphenyl)-2-cyano-2-methylpropyl)amino)propyl) benzonitrile (diastereomer A),

(40) 3-(1(S)-(4-chlorobenzyl)-2(S)-((1-(4-cyanophenyl)-2-cyano-2-methylpropyl)amino)propyl) benzonitrile (diastereomer A),

(41) 3-(1(S)-(4-chlorobenzyl)-2(S)-((1-(3,4-dichlorophenyl)-2-cyano-2-methylpropyl)amino)propyl) benzonitrile (diastereomer A),

(42) 3-(1(S)-(4-chlorobenzyl)-2(S)-((1-(2-chlorophenyl)-2-cyano-2-methylpropyl)amino)propyl) benzonitrile (diastereomer A),

(43) 3-(1(S)-(4-chlorobenzyl)-2(S)-((1-(4-methylthiophenyl)-2-cyano-2-methylpropyl)amino)propyl) benzonitrile (diastereomer A),

(44) 3-(1(S)-(4-chlorobenzyl)-2(S)-((1-(4-methoxyphenyl)-2-cyano-2-methylpropyl)amino)propyl) benzonitrile (diastereomer A),

(45) 3-(1(S)-(4-chlorobenzyl)-2(S)-((1-(3-methylthiophenyl)-2-cyano-2-methylpropyl)amino)propyl) benzonitrile (diastereomer A),

(46) 3-(1(S)-(4-chlorobenzyl)-2(S)-((1-(3-phenylphenyl)-2-cyano-2-methylpropyl)amino)propyl) benzonitrile (diastereomer A),

(47) 3-(1(S)-(4-chlorobenzyl)-2(S)-((1-(4-bromophenyl)-2-cyano-2-methylpropyl)amino)propyl) benzonitrile (diastereomer A),

(48) 3-(1(S)-(4-chlorobenzyl)-2(S)-((1-(4-(1H-pyrazol-3-yl)phenyl)-2-cyano-2-methylpropyl)amino)propyl) benzonitrile (diastereomer A),

(49) 3-(1(S)-(4-chlorobenzyl)-2(S)-((1-(4-pyridin-4-ylphenyl)-2-cyano-2-methylpropyl)amino) propyl) benzonitrile (diastereomer A),

(50) 3-(1(S)-(4-chlorobenzyl)-2(S)-((1-(4-pyridin-3-ylphenyl)-2-cyano-2-methylpropyl)amino) propyl) benzonitrile (diastereomer A),

(51) 3-(1(S)-(4-chlorobenzyl)-2(S)-((1-(4'-cyanobiphen-4-yl)-2-cyano-2-methylpropyl)amino)propyl) benzonitrile (diastereomer A),

(52) 3-(1(S)-(4-chlorobenzyl)-2(S)-((1-(4-pyrimidin-5-yl-phenyl)-2-cyano-2-methylpropyl)amino)propyl)benzonitrile (diastereomer A),
(53) 3-(1(S)-(4-chlorobenzyl)-2(S)-((1-(4-(2-fluoropyridin-4-yl)-phenyl)-2-cyano-2-methylpropyl)amino) propyl)benzonitrile (diastereomer A),
(54) 3-(1(S)-(4-chlorobenzyl)-2(S)-((1-(4'-cyanobiphen-3-yl)-2-cyano-2-methylpropyl)amino)propyl) beuzonitrile (diastereomer A),
(55) 3-(1(S)-(4-chlorobenzyl)-2(S)-((1-(3-pyridin-3-yl-phenyl)-2-cyano-2-methylpropyl)amino)propyl) benzonitrile (diastereomer A),
(56) 3-(1(S)-(4-chlorobenzyl)-2(S)-((1-(3-pyrimidin-5-yl-phenyl)-2-cyano-2-methylpropyl)amino)propyl)benzonitrile (diastereomer A),
(57) 3-(1(S)-(4-chlorobenzyl)-2(S)-((1-(3-pyridin-4-yl-phenyl)-2-cyano-2-methylpropyl)amino)propyl) benzonitrile (diastereomer A),
(58) 3-(1(S)-(4-chlorobenzyl)-2(S)-((1-(3-(1H-pyrazol-3-yl)-phenyl)-2-cyano-2-methylpropyl)amino) propyl) benzonitrile (diastereomer A),
(59) 3-(1(S)-(4-chlorobenzyl)-2(S)-((1-(3'-cyanobiphen-3-yl)-2-cyano-2-methylpropyl)amino) propyl) benzonitrile (diastereomer A),
(60) 3-(1(S)-(4-chlorobenzyl)-2(S)-((1-(4-methanesulfonylphenyl)-2-cyano-2-methylpropyl)amino) propyl) benzonitrile (diastereomer A),
(61) 3-(1(S)-(4-chlorobenzyl)-2(S)-((1-(4-methanesulfinylphenyl)-2-cyano-2-methylpropyl)amino) propyl) benzonitrile (diastereomer A),
(62) 3-(1(S)-(4-chlorobenzyl)-2(S)-((1-(3-methanesulfonylphenyl)-2-cyano-2-methylpropyl)amino) propyl) benzonitrile (diastereomer A),
(63) 3-(1(S)-(4-chlorobenzyl)-2(S)-((1-(3-methanesulfinylphenyl)-2-cyano-2-methylpropyl)amino) propyl) benzonitrile (diastereomer A),
(64) 3-(1(S)-(4-chlorobenzyl)-2(S)-((1-(4-(1H-1,2,4-triazol-1-yl)phenyl)-2-cyano-2-methylpropyl) amino)propyl) benzonitrile (diastereomer A),
(65) 3-(1(S)-(4-chlorobenzyl)-2(S)-((1-(4-(1H-1,2,5-triazol-1-yl)phenyl)-2-cyano-2-methylpropyl)amino) propyl)benzonitrile (diastereomer A),
(66) 3-(1(S)-(4-chlorobenzyl)-2(S)-((1-(4-(1H-1,2,3-triazol-1-yl)phenyl)-2-cyano-2-methylpropyl)amino)propyl)benzonitrile (diastereomer A),
(67) 3-(1(S)-(4-chlorobenzyl)-2(S)-((1-(3-(1H-1,2,4-triazol-1-yl)phenyl)-2-cyano-2-methylpropyl)amino) propyl)benzonitrile (diastereomer A),
(68) 3-(1(S)-(4-chlorobenzyl)-2(S)-((1-(3-(1H-1,2,5-triazol-1-yl)phenyl)-2-cyano-2-methylpropyl)amino) propyl)benzonitrile (diastereomer A),
(69) 3-(1(S)-(4-chlorobenzyl)-2(S)-((1-(3-(1H-1,2,3-triazol-1-yl)phenyl)-2-cyano-2-methylpropyl)amino) propyl)benzonitrile (diastereomer A),
(70) 3-(1(S)-(4-chlorobenzyl)-2(S)-((1-(4-(1H-pyrazol-1-yl)phenyl)-2-cyano-2-methylpropyl)amino) propyl) benzonitrile (diastereomer A),
(71) 3-(1(S)-(4-chlorobenzyl)-2(S)-((1-(4-(1H-pyrazol-3-ylamino)phenyl)-2-cyano-2-methylpropyl)amino)propyl) benzonitrile (diastereomer A),
(72) 3-(1(S)-(4-chlorobenzyl)-2(S)-((1-(4-(1H-1,2,4-triazol-3-ylamino)phenyl)-2-cyano-2-methylpropyl) amino) propyl)benzonitrile (diastereomer A),
(73) 3-(1(S)-(4-chlorobenzyl)-2(S)-((1-(4-(3-amino-1H-1,2,4-triazol-1-yl)phenyl)-2-cyano-2-methylpropyl) amino) propyl)benzonitrile (diastereomer A),
(74) 3-(1(S)-(4-chlorobenzyl)-2(S)-((1-(3-(1H-pyrazol-3-ylamino)phenyl)-2-cyano-2-methylpropyl)amino) propyl)benzonitrile (diastereomer A),
(75) 3-(1(S)-(4-chlorobenzyl)-2(S)-((1-(3-(1H-1,2,4-triazol-3-ylamino)phenyl)-2-cyano-2-methylpropyl) amino) propyl)benzonitrile (diastereomer A), or
(76) 3-(1(S)-(4-chlorobenzyl)-2(S)-((1-(3-(pyridine-2-ylamino)phenyl)-2-cyano-2-methylpropyl)amino) propyl)benzonitrile (diastereomer A),
and pharmaceutically acceptable salts thereof.

8. A compound of structural formula I:

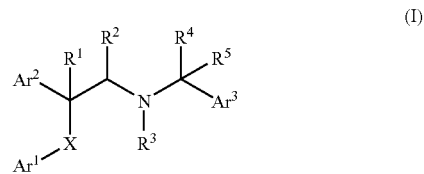

(I)

or a pharmaceutically acceptable salt thereof, wherein:
$R^1$ is
hydrogen
(4);
$R^2$ is —$CH_3$,
wherein each —$CH_3$ moiety is unsubstituted or substituted with 1, 2 or 3 $R^e$ substituents;
$R^3$ is
hydrogen
(2);
$R^4$ is selected from:
(1) hydrogen,
(2) $C_{1-10}$alkyl,
(3) $C_{2-10}$alkenyl,
(4) $C_{2-10}$alkynyl,
(5) $C_{1-10}$alkyloxycarbonyl-, and
(6) $C_{3-10}$cycloalkyl,
wherein each alkyl, alkenyl, and alkynyl moiety is unsubstituted or substituted with one to four substituents independently selected from $R^a$ and each cycloalkyl moeity is unsubstituted or substituted with one, two or three substituents independently selected from $R^b$;
$R^5$ is
hydrogen
(2);
$Ar^1$ is phenyl,
(7)
wherein each phenyl moiety is unsubstituted or substituted with one to four substituents independently selected from $R^b$;
$Ar^2$ is phenyl,
wherein each phenyl moiety is unsubstituted or substituted with one to four substituents independently selected from $R^b$;
$Ar^3$ is phenyl,
wherein each phenyl moiety is unsubstituted or substituted with one to four substituents independently selected from $R^b$;
X is —$CH_2$—;
each $R^a$ is independently selected from:
(1) —$OR^d$,
(2) —$NR^cS(O)_mR^d$,
(3) halogen,
(4) —$SR^d$,
(5) —$S(O)_mR^d$, (6) —S(O)$_m$NR$^c$R$^d$,
(7) —NR$^c$R$^d$,
(8) —C(O)R$^d$,
(9) —CO$_2$R$^d$,
(10) —CN,
(11) —C(O)NR$^c$R$^d$,
(12) —NR$^c$C(O)R$^d$,
(13) —NR$^c$C(O)OR$^d$,
(14) —NR$^c$C(O)NR$^c$R$^d$,
(15) —CF$_3$,
(16) —OCF$_3$, and
(17) cycloheteroalkyl;

each R$^b$ is independently selected from:
(1) R$^a$,
(2) C$_{1-10}$alkyl,
(3) aryl,
(4) arylC$_{1-4}$alkyl,
(5) heteroaryl, and
(6) heteroarylC$_{1-4}$alkyl;

R$^c$ and R$^d$ are independently selected from:
(1) hydrogen,
(2) C$_{1-10}$alkyl,
(3) C$_{2-10}$ alkenyl,
(4) cycloalkyl,
(5) cycloalkyl-C$_{1-10}$alkyl-,
(6) cycloheteroalkyl,
(7) cycloheteroalkyl-C$_{1-10}$ alkyl-,
(8) aryl,
(9) heteroaryl,
(10) aryl-C$_{1-10}$alkyl-, and
(11) heteroaryl-C$_{1-10}$alkyl-, or R$^c$ and R$^d$ together with the atom(s) to which they are attached form a heterocyclic ring of 4 to 7 members containing 0-2 additional heteroatoms independently selected from oxygen, sulfur and N—R$^g$, each R$^c$ and R$^d$ are unsubstituted or substituted with one to three substituents selected from R$^h$;

R$^e$ is selected from:
(1) hydroxy,
(2) methoxy-,
(3) trifluoromethoxy-,
(4) methylcarbonyloxy-,
(5) halogen, and
(6) cyano;

each R$^g$ is independently selected from
(1) C$_{1-10}$alkyl, and
(2) —C(O)R$^i$;

each R$^h$ is independently selected from:
(1) halogen,
(2) C$_{1-10}$alkyl,
(3) —O—C$_{1-4}$alkyl,
(4) —S—C$_{1-4}$alkyl,
(5) —CN,
(6) —NO$_2$,
(7) —CF$_3$, and
(8) —OCF$_3$;

each R$^i$ is independently selected from:
(1) hydrogen,
(2) C$_{1-10}$alkyl,
(3) C$_{2-10}$alkenyl,
(4) cycloalkyl,
(5) cycloalkyl-C$_{1-10}$alkyl-,
(6) cycloheteroalkyl,
(7) cycloheteroalkyl-C$_{1-10}$ alkyl-,
(8) aryl,
(9) heteroaryl,
(10) aryl-C$_{1-10}$alkyl-, and
(11) heteroaryl-C$_{1-10}$alkyl-; and m is selected from 1 and 2.

9. A composition comprising a compound according to claim 1 and a pharmaceutically acceptable carrier.

10. A method for treating obesity in a person at risk therefore comprising administration to the person of about 0.001 mg/kg to about 100 mg/kg of a compound according to claim 1.

11. A method of treating obesity in a human patient in need of such treatment comprising administration of a non-toxic, therapeutically effective amount of a compound according to claim 1.

* * * * *